US012741937B2

(12) United States Patent
Yu et al.

(10) Patent No.: US 12,741,937 B2
(45) Date of Patent: Sep. 22, 2026

(54) TAUTOMERIC LIGAND ENABLES BIOMIMETIC C—H HYDROXYLATION WITH MOLECULAR OXYGEN

(71) Applicant: THE SCRIPPS RESEARCH INSTITUTE, La Jolla, CA (US)

(72) Inventors: Jin-Quan Yu, San Diego, CA (US); Zhen Wang, San Diego, CA (US); Zhen Li, San Diego, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 464 days.

(21) Appl. No.: 18/256,680

(22) PCT Filed: Dec. 9, 2021

(86) PCT No.: PCT/US2021/062538

§ 371 (c)(1),
(2) Date: Jun. 9, 2023

(87) PCT Pub. No.: WO2022/125736

PCT Pub. Date: Jun. 16, 2022

(65) Prior Publication Data

US 2024/0059656 A1 Feb. 22, 2024

Related U.S. Application Data

(60) Provisional application No. 63/124,544, filed on Dec. 11, 2020.

(51) Int. Cl.

| | |
|---|---|
| ***C07D 213/803*** | (2006.01) |
| ***C07C 51/373*** | (2006.01) |
| ***C07C 227/10*** | (2006.01) |
| ***C07C 231/12*** | (2006.01) |
| ***C07C 303/40*** | (2006.01) |
| ***C07D 209/08*** | (2006.01) |
| ***C07D 209/26*** | (2006.01) |
| ***C07D 209/86*** | (2006.01) |
| ***C07D 213/55*** | (2006.01) |
| ***C07D 213/61*** | (2006.01) |
| ***C07D 213/643*** | (2006.01) |
| ***C07D 213/69*** | (2006.01) |
| ***C07D 213/74*** | (2006.01) |
| ***C07D 215/48*** | (2006.01) |

(Continued)

(52) U.S. Cl.

CPC ........ *C07D 213/803* (2013.01); *C07C 51/373* (2013.01); *C07C 227/10* (2013.01); *C07C 231/12* (2013.01); *C07C 303/40* (2013.01); *C07D 209/08* (2013.01); *C07D 209/26* (2013.01); *C07D 209/86* (2013.01); *C07D 213/55* (2013.01); *C07D 213/61* (2013.01); *C07D 213/643* (2013.01); *C07D 213/69* (2013.01); *C07D 213/74* (2013.01); *C07D 215/48* (2013.01); *C07D 215/50* (2013.01); *C07D 235/20* (2013.01); *C07D 241/42* (2013.01); *C07D 271/06* (2013.01); *C07D 277/64* (2013.01); *C07D 295/155* (2013.01); *C07D 307/79* (2013.01); *C07D 307/91* (2013.01); *C07D 319/18* (2013.01); *C07D 333/54* (2013.01); *C07D 333/76* (2013.01); *C07F 15/0066* (2013.01); *C07K 5/06078* (2013.01)

(58) Field of Classification Search

CPC .......................... C07D 213/803; C07D 213/55; C07D 213/61; C07D 213/643; C07D 213/69; C07D 213/74; C07D 209/08; C07D 26/86; C07D 215/48; C07D 215/50; C07D 235/20; C07D 241/42; C07D 271/06; C07D 277/64; C07D 295/155; C07D 307/79; C07D 307/91; C07D 319/18; C07D 333/54; C07D 333/76; C07C 51/373; C07C 227/10; C07C 231/12; C07C 303/40; C07F 15/0066; C07K 5/06078

See application file for complete search history.

(56) References Cited

U.S. PATENT DOCUMENTS 5,981,424 A 11/1999 Durante et al.

FOREIGN PATENT DOCUMENTS

CN 107253894 A 10/2017
CN 107709293 A 2/2018

(Continued)

OTHER PUBLICATIONS

Zhang, J Am Chem Soc, 2009, vol. 131, 14651-14655. (Year: 2009).*

(Continued)

*Primary Examiner* — D Margaret M Seaman
(74) *Attorney, Agent, or Firm* — Viksnins Harris Padys Malen LLP

(57) ABSTRACT

Disclosed herein is a process for making a compound of formula (2) by (hetero)aromatic C—H hydroxylation of a compound of formula (1): catalyzed by palladium(II) and a bidentate ligand in the presence of $O_2$. The process is useful for instance, in the late-stage modification of medicinally important heterocycles.

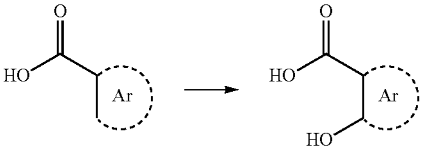

(1) (2)

9 Claims, 2 Drawing Sheets

(51) Int. Cl.

| | |
|---|---|
| ***C07D 215/50*** | (2006.01) |
| ***C07D 235/20*** | (2006.01) |
| ***C07D 241/42*** | (2006.01) |
| ***C07D 271/06*** | (2006.01) |
| ***C07D 277/64*** | (2006.01) |
| ***C07D 295/155*** | (2006.01) |
| ***C07D 307/79*** | (2006.01) |
| ***C07D 307/91*** | (2006.01) |
| ***C07D 319/18*** | (2006.01) |
| ***C07D 333/54*** | (2006.01) |
| ***C07D 333/76*** | (2006.01) |
| ***C07F 15/00*** | (2006.01) |
| ***C07K 5/065*** | (2006.01) |

(56) References Cited

FOREIGN PATENT DOCUMENTS

| | | | |
|---|---|---|---|
| CN | 111087343 A | | 5/2020 |
| CN | 111386265 A | | 7/2020 |
| WO | 2011037929 | * | 3/2011 |

OTHER PUBLICATIONS

Zhang, J Am Chem Soc, 2009, vol. 131, 14651-14655. (Year: 2011).*

Deng, et al., “Alkylation of Aromatic Amines with Trialkyl Amines Catalyzed by a Defined Iridium Complex with a 2-Hydroxypyridylmethylene Fragment”, Organometallics 38, 2218-2226 (2019).

Li, et al., “A tautomeric ligand enables directed C—H hydroxylation with molecular oxygen”, Science 372(6549), 1452-1457 (2021).

Patent Cooperation Treaty, International Search Report and Written Opinion for PCT/US2021/062538, 11 pages, dated Mar. 29, 2022.

Salamanca, et al., “[2,2' -Bipyridin]-6(1H)-one, a Truly Cooperating Ligand in the Palladium-Mediated C—H Activation Step: Experimental Evidence in the Direct C-3 Arylation of Pyridine”, J Am. Chem. Soc. 140, 17851-17856 (2018).

* cited by examiner

TAUTOMERIC LIGAND ENABLES BIOMIMETIC C—H HYDROXYLATION WITH MOLECULAR OXYGEN

CLAIM OF PRIORITY

The present application claims the benefit of priority to U.S. Provisional Application No. 63/124,544 filed on Dec. 11, 2020, which application is incorporated herein as if fully set forth.

STATEMENT OF GOVERNMENT SUPPORT

This invention was made with government support under GM102265 awarded by the National Institutes of Health. The government has certain rights in the invention.

BACKGROUND

Hydroxylation of aromatic compounds is an important chemical transformation in various metabolic pathways and organic synthesis due to the ubiquity of the phenol motif.

The most attractive catalytic system for achieving this transformation is the enzymatic hydroxylation of aryl C—H bonds with molecular oxygen catalyzed by monooxygenases[10], as exemplified by the Cytochrome P450 camphor.[1,2] Prompted by these enzymatic processes, long standing efforts have been dedicated to the ultimate development of a synthetic catalyst that can perform arene hydroxylation with $O_2$ in analogous manner. Mechanistic investigations into heme and non-heme iron enzymes using multidisciplinary tools have revealed details of how iron centers activate $O_2$ to generate reactive species with different valence. Biomimetic C—H hydroxylation using organometallic iron complexes with $H_2O_2$ as the oxidant has also been extensively investigated.[11] These investigations triggered efforts to establish a synthetic transition metal model that can mimic how iron centers activate $O_2$, which is an essential component for the ultimate design of a transition metal catalyst that can catalyze C—H hydroxylation with $O_2$.

Based upon the Shilov system,[12] some studies focus upon the reactivity of $L_2Pt(II)\text{-}Me_2$ with $O_2$.[3] For example, a Pt(II)-alkyl complex supported by a tripod ligand was shown to react with $O_2$ to give Pt—OOH species analogous to heme-enzymes.[9] While analogous Pd(II)-alkyl complexes could react with $O_2$ through a radical chain mechanism,[5,6] more recent evidence supports a biomimetic activation of $O_2$ by a Pd(II)alkyl species supported by a tripod ligand.[7,8] The specially designed tripod ligand promotes the oxidation of synthetic Pd(II)alkyl complexes to form Pd(IV)alkyl(OOH) species and the subsequent C—O reductive elimination. However, merging this elementary step with C—H activation to close the catalytic cycle remains a tremendous challenge because no ligand is compatible with both events, specifically (1) activation of C—H bonds in synthetically relevant substrates and (2) oxidation with $O_2$ and subsequent reductive C—OH reductive elimination sequentially under the same catalytic conditions.

Despite the accumulated mechanistic insights on the elementary steps of the proposed catalytic cycle for Pd-catalyzed aerobic C—H hydroxylation and other Pd-catalyzed aerobic oxidation with $O_2$,[13,14] development of a desired catalyst has enjoyed only limited success. The use of a tripod ligand led to an acetoxylation reaction of benzylic C—H bonds using $O_2$ as the oxidant, although the mechanistic role of $O_2$ remains to be elucidated.[15] In addition, this reactivity is limited to quinoline-directed cyclopalladation process. A single example of aryl C—H hydroxylation catalyzed by $Pd(OAc)_2$ salts was observed,[16] but without any supporting ligand or well-defined catalysts, and the substrate scope was limited to benzoic acids and for some cases even required the use of 5 atm of $O_2$ to achieve decent reactivity.

SUMMARY

The present disclosure overcomes these challenges and others by providing, in various embodiments, a process for making a compound of formula (2):

(2)

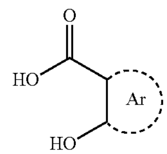

The process comprises contacting a compound of formula (1):

(1)

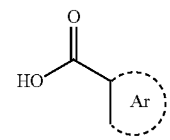

with a source of Pd(II) in the presence of $O_2$ and a ligand of formula (L):

(L)

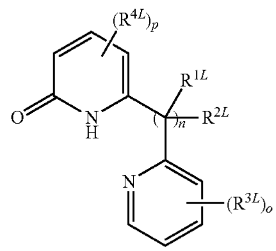

whereby the compound of formula (2) is formed.

The moiety

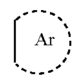

is a $C_6$-$C_{10}$-aryl or 5-10-membered heteroaryl (wherein 1-4 heteroaryl ring members are independently selected from the group consisting of O, S, and N). The moiety

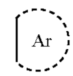

is optionally further fused to one or two rings that are independently selected from $C_6$-$C_{10}$-aryl, $C_3$-$C_{14}$-cycloalkyl, 5-10-membered heteroaryl (wherein 1-4 heteroaryl ring members are independently selected from the group consisting of O, S, and N), 3- to 14-membered heterocycloalkyl (wherein 1-4 heterocycloalkyl ring members are independently selected from N, O, and S), and fused combinations thereof.

Each ring in

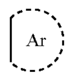

is independently and optionally substituted with one to four substituents selected from the group consisting of —CN, halo, oxo, $NR^AR^B$, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, $C(O)C_1$-$C_6$-alkyl, $C(O)NR^AR^B$, $S(O)NR^AR^B$, $S(O)_2NR^AR^B$, $C_3$-$C_{14}$-cycloalkyl, $C_6$-$C_{10}$-aryl, $C_6$-$C_{10}$-aryloxy, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S), wherein each alkyl, aryl, cycloalkyl, heterocycloalkyl, and heteroaryl moiety is optionally substituted with one to four substituents selected from the group consisting of halo, oxo, $C_1$-$C_6$-alkyl, $C_1$-$C_6$-haloalkyl, $C_1$-$C_6$-alkoxy, $C(O)NR^AR^B$, $C_1$-$C_6$-alkoxy, $C_6$-$C_{10}$-aryl (optionally substituted by one to three halo and $C_1$-$C_6$-alkyl), and 5- to 10-membered heteroaryl (wherein 1-4 heteroaryl members are independently selected from N, O, and S; optionally substituted by one to three substituents selected from $C_1$-$C_6$-alkyl and 5- to 10-membered heteroaryl).

$R^A$ and $R^B$ are independently selected from the group consisting of H, $C_1$-$C_6$-alkyl, $C_1$-$C_6$-haloalkyl, —$C_1$-$C_6$-alkyl-$C_6$-$C_{10}$-aryl, $C(O)C_1$-$C_6$-alkyl, $C(O)C_1$-$C_6$-alkyl-$C_6$-$C_{10}$-aryl, $C(O)OC_1$-$C_6$-alkyl, $C_6$-$C_{10}$-aryl (optionally fused to $C_3$-$C_{14}$-cycloalkyl that is optionally substituted by one to four halo and $C_1$-$C_6$-alkyl), wherein each aryl is optionally substituted with one to three substituents selected from $C_1$-$C_6$-alkyl, halo, $C_1$-$C_6$-haloalkyl, and 3- to 14-membered heterocycloalkyl (wherein 1-4 ring members are independently selected from N, O, and S); and wherein each alkyl is optionally substituted with one to three substituents selected from halo, NRR' (wherein R and R' are independently selected from H, $C_1$-$C_6$-alkyl, $C(O)C_1$-$C_6$-alkyl, and $C(O)C_6$-$C_{10}$-aryl).

$R^{1L}$ and $R^{2L}$ are independently selected from the group consisting of H, $C_1$-$C_6$-alkyl, $C_6$-$C_{10}$-aryl, —($C_1$-$C_6$-alkyl) $C_6$-$C_{10}$-aryl, 5-10-membered heteroaryl (wherein 1-4 heteroaryl ring members are independently selected from the group consisting of O, S, and N), and $C_3$-$C_{14}$-cycloalkyl, wherein each aryl is optionally substituted with one to three substituents independently selected from the group consisting of $C_1$-$C_6$-alkyl, halo, $C_1$-$C_6$-haloalkyl, and $C_1$-$C_6$-alkoxy.

Each instance of $R^{3L}$ and $R^{4L}$ is independently selected from the group consisting of $C_1$-$C_6$-alkyl, halo, $C_1$-$C_6$-alkoxy, and $C_1$-$C_6$-haloalkyl.

The subscript n is an integer selected from 1, 2, and 3. The subscript o is an integer selected from 0, 1, 2, and 3. The subscript p is an integer selected from 0, 1, 2, and 3.

Additional embodiments of the present disclosure are disclosed in the drawings and detailed description herein.

DETAILED DESCRIPTION

Figure 1:
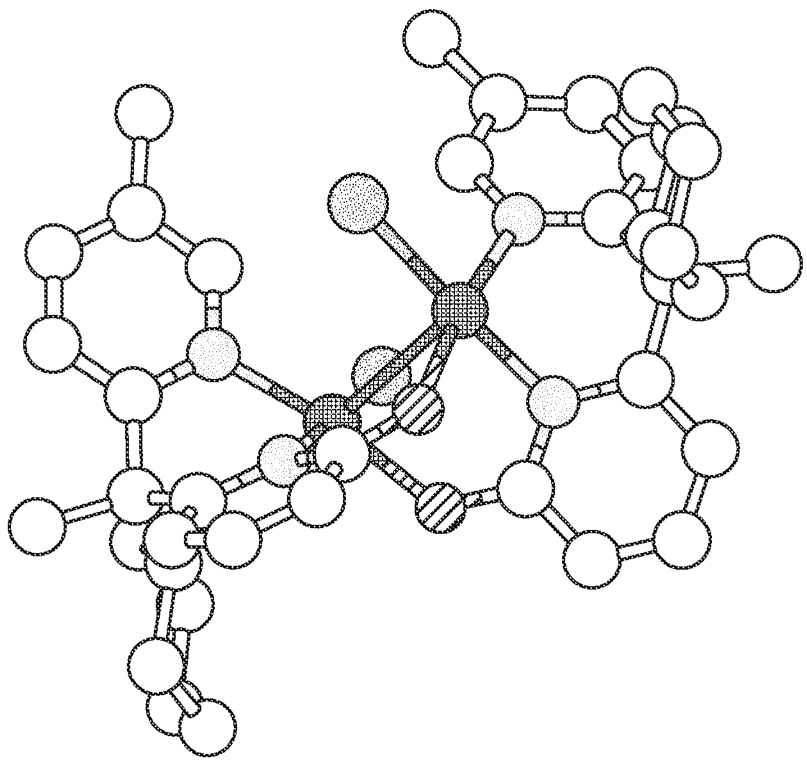
FIG. 1: Single crystal X-ray structure of $[Pd_2Cl_2(L42)_2]$ complex.

Despite the development of ligands that can accelerate Pd-catalyzed C—H activation reactions, none of the ligands are capable of also supporting an oxidation/hydroxylation step. More specifically, known mechanisms of $O_2$ activation and an understanding of ligand cooperation in the C—H activation militate against a single conventional ligand with one coordination mode that could accommodate both reactivities. In contrast, the present disclosure relates in part to the surprising discovery of a ligand scaffold that can tautomerize to coordinate with Pd centers in two distinct modes: one mode accelerates C—H activation, and another mode facilitates $O_2$ activation.

Definitions

"Alkyl" refers to straight or branched chain hydrocarbyl including from 1 to about 20 carbon atoms. For instance, an alkyl can have from 1 to 10 carbon atoms or 1 to 6 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, $—CH(CH_3)_2$, $—CH(CH_3)(CH_2CH_3)$, $—CH(CH_2CH_3)_2$, $—C(CH_3)_3$, $—C(CH_2CH_3)_3$, $—CH_2CH(CH_3)_2$, $—CH_2CH(CH_3)(CH_2CH_3)$, $—CH_2CH(CH_2CH_3)_2$, $—CH_2C(CH_3)_3$, $—CH_2C(CH_2CH_3)_3$, $—CH(CH_3)CH(CH_3)(CH_2CH_3)$, $—CH_2CH_2CH(CH_3)_2$, $—CH_2CH_2CH(CH_3)(CH_2CH_3)$, $—CH_2CH_2C H(CH_2CH_3)_2$, $—CH_2CH_2C(CH_3)_3$, $—CH_2CH_2C(CH_2CH_3)_3$, $—CH(CH_3)CH_2CH(CH_3)_2$, $—CH(CH_3) CH(CH_3)CH(CH_3)_2$, and the like. Thus, alkyl groups include primary alkyl groups, secondary alkyl groups, and tertiary alkyl groups. An alkyl group can be unsubstituted or optionally substituted with one or more substituents as described herein below.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F or fluoro, —Cl or chloro, —Br or bromo, or —I or iodo.

The term "alkenyl" refers to straight or branched chain hydrocarbyl groups including from 2 to about 20 carbon atoms having 1-3, 1-2, or at least one carbon to carbon double bond. An alkenyl group can be unsubstituted or optionally substituted with one or more substituents as described herein below.

"Substituted alkenyl" refers to alkenyl substituted at 1 or more, e.g., 1, 2, 3, 4, 5, or even 6 positions, which substituents are attached at any available atom to produce a stable compound, with substitution as described herein. "Optionally substituted alkenyl" refers to alkenyl or substituted alkenyl.

"Alkyne or "alkynyl" refers to a straight or branched chain unsaturated hydrocarbon having the indicated number of carbon atoms and at least one triple bond. Examples of a $(C_2-C_8)$alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

"Substituted alkynyl" refers to an alkynyl substituted at 1 or more, e.g., 1, 2, 3, 4, 5, or even 6 positions, which substituents are attached at any available atom to produce a stable compound, with substitution as described herein. "Optionally substituted alkynyl" refers to alkynyl or substituted alkynyl.

The term "alkoxy" refers to an —O-alkyl group having the indicated number of carbon atoms. For example, a $(C_1-C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "cycloalkyl" refers to a saturated monocyclic, bicyclic, tricyclic, polycyclic, and optionally spiro-fused 3- to 14-membered ring system. Cycloalkyl includes 3- to 10-membered, 3- to 8-membered, and 3- to 6-membered ring systems. The cycloalkyl may be attached via any atom. Representative examples of carbocyclyl include, but are not limited to cyclopropyl, cyclobutyl, cyclopentyl, cyclohexyl, cyclopropenyl, cyclobutenyl, cyclopentenyl, cyclohexenyl, and adamantyl. A carbocyclyl group can be unsubstituted or optionally substituted with one or more substituents as described herein below.

"Substituted cycloalkyl" refers to cycloalkyl substituted at 1 or more, e.g., 1, 2, 3, 4, 5, or even 6 positions, which substituents are attached at any available atom to produce a stable compound, with substitution as described herein. "Optionally substituted carbocyclyl" refers to carbocyclyl or substituted carbocyclyl.

"Aryl" when used alone or as part of another term means an optionally fused carbocyclic aromatic group having the number of carbon atoms designated or if no number is designated, up to 14 carbon atoms, such as a $C_6-C_{14}$-aryl or $C_6-C_{10}$-aryl. Illustrative aryl groups are phenyl, naphthyl, biphenyl, phenanthrenyl, naphthacenyl, and the like (see e.g. *Lang's Handbook of Chemistry* (Dean, J. A., ed) $13^{th}$ ed. Table 7-2 [1985]). A particular aryl is phenyl. "Aryl" can be optionally fused with a carbocyclyl ring, as herein defined. An aryl group can be unsubstituted or optionally substituted with one or more substituents as described herein below.

A "substituted aryl" is an aryl that is independently substituted with one or more substituents attached at any available atom to produce a stable compound, wherein the substituents are as described herein. "Optionally substituted aryl" refers to aryl or substituted aryl.

The term "heteroatom" refers to N, O, and S. Compounds of the present disclosure that contain N or S atoms can be optionally oxidized to the corresponding N-oxide, sulfoxide, or sulfone compounds.

"Heteroaryl," alone or in combination with any other moiety described herein, refers to a monocyclic aromatic ring structure containing 5 to 10, such as 5 or 6 ring atoms, or a bicyclic aromatic group having 8 to 10 atoms, containing one or more, such as 1-4, 1-3, or 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinaoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. A heteroaryl group can be unsubstituted or optionally substituted with one or more substituents as described herein below.

A "substituted heteroaryl" is a heteroaryl that is independently substituted, unless indicated otherwise, with one or more, e.g., 1, 2, 3, 4 or 5, also 1, 2, or 3 substituents, also 1 substituent, attached at any available atom to produce a stable compound, wherein the substituents are as described herein. "Optionally substituted heteroaryl" refers to heteroaryl or substituted heteroaryl.

"Heterocycloalkyl" means a saturated or partially unsaturated non-aromatic monocyclic, bicyclic, tricyclic or polycyclic ring system that has from 3 to 14, such as 3 to 10 or 3 to 6, atoms in which from 1 to 3 carbon atoms in the ring are replaced by heteroatoms of O, S or N. A heterocycloalkyl includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl. A heterocycloalkyl group can be unsubstituted or optionally substituted with one or more substituents as described herein below.

"Optionally substituted heterocycloalkyl" denotes a heterocycloalkyl that is substituted with 1 to 3 substituents, e.g., 1, 2 or 3 substituents, attached at any available atom to produce a stable compound, wherein the substituents are as described herein.

The term "nitrile" or "cyano" can be used interchangeably and refer to a —CN group which is bound to a carbon atom of a heteroaryl ring, aryl ring and a heterocycloalkyl ring.

The term "oxo" refers to ═O atom bound to an atom that is part of a saturated or unsaturated moiety. Thus, the ═O atom can be bound to a carbon, sulfur, or nitrogen atom that is part of a cyclic or acyclic moiety.

A "hydroxyl" or "hydroxy" refers to an —OH group.

The substituent $—CO_2H$ may be replaced with bioisosteric replacements such as:

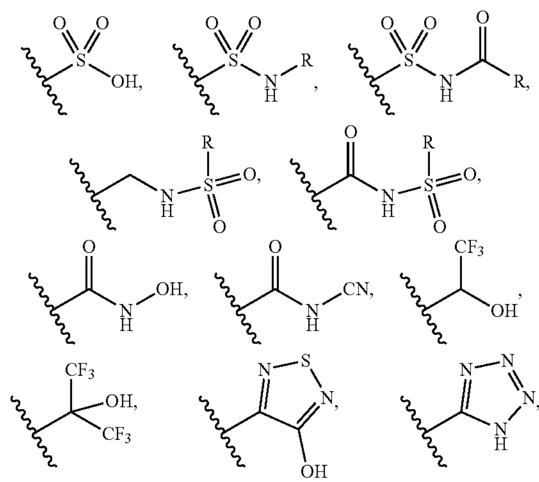

-continued

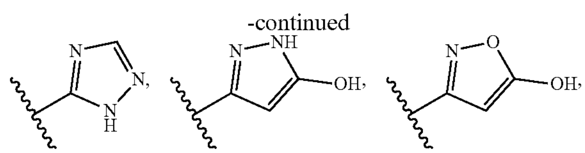

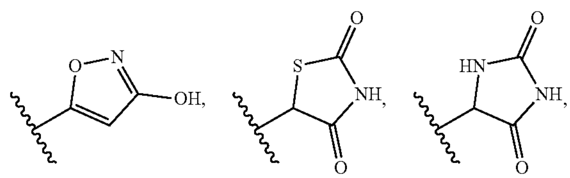

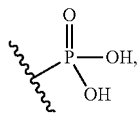

and the like, wherein R has the same definition as $R^A$ as defined herein. See, e.g., THE PRACTICE OF MEDICINAL CHEMISTRY (Academic Press: New York, 1996), at page 203.

Compounds described herein can exist in various isomeric forms, including configurational, geometric, and conformational isomers, including, for example, cis- or trans-conformations. The compounds may also exist in one or more tautomeric forms, including both single tautomers and mixtures of tautomers. The term "isomer" is intended to encompass all isomeric forms of a compound of this disclosure, including tautomeric forms of the compound. The compounds of the present disclosure may also exist in open-chain or cyclized forms. In some cases, one or more of the cyclized forms may result from the loss of water. The specific composition of the open-chain and cyclized forms may be dependent on how the compound is isolated, stored or administered. For example, the compound may exist primarily in an open-chained form under acidic conditions but cyclize under neutral conditions. All forms are included in the disclosure.

Some compounds described herein can have asymmetric centers and therefore exist in different enantiomeric and diastereomeric forms. A compound as described herein can be in the form of an optical isomer or a diastereomer. Accordingly, the disclosure encompasses compounds and their uses as described herein in the form of their optical isomers, diastereoisomers and mixtures thereof, including a racemic mixture. Optical isomers of the compounds of the disclosure can be obtained by known techniques such as asymmetric synthesis, chiral chromatography, simulated moving bed technology or via chemical separation of stereoisomers through the employment of optically active resolving agents.

Unless otherwise indicated, the term "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound. The stereoisomer as described above can be viewed as composition comprising two stereoisomers that are present in their respective weight percentages described herein.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

Process

The present disclosure relates in part to a process whereby ligands of formula (L) can facilitate both the oxidation/hydroxylation step in C—H activation. The process achieves this advantage, among others, because the ligand is choreographed to switch between coordination modes precisely at designated points in a catalytic cycle: one tautomer is for C—H activation, and another tautomer allows for $O_2$ activation.

In various embodiments, the present disclosure provides a process for making a compound of formula (2):

(2)

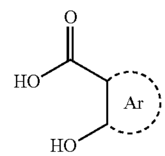

The process comprises contacting a compound of formula (1):

(1)

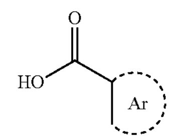

with a source of Pd(II) in the presence of $O_2$ and a ligand of formula (L):

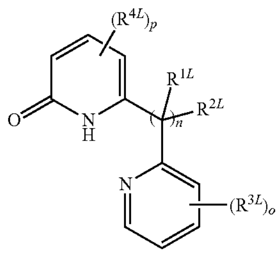

(L)

whereby the compound of formula (2) is formed.

The moiety

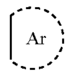

is a $C_6$-$C_{10}$-aryl or 5-10-membered heteroaryl (wherein 1-4 heteroaryl ring members are independently selected from the group consisting of O, S, and N). The moiety

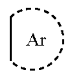

is optionally further fused to one or two rings that are independently selected from $C_6$-$C_{10}$-aryl, $C_3$-$C_{14}$-cycloalkyl, 5-10-membered heteroaryl (wherein 1-4 heteroaryl ring members are independently selected from the group consisting of O, S, and N), 3- to 14-membered heterocycloalkyl (wherein 1-4 heterocycloalkyl ring members are independently selected from N, O, and S), and fused combinations thereof.

Each ring in

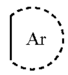

is independently and optionally substituted with one to four substituents selected from the group consisting of —CN, halo, oxo, $NR^AR^B$, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, —C(O)H, C(O)$C_1$-$C_6$-alkyl, C(O)$NR^AR^B$, S(O)$NR^AR^B$, $S(O)_2NR^AR^B$, $C_3$-$C_{14}$-cycloalkyl, $C_6$-$C_{10}$-aryl, $C_6$-$C_{10}$-aryloxy, 3- to 14-membered heterocycloalkyl and —($C_1$-$C_6$-alkyl)-(3- to 14-membered heterocycloalkyl) (wherein 1-4 ring members are independently selected from N, O, and S), and 5- to 10-membered heteroaryl (wherein 1-4 heteroaryl members are independently selected from N, O, and S), wherein each alkyl, aryl, cycloalkyl, heterocycloalkyl, and heteroaryl moiety is optionally substituted with one to four substituents selected from the group consisting of halo, oxo, $C_1$-$C_6$-alkyl, $C_1$-$C_6$-haloalkyl, $C_1$-$C_6$-alkoxy, C(O)$NR^AR^B$, $C_1$-$C_6$-alkoxy, $C_6$-$C_{10}$-aryl (optionally substituted by one to three halo and $C_1$-$C_6$-alkyl), and 5- to 10-membered heteroaryl (wherein 1-4 heteroaryl members are independently selected from N, O, and S; optionally substituted by one to three substituents selected from $C_1$-$C_6$-alkyl and 5- to 10-membered heteroaryl).

$R^A$ and $R^B$ are independently selected from the group consisting of H, $C_1$-$C_6$-alkyl, $C_1$-$C_6$-haloalkyl, —$C_1$-$C_6$-alkyl-$C_6$-$C_{10}$-aryl, C(O)$C_1$-$C_6$-alkyl, C(O)$C_1$-$C_6$-alkyl-$C_6$-$C_{10}$-aryl, C(O)O$C_1$-$C_6$-alkyl, $C_6$-$C_{10}$-aryl (optionally fused to $C_3$-$C_{14}$-cycloalkyl that is optionally substituted by one to four halo and $C_1$-$C_6$-alkyl), wherein each aryl is optionally substituted with one to three substituents selected from $C_1$-$C_6$-alkyl, halo, hydroxy, $C_1$-$C_6$-haloalkyl, and 3- to 14-membered heterocycloalkyl (wherein 1-4 ring members are independently selected from N, O, and S); and wherein each alkyl is optionally substituted with one to three substituents selected from halo, NRR' (wherein R and R' are independently selected from H, $C_1$-$C_6$-alkyl, C(O)$C_1$-$C_6$-alkyl, and C(O)$C_6$-$C_{10}$-aryl).

$R^{1L}$ and $R^{2L}$ are independently selected from the group consisting of H, $C_1$-$C_6$-alkyl, $C_6$-$C_{10}$-aryl, —($C_1$-$C_6$-alkyl) $C_6$-$C_{10}$-aryl, 5-10-membered heteroaryl (wherein 1-4 heteroaryl ring members are independently selected from the group consisting of O, S, and N), and $C_3$-$C_{14}$-cycloalkyl, wherein each aryl is optionally substituted with one to three substituents independently selected from the group consisting of $C_1$-$C_6$-alkyl, halo, $C_1$-$C_6$-haloalkyl, and $C_1$-$C_6$-alkoxy.

Each instance of $R^{3L}$ and $R^{4L}$ is independently selected from the group consisting of $C_1$-$C_6$-alkyl, halo, $C_1$-$C_6$-alkoxy, and $C_1$-$C_6$-haloalkyl.

The subscript n is an integer selected from 1, 2, and 3. The subscript o is an integer selected from 0, 1, 2, and 3. The subscript p is an integer selected from 0, 1, 2, and 3.

In some embodiments,

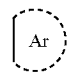

is an optionally substituted monocyclic ring. In other embodiments,

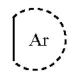

is an optionally substituted bicyclic ring system. In still other embodiments,

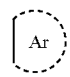

is an optionally substituted tricyclic ring system. Examples of

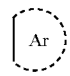

are selected from the group consisting of the following rings, optionally substituted:
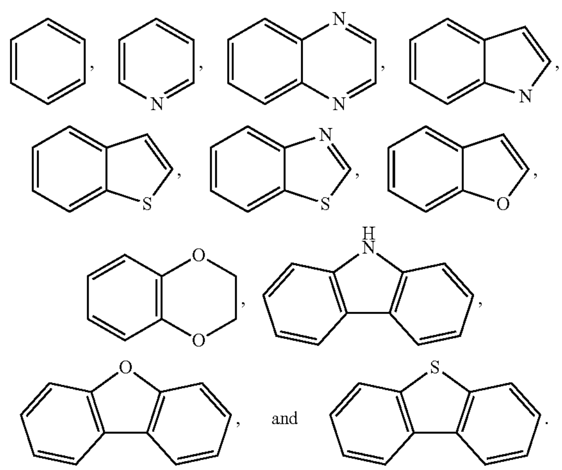
In some embodiments,
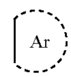
is optionally substituted
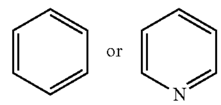
Embodiments illustrating various
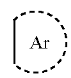
are in exemplary compounds of formula (1) shown in Table 1 below.
TABLE 1
| Examples of Formula (1) Compounds | | | |
|---|---|---|---|
| 1a | 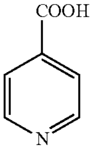 | 1ac | 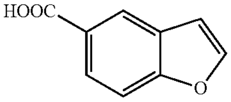 |
| 1b | 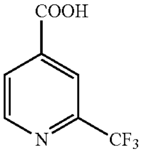 | 1ad | 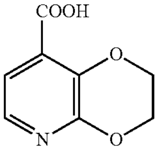 [SMILES: O=C(O)c1ccnc2c1OCCO2] |
| 1c | 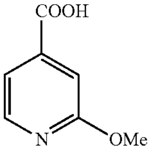 [SMILES: COc1cc(C(=O)O)ccn1] | 1ae | 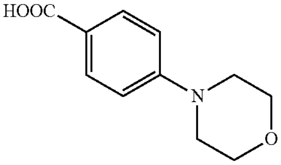 [SMILES: O=C(O)c1ccc(N2CCOCC2)cc1] |
| 1d | 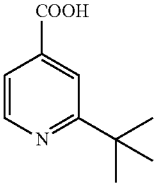 | 1af | 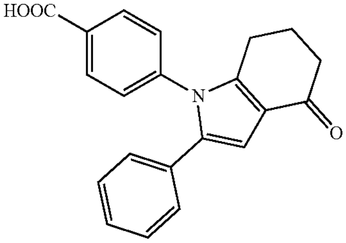 [SMILES: O=C(O)c1ccc(-n2c(-c3ccccc3)cc3c2CCCC3=O)cc1] |
| 1e | 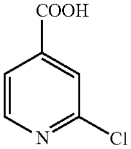 | 1ag | 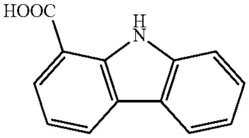 [SMILES: O=C(O)c1cccc2c1[nH]c1ccccc12] |

TABLE 1-continued
| Examples of Formula (1) Compounds | | | |
|---|---|---|---|
| 1f | 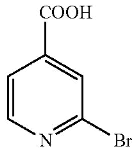 | 1ah | 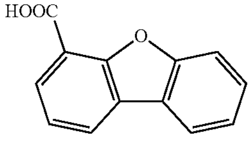 |
| 1g | 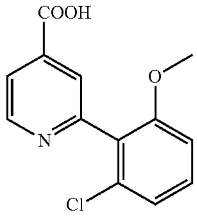 [SMILES: COc1cccc(Cl)c1-c1cc(C(=O)O)ccn1] | 1ai | 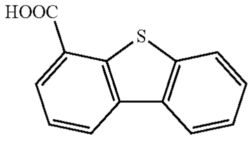 [SMILES: O=C(O)c1cccc2c1sc1ccccc12] |
| 1h | 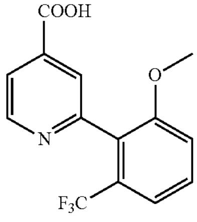 [SMILES: COc1cccc(C(F)(F)F)c1-c1cc(C(=O)O)ccn1] | 1aj | 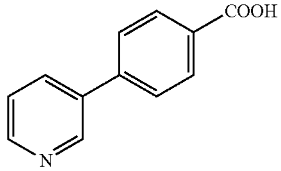 [SMILES: O=C(O)c1ccc(-c2cccnc2)cc1] |
| 1i | 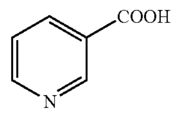 | 1ak | 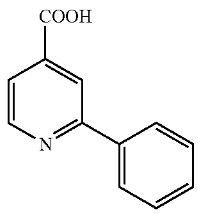 [SMILES: O=C(O)c1ccnc(-c2ccccc2)c1] |
| 1j | 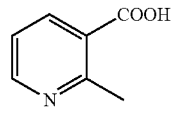 | 1al | 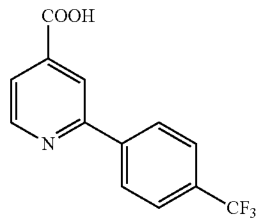 [SMILES: O=C(O)c1ccnc(-c2ccc(C(F)(F)F)cc2)c1] |
| 1k | 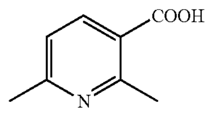 | 1am | 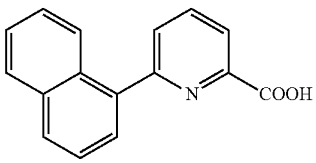 [SMILES: O=C(O)c1cccc(-c2cccc3ccccc23)n1] |
| 1l | 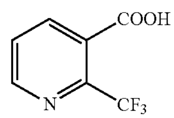 | 1an | 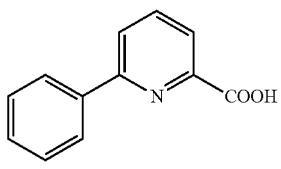 [SMILES: O=C(O)c1cccc(-c2ccccc2)n1] |
| 1m | 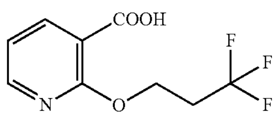 [SMILES: O=C(O)c1cccnc1OCCC(F)(F)F] | 1ao | 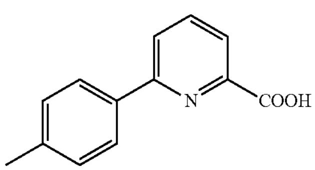 [SMILES: Cc1ccc(-c2cccc(C(=O)O)n2)cc1] |

TABLE 1-continued
| Examples of Formula (1) Compounds | | | |
|---|---|---|---|
| 1n | 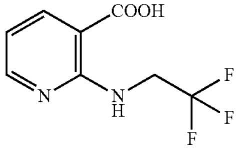 [SMILES: O=C(O)c1cccnc1NCC(F)(F)F] | 1ap | 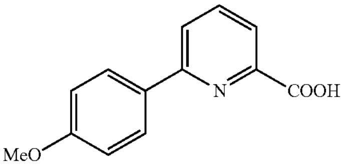 [SMILES: COc1ccc(-c2cccc(C(=O)O)n2)cc1] |
| 1o | 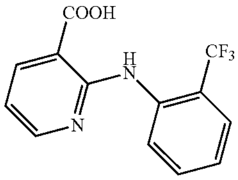 [SMILES: O=C(O)c1cccnc1Nc1ccccc1C(F)(F)F] | 1aq | 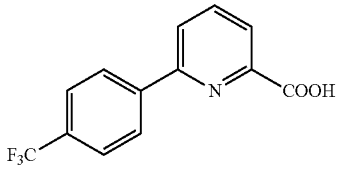 [SMILES: O=C(O)c1cccc(-c2ccc(C(F)(F)F)cc2)n1] |
| 1p | 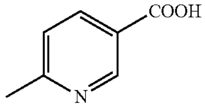 | 1ar | 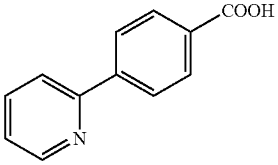 [SMILES: O=C(O)c1ccc(-c2ccccn2)cc1] |
| 1q | 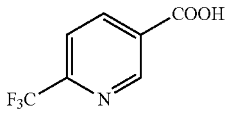 | 1as | 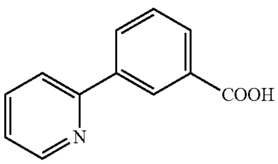 [SMILES: O=C(O)c1cccc(-c2ccccn2)c1] |
| 1r | 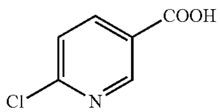 | 1at | 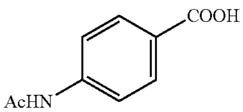 [SMILES: CC(=O)Nc1ccc(C(=O)O)cc1] |
| 1s | 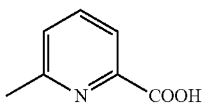 | 1au | 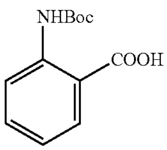 [SMILES: CC(C)(C)OC(=O)Nc1ccccc1C(=O)O] |
| 1t | 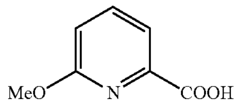 | 1av | 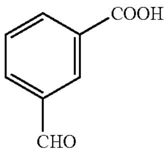 |
| 1u | 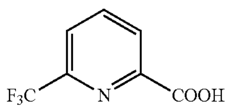 | 1aw | 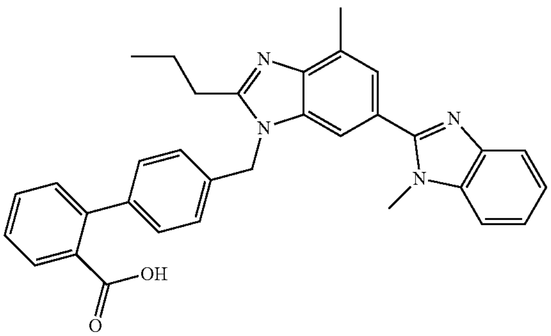 [SMILES: CCCc1nc2c(C)cc(-c3nc4ccccc4n3C)cc2n1Cc1ccc(-c2ccccc2C(=O)O)cc1] |

TABLE 1-continued
| Examples of Formula (1) Compounds | | | |
|---|---|---|---|
| 1v | 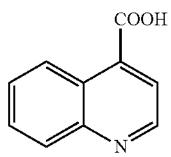 [SMILES: O=C(O)c1ccnc2ccccc12] | 1ax | 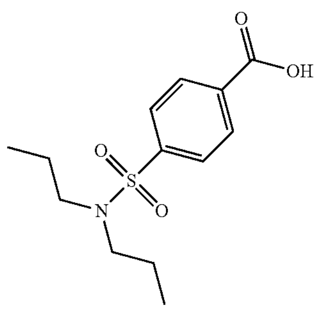 [SMILES: CCCN(CCC)S(=O)(=O)c1ccc(C(=O)O)cc1] |
| 1w | 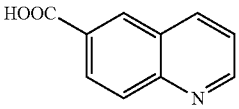 [SMILES: O=C(O)c1ccc2ncccc2c1] | 1ay | 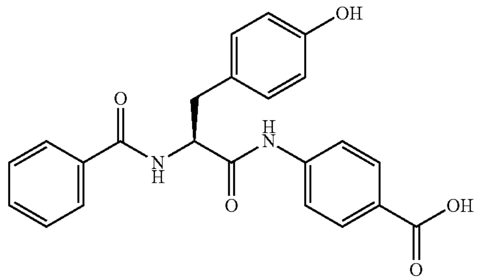 [SMILES: O=C(O)c1ccc(NC(=O)[C@H](Cc2ccc(O)cc2)NC(=O)c2ccccc2)cc1] |
| 1x | 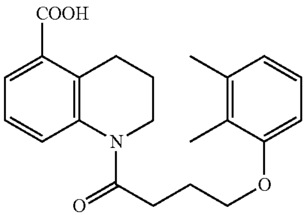 [SMILES: Cc1cccc(OCCCC(=O)N2CCCc3c(C(=O)O)cccc32)c1C] | 1az | 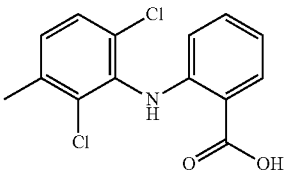 [SMILES: Cc1ccc(Cl)c(Nc2ccccc2C(=O)O)c1Cl] |
| 1y | 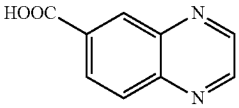 [SMILES: O=C(O)c1ccc2nccnc2c1] | 1ba | 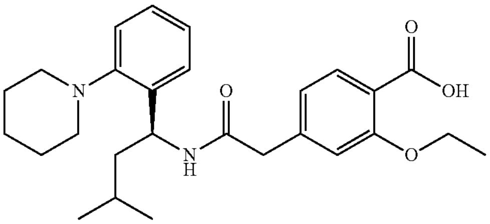 [SMILES: CCOc1cc(CC(=O)N[C@@H](CC(C)C)c2ccccc2N2CCCCC2)ccc1C(=O)O] |
| 1z | 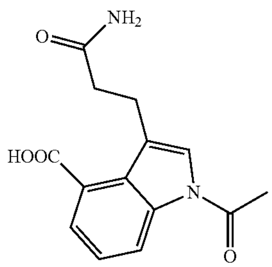 [SMILES: CC(=O)n1cc(CCC(N)=O)c2c(C(=O)O)cccc21] | 1bb | 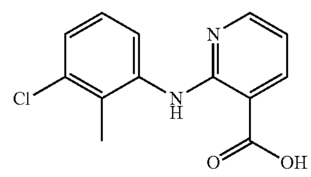 [SMILES: Cc1c(Cl)cccc1Nc1ncccc1C(=O)O] |
| 1aa | 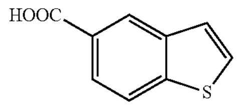 [SMILES: O=C(O)c1ccc2sccc2c1] | 1bc | 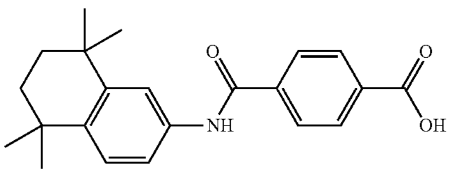 |

TABLE 1-continued

| Examples of Formula (1) Compounds | | | |
|---|---|---|---|
| 1ab | 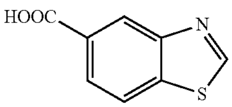 [SMILES: O=C(O)c1ccc2scnc2c1] | 1bd | 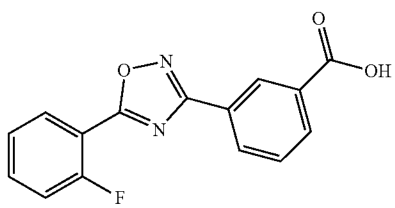 [SMILES: O=C(O)c1cccc(-c2noc(-c3ccccc3F)n2)c1] |

In some embodiments, n in formula (L) is 1 or 2. As illustrated by data disclosed herein, coordination of a ligand of formula (L) to a palladium facilitates at least a 6-membered (n is 1) or 7-membered (n is 2) chelate wherein the ligand (L) is advantageously bound more weakly to palladium than in a 5-membered chelate.

In various embodiments, $R^{1L}$ and $R^{2L}$ in formula (L) are independently selected from the group consisting of $C_1$-$C_6$-alkyl, $C_6$-$C_{10}$-aryl, and —($C_1$-$C_6$-alkyl)$C_6$-$C_{10}$-aryl. In some embodiments, the pyridone ring in formula (L) is substituted, wherein p is 1, 2, or 3. In other embodiments, the ring is unsubstituted, wherein p is 0.

In additional embodiments, the pyridine ring in formula (L) is substituted, wherein o is 1, 2, or 3. Examples of substitution include embodiments wherein $R^{3L}$ is independently $C_1$-$C_6$-alkyl or halo. In other embodiments, the ring is unsubstituted, wherein p is 0.

The amount of ligand of formula (L) can be adjusted, and it generally ranges from about 0.5 to about 15 mol %, about 5 to about 13 mol %, or about 7 to about 12 mol % (based on amount of compound of formula (1)). Illustrative amounts of a ligand of formula (L) include about 1, 2, 3, 4, 5, 6, 7, 8, 9, and 10 mol %. One typical amount, per an embodiment, is about 10 mol %.

Specific embodiments of the ligand of formula (L) are shown in Table 2 below.

TABLE 2

| Examples of ligand of formula (L). | |
|---|---|
| L26 | 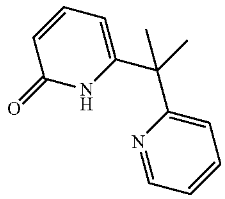 [SMILES: CC(C)(c1ccccn1)c1cccc(=O)[nH]1] |
| L27 | 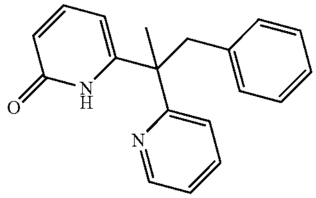 [SMILES: CC(Cc1ccccc1)(c1ccccn1)c1cccc(=O)[nH]1] |

TABLE 2-continued

| Examples of ligand of formula (L). | |
|---|---|
| L28 | 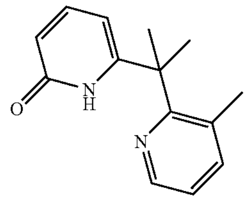 [SMILES: Cc1cccnc1C(C)(C)c1cccc(=O)[nH]1] |
| L29 | 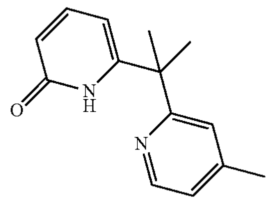 [SMILES: Cc1ccnc(C(C)(C)c2cccc(=O)[nH]2)c1] |
| L30 | 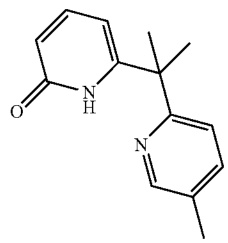 [SMILES: Cc1ccc(C(C)(C)c2cccc(=O)[nH]2)nc1] |
| L31 | 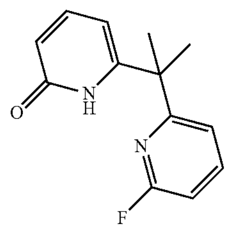 [SMILES: CC(C)(c1cccc(F)n1)c1cccc(=O)[nH]1] |
| L32 | 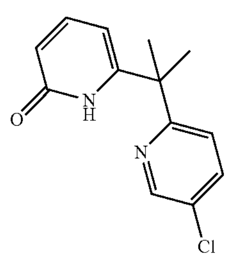 [SMILES: CC(C)(c1ccc(Cl)cn1)c1cccc(=O)[nH]1] |

TABLE 2-continued
| Examples of ligand of formula (L). | |
|---|---|
| L33 | 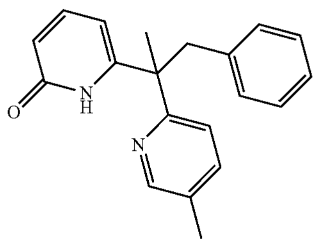 [SMILES: Cc1ccc(C(C)(Cc2ccccc2)c2cccc(=O)[nH]2)nc1] |
| L34 | 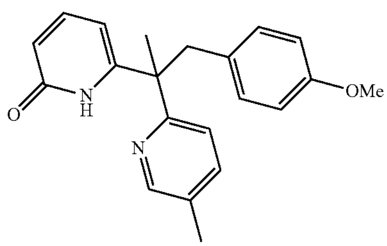 [SMILES: COc1ccc(CC(C)(c2ccc(C)cn2)c2cccc(=O)[nH]2)cc1] |
| L35 | 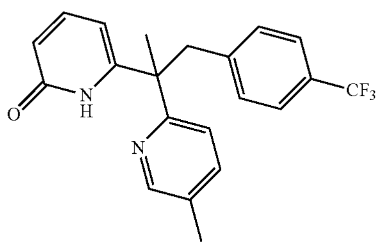 [SMILES: Cc1ccc(C(C)(Cc2ccc(C(F)(F)F)cc2)c2cccc(=O)[nH]2)nc1] |
| L36 | 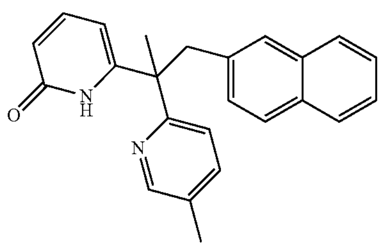 [SMILES: Cc1ccc(C(C)(Cc2ccc3ccccc3c2)c2cccc(=O)[nH]2)nc1] |
| L37 | 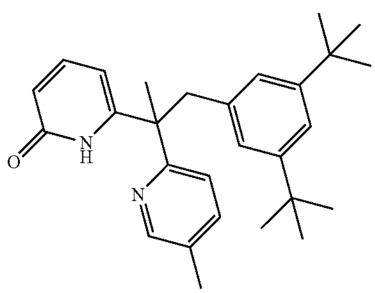 [SMILES: Cc1ccc(C(C)(Cc2cc(C(C)(C)C)cc(C(C)(C)C)c2)c2cccc(=O)[nH]2)nc1] |
| L38 | 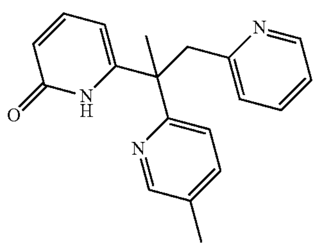 [SMILES: Cc1ccc(C(C)(Cc2ccccn2)c2cccc(=O)[nH]2)nc1] |
TABLE 2-continued
| Examples of ligand of formula (L). | |
|---|---|
| L39 | 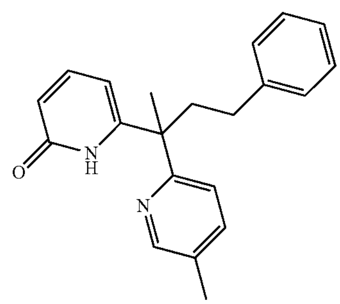 [SMILES: Cc1ccc(C(C)(CCc2ccccc2)c2cccc(=O)[nH]2)nc1] |
| L40 | 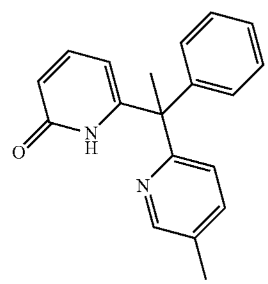 [SMILES: Cc1ccc(C(C)(c2ccccc2)c2cccc(=O)[nH]2)nc1] |
| L41 | 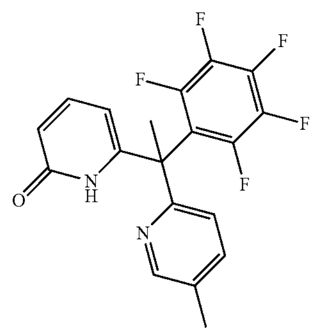 [SMILES: Cc1ccc(C(C)(c2cccc(=O)[nH]2)c2c(F)c(F)c(F)c(F)c2F)nc1] |
| L42 | 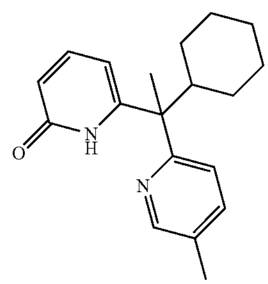 [SMILES: Cc1ccc(C(C)(c2cccc(=O)[nH]2)C2CCCCC2)nc1] |
| L43 | 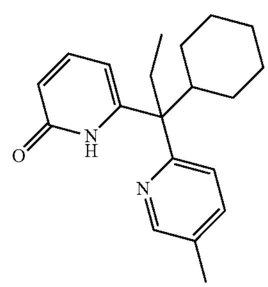 [SMILES: CCC(c1ccc(C)cn1)(c1cccc(=O)[nH]1)C1CCCCC1] |

TABLE 2-continued

| Examples of ligand of formula (L). |
| --- |
| L44 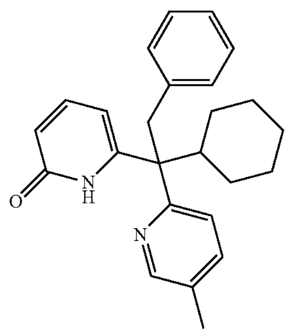 |
| L45 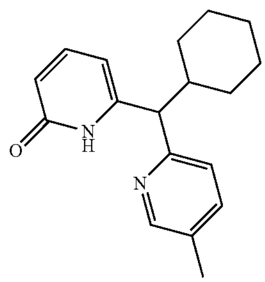 |

The process of the present disclosure occurs in the presence of a source of palladium (II). Various reagents available commercially or otherwise known to those skilled in the art are capable of supplying palladium (II), including those that generate palladium (II) in situ, such as from a palladium (0) compound. The process is amenable to direct and convenient sources of palladium (II), which include any palladium (II) salt. Illustrative palladium (II) salts include $Pd(OAc)_2$, (OAc=acetate), $Pd(TFA)_2$ (TFA=trifluoroacetate), $PdCl_2$, and $Pd(CH_3CN)_2Cl_2$. In a specific embodiment, the palladium (II) source is $Pd(OAc)_2$. The amount of Pd(II) can be adjusted, and generally ranges from about 0.5 to about 15 mol %, about 5 to about 13 mol %, or about 7 to about 12 mol % (based on amount of compound of formula (1)). Illustrative amounts of Pd(II) include about 1, 2, 3, 4, 5, 6, 7, 8, 9, and 10 mol %. One typical amount, per an embodiment, is about 10 mol %. In another embodiment, the amount of ligand of formula (L) and amount of Pd(II) source each is about 10 mol %.

One advantage of the process of the present disclosure resides in the use of $O_2$ at no particular pressure of $O_2$, although elevated pressures can be used. Thus, C—H activation and hydroxylation in accordance with the process proceeds, per an embodiment, in the presence of $O_2$ at about one atmosphere (atm). The $O_2$ can be pure or, in various embodiments, entrained in another gas or gas mixtures including nitrogen, argon, and air.

In various embodiments, the contacting step of the process further occurs in the presence of a non-nucleophilic base. Exemplary non-nucleophilic bases include inorganic bases, such as salts selected from the group consisting of KOAc, NaOAc, CsOAc, $K_3PO_4$, $K_2HPO_4$, $KH_2PO_4$, and $K_2CO_3$. In an embodiment, the non-nucleophilic base is KOAc. The amount of base can range from about 1 to about 10 equivalents. In one embodiment, the amount of base is about 2 equivalents.

In still further embodiments, the contacting of the process described herein occurs in the presence of a polar aprotic solvent. Various polar aprotic solvents are well-known to those skilled in the art of organic synthesis. Examples of polar aprotic solvents include N-methylpyrrolidine (NMP), dimethylacetamide (DMA), dimethylformamide (DMF), tetrahydrofuran (THF), acetone, acetonitrile, ethylacetate, hexamethylphosphoric triamide (HMPT), and dimethylsulfoxide (DMSO). In an illustrative embodiment, the solvent is DMF. The process described herein is amenable to various reaction temperatures. As a practical matter, suitable reaction rates and/or yields can be achieved at elevated temperatures, such as about 70, 80, 90, 100, 110, 120, or 130° C. The skilled person will select a polar aprotic solvent that facilitates the desired reaction temperature and pressure. In exemplary embodiments, the process is carried out in DMF at about 110° C.

In various embodiments, the contacting step of the process described herein further occurs in the presence of benzoquinone (BQ). While not necessary, addition of BQ can increase yield of the process. Amounts of BQ can range from about 0.1 to about 3.0 equivalents, about 0.3 to about 2.0 equivalents, and about 0.5 to about 1.5 equivalents. Exemplary amounts include about 0.3, 0.5, 0.7, 1.0, 1.3, 1.5, 2.0, 2.5, and 3.0 equivalents.

In additional embodiments, the ligand effect was examined through a wide range of pyridone ligands using an isonicotinic acid substrate that previously showed no reactivity under the ligand-less conditions. No desired product was observed with a wide range of pyridone ligands L1-L19 (Example 21, Table 4a). A variety of pyridine-pyridone ligands that form a five-membered chelation with Pd(II) were synthesized and tested under the standard conditions (L20-L25), yet still no C—H hydroxylation was observed (Example 21, Table 4b). Although L,L- or L,X-type coordination of these ligands are both feasible as shown by the synthesis of corresponding complexes,[18] we hypothesize without being bound to theory that the five-membered chelate which forms from the L,L-pyridine-pyridine mode is too stable to allow tautomerization into the L,X-pyridine-pyridone form that surprisingly facilitates the C—H cleavage in the process disclosed herein.

In contrast, the present ligand of formula (L), in various embodiments illustrated when n is 1, forms a less stable six-membered chelate so that the barrier to switch between L,L- and L,X-coordination modes is lowered (L26-L45). Surprisingly, ligand L33 afforded the desired ortho-hydroxylated product in 48% yield, demonstrating the feasibility of this ligand scaffold. Ligand optimization improved the yield to 72% (L42). The use of $^{18}O_2$ (97% purity) gave the desired product containing 95% $^{18}O$, supporting the proposed biomimetic hydroxylation pathway. To obtain evidence in support of using tautomerization as a ligand design principle, we employed IR to monitor the coordination mode of both L20 and L42 by titrating ligands into the solution of $Pd(OAc)_2$. The presence of a peak at 1639 $cm^{-1}$ with L42 is consistent with the pyridone binding motif, whereas the absence of the corresponding carbonyl signal suggests a predominant L,L-type pyridine-pyridine binding for five-membered counterpart L20.

In various embodiments, the process is amenable to a wide range of medicinally important heterocyclic benzoic acids (see Examples). For instance, isonicotinic acids containing electron-withdrawing (1b), electron-donating (1c, 1d) and halogen (1e, 1f) substituents are all reactive, affording the hydroxylated product at the less hindered position. Heterocyclic biaryl substrates (1g, 1h), which are common scaffolds in drug molecules, were also smoothly hydroxylated in high yields. Unsubstituted nicotinic acid gave a mixture of 2-hydroxynicotinic acid (2i, major) and 4-hydroxynicotinic acid (2i', minor). Formula (1) compounds 1j and 1k provided ortho-hydroxylation products selectively without any trace of benzylic C—H oxidation, rendering radical pathway unlikely. Various 2-substituted nicotinic acids afforded 4-hydroxylated products in high yield regardless of their electronic properties (2l to 2o). A surprising advantage of the process is illustrated by the fact that 2-alkylamino and 2-arylamino groups, often incompatible with C—H activation reactions due to their strong coordinating nature, were both well tolerated (2n, 2o). Further, 2- and 4-hydroxylated products were both obtained for 6-substituted nicotinic acids (2p to 2r). Picolinic acids (2s to 2u) were also compatible substrates for this reaction, affording corresponding 3-hydroxylpicolinic acids in high yields, which is an advantageous result because picolinic acids are usually unreactive substrates in C—H activation due to their bidentate chelation. The remarkable compatibility of the process with isonicontinic, isonicontinic and picolinic acids provides a highly versatile synthetic tool for synthesizing a wide range of medicinally valuable heterocycles.

To further explore the scope of this hydroxylation reaction, in additional embodiments, we evaluated other heterocyclic carboxylic acids in which the heteroatom and carboxyl group are on different aryl rings. Both quinolines and tetrahydoquinoline were compatible, affording hydroxylated products in good yields (2v to 2x). Indoles, often unstable under oxidizing conditions, were also tolerated under our reaction conditions (2y, 2z). Carboxylic acids featuring benzothiophene (2aa), benzothiazole (2ab), benzofuran (2ac), benzodioxane (2ad), morpholine (2ae), pyrrole (2af), carbazole (2ag), dibenzothiophene (2ah) and dibenzothiophene (2ai) structures were all successfully hydroxylated. Hydroxylation of medicinally important biaryl heterocyclic carboxylic acid (2aj) also gave the desired product in 68% yield (see Examples).

The surprising compatibility of the process with heterocycles without using a strong directing group prompted us to explore site selectivity in the presence of multiple directing groups. In this context, shifting the heterocycle-directed to simple carboxylic acid-directed C—H activation remains an unsolved challenge for Pd(II) catalysts. Because 2-pyridyl is considered as one of the strongest directing groups for $C(sp^2)$-H activation, we examined biaryl substrates in which the pyridyl nitrogen and carboxyl group are either on the same or different aryl rings. Remarkably, the weakly coordinating carboxyl group overpowered all pyridyl directing effect in the process. 2-aryl isonicotinic acids and 6-aryl picolinic acids consistently afforded carboxyl-directed hydroxylation product in 60-70% yields (2ak to 2aq). Different scaffolds with 2-pyridyl and carboxyl group on different rings also afford the site selectivity governed by the carboxyl group (2ar, 2as). The desired site selectivity was also obtained in the presence of a range of other commonly used native directing groups including —NHAc, —NHBoc and aldehyde (2at to 2av).

Late-stage modification of complex natural products and drug molecules by site selective C—H activation can be a powerful approach to rapidly optimize the bioactivity of lead compounds. Among the wide range of Pd-catalyzed C—H activation reactions, the lack of compatibility with heterocycles and site selectivity is a major practical obstacle in this approach. In light of the unique of importance of installing hydroxyl group to drug molecules, we subjected a number of commercial drugs to the process as described herein. For example, in one embodiment, the anti-hypertension drug Telmisartan (1aw) was ortho-hydroxylated in 60% yield. In some exemplary embodiments, Probenecid (1ax), Bentiromide (1ay), Meclofenamic acid (1az), Repaglinide (1ba), Clonixin (1bb), Tamibarotene (1bc) and Ataluren (1bd), were all successfully hydroxylated at their ortho positions with high efficiency. These derivatives are not only valuable for potentially repurposing medicine for different diseases, but are also useful for studying drug metabolism and pharmacokinetics.

Numbered references in the preceding sections are as follows:

1. Gröger, H. Hydroxy functionalization of non-activated C—H and C═C Bonds: New perspectives for the synthesis of alcohols through biocatalytic processes. *Angew. Chemie—Int. Ed.* 53, 3067-3069 (2014).
2. Guroff, G. et al. Hydroxylation-Induced Migration: The NIH Shift. *Science.* 157, 1524-1530 (1967).
3. Rostovtsev, V. V., Labinger, J. A., Bercaw, J. E., Lasseter, T. L. & Goldberg, K. I. Oxidation of dimethylplatinum(II) complexes with dioxygen. *Organometallics* 17, 4530-4531 (1998).
4. Denney, M. C., Smythe, N. A., Cetto, K. L., Kemp, R. A. & Goldberg, K. I. Insertion of molecular oxygen into a palladium(II) hydride bond. *J Am. Chem. Soc.* 128, 2508-2509 (2006).
5. Boisvert, L., Denney, M. C., Hanson, S. K. & Goldberg, K. I. Insertion of molecular oxygen into a palladium(II) methyl bond: A radical chain mechanism involving palladium(III) intermediates. *J Am. Chem. Soc.* 131, 15802-15814 (2009).
6. Zeitler, H. E., Kaminsky, W. A. & Goldberg, K. I. Insertion of Molecular Oxygen into the Metal-Methyl Bonds of Platinum(II) and Palladium(II) 1,3-Bis(2-pyridylimino)isoindolate Complexes. *Organometallics* 37, 3644-3648 (2018).
7. Tang, F., Zhang, Y., Rath, N. P. & Mirica, L. M. Detection of Pd(III) and Pd(IV) intermediates during the aerobic oxidative C—C bond formation from a Pd(II) dimethyl complex. *Organometallics* 31, 6690-6696 (2012).
8. Qu, F., Khusnutdinova, J. R., Rath, N. P. & Mirica, L. M. Dioxygen activation by an organometallic Pd(ii) precursor: formation of a Pd(iv)-OH complex and its C—O bond formation reactivity. *Chem. Commun.* 50, 3036-3039 (2014).
9. Rostovtsev, V. V., Henling, L. M., Labinger, J. A. & Bercaw, J. E. Structural and mechanistic investigations of the oxidation of dimethylplatinum(II) complexes by dioxygen. *Inorg. Chem.* 41, 3608-3619 (2002).
10. Dennig, A., Lülsdorf, N., Liu, H. & Schwaneberg, U. Regioselective o-hydroxylation of monosubstituted benzenes by P450 BM3. *Angew. Chemie—Int. Ed.* 52, 8459-8462 (2013).
11. Taktak, S., Flook, M., Foxman, B. M., Que, L. & Rybak-Akimova, E. V. ortho-Hydroxylation of benzoic acids with hydrogen peroxide at a non-heme iron center. *Chem. Commun.* 5301-5303 (2005).
12. Shilov, A. E. & Shul'pin, G. B. Activation of C—H bonds by metal complexes. Chem. Rev. 97, 2879-2932 (1997).
13. Ten Brink, G. J., Arends, I. W. C. E. & Sheldon, R. A. Green, catalytic oxidation of alcohols in water. *Science.* 287, 1636-1639 (2000).
14. Piera, J. & Bdckvall, J. E. Catalytic oxidation of organic substrates by molecular oxygen and hydrogen peroxide by multistep electron transfer—A biomimetic approach. *Angew. Chemie—Int. Ed.* 47, 3506-3523 (2008).
15. Wang, D., Zavalij, P. Y. & Vedernikov, A. N. Aerobic C—H acetoxylation of 8-methylquinoline in PdII-pyridinecarboxylic acid systems: Some structure-reactivity relationships. *Organometallics* 32, 4882-4891 (2013).

16. Zhang, Y. H. & Yu, J. Q. Pd(II)-catalyzed hydroxylation of arenes with 1 atm of $O_2$ or air. *J. Am. Chem. Soc.* 131, 14654-14655 (2009).
17. Wang, P. et al. Ligand-accelerated non-directed C—H functionalization of arenes. *Nature* 551, 489-493 (2017).
18. Salamanca, V., Toledo, A. & Albeniz, A. C. [2,2'-bipyridin]-6(1H)-one, a Truly Cooperating Ligand in the Palladium-Mediated C—H Activation Step: Experimental Evidence in the Direct C—3 Arylation of Pyridine. *J Am. Chem. Soc.* 140, 17851-17856 (2018).

EXAMPLES

Additional embodiments of the present disclosure are set forth in the following non-limiting examples.

General Information. $Pd(OAc)_2$ was purchased from Strem. 1,4-benzoquinone (BQ) was used after sublimation in a pure state. Solvents were obtained from Sigma-Aldrich, Alfa-Aesar, and Acros, and used directly without further purification. Other reagents were purchased at the highest commercial quality and used without further purification, unless otherwise stated. Analytical thin layer chromatography was performed on 0.25 mm silica gel 60-F254 or Merck pre-coated aluminium-backed silica gel F254 plates. $^1H$ NMR spectra were recorded on Bruker AMX-400 or Bruker DRX-600 instruments. The following abbreviations (or combinations thereof) were used to explain multiplicities: s=singlet, d=doublet, t=triplet, q=quartet, m=multiplet, br=broad. Coupling constants, J, were reported in Hertz unit (Hz). $^{13}C$ NMR spectra were recorded on Bruker DRX-600 and were fully decoupled by broad band proton decoupling. $^{19}F$ NMR Spectra were recorded on Bruker AMX-400 spectrometer (376 MHz) and were fully decoupled by broad band proton decoupling. Chemical shifts were referenced to the appropriate residual solvent peaks[1]. Column chromatography was performed using E. Merck silica (60, particle size 0.043-0.063 mm), and pTLC was performed on Merck silica plates (60F-254). Reversed-phase chromatography was carried out automated using Biotage Isolera™ one both ZIP and SNAP type cartridges and their $C_{18}$ counterparts. High-resolution mass spectra (HRMS) were recorded on an Agilent Mass spectrometer using ESI-TOF (electrospray ionization-time of flight). FT-IR analysis was performed using a Mettler-Toledo ReactIR™ 45 m instrument fitted with a DST 6.35 m Dicomp ATR probe.

Preparation of Aromatic and Heteroaromatic Carboxylic Acids. The following examples describe procurement and synthesis of compounds of formula (1).

Compounds 1g, 1h, 1m-1o, 1x-1z, 1af, 1ag, 1ai, 1az-1bc were obtained from the Bristol-Myers Squibb compounds collection. Other compounds were obtained from the commercial sources. Compounds 1al, 1am, 1ao-1aq were prepared by the following general procedure:

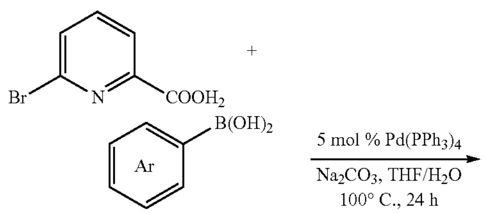

-continued

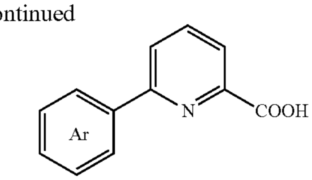

A Schlenk flask containing a magnetic rod was charged with $Pd(PPh_3)_4$ (87.9 mg, 0.125 mmol, 5 mol %), 2-bromopyridinecaboxylic acids (507 mg, 3.0 mmol), Phenylboronic acid (604 mg, 4.5 mmol, 1.5 equiv.), $Na_2CO_3$ (3180 mg, 30.0 mmol, 10.0 equiv.), evacuated and backfilled with nitrogen three times. Then THF (15 mL) and water (30 mL) was added. The reaction mixture was stirred at 100° C. for 24 h. After the reaction, the mixture was filtered and concentrated to remove the THF. The water phase extracted twice with DCM, and the organic phase was discarded. The mixture was acidified to pH<3 with the addition of 1.0 N HCl, and the resulting precipitate was collected by filtration, rinsed with ice-cold water, and dried to get the crude product. The crude product was then purified by reverse phase column-chromatography (40%-100% MeCN: $H_2O$) using Biotage Isolera™ one to afford the pure product after evaporation to dryness.

Example 1: 2-(4-(Trifluoromethyl)phenyl)isonicotinic acid (1al)

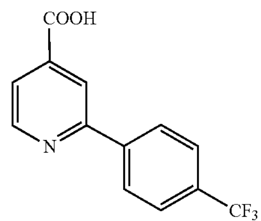 [SMILES: O=C(O)c1ccnc(-c2ccc(C(F)(F)F)cc2)c1]

White solid, 0.360 g, 45% yield. $^1H$ NMR (600 MHz, DMSO-$d_6$) δ 8.90 (d, J=4.9 Hz, 1H), 8.38 (s, 1H), 8.34 (d, J=8.1 Hz, 2H), 7.89-7.82 (m, 3H). $^{13}C$ NMR (151 MHz, DMSO-$d_6$) δ 166.09, 155.50, 150.93, 141.72, 139.84, 129.58 (q, $J_{CF}$=31.4 Hz), 127.52, 125.80 (q, $J_{CF}$=3.9 Hz), 124.24 (q, $J_{CF}$=270.5 Hz), 122.48, 119.74.

Example 2: 6-(Naphthalen-1-yl)picolinic acid (1am)

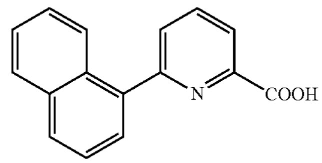 [SMILES: O=C(O)c1cccc(-c2cccc3ccccc23)n1]

White solid, 0.545 g, 73% yield. $^1H$ NMR (600 MHz, DMSO-$d_6$) δ 8.08-7.98 (m, 5H), 7.73 (dd, J=6.4, 2.4 Hz, 1H), 7.67-7.60 (m, 2H), 7.55 (dd, J=8.1, 6.7 Hz, 1H), 7.50 (dd, J=8.3, 6.7 Hz, 1H). $^{13}C$ NMR (151 MHz, DMSO-$d_6$) δ 167.51, 157.67, 152.24, 137.88, 137.58, 133.42, 130.62, 128.75, 128.32, 127.58, 126.64, 126.58, 125.98, 125.45, 125.33, 122.72.

Example 3: 6-(p-Tolyl)picolinic acid (1ao)

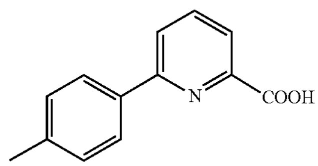 [SMILES: Cc1ccc(-c2cccc(C(=O)O)n2)cc1]

White solid, 0.480 g, 75% yield. $^1$H NMR (600 MHz, DMSO-$d_6$) δ 8.16 (dd, J=8.0, 1.4 Hz, 1H), 8.09 (d, J=8.1 Hz, 2H), 8.03 (t, J=7.8 Hz, 1H), 7.96 (d, J=7.6 Hz, 1H), 7.33 (d, J=7.8 Hz, 2H), 2.37 (s, 3H). $^{13}$C NMR (151 MHz, DMSO-$d_6$) δ 166.23, 155.97, 148.17, 139.19, 138.51, 135.00, 129.41, 126.78, 122.98, 122.92, 20.87.

Example 4: 6-(4-Methoxyphenyl)picolinic acid (1ap)

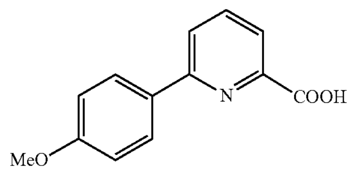 [SMILES: COc1ccc(-c2cccc(C(=O)O)n2)cc1]

White solid, 0.563 g, 82% yield. $^1$H NMR (600 MHz, DMSO-$d_6$) δ 8.14 (d, J=8.8 Hz, 2H), 8.11 (d, J=8.0 Hz, 1H), 7.99 (s, 1H), 7.90 (d, J=7.6 Hz, 1H), 7.05 (d, J=8.9 Hz, 2H), 3.81 (s, 3H).$^{13}$C NMR (151 MHz, DMSO-$d_6$) δ 166.26, 160.53, 155.76, 148.07, 138.42, 130.21, 128.32, 122.54, 122.39, 114.17, 55.28.

Example 5: 6-(4-(Trifluoromethyl)phenyl)picolinic acid (1aq)

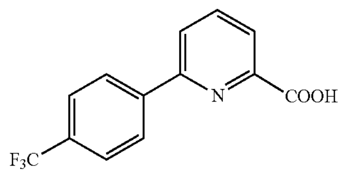 [SMILES: O=C(O)c1cccc(-c2ccc(C(F)(F)F)cc2)n1]

White solid, 0.441 g, 55% yield. $^1$H NMR (600 MHz, DMSO-$d_6$) δ 8.41 (d, J=8.2 Hz, 2H), 8.31 (d, J=7.9 Hz, 1H), 8.13 (t, J=7.8 Hz, 1H), 8.07 (d, J=7.7 Hz, 1H), 7.89 (d, J=8.2 Hz, 2H). $^{13}$C NMR (151 MHz, DMSO-$d_6$) δ 166.02, 154.35, 148.55, 141.58, 138.97, 129.59 (q, $J_{CF}$=31.8 Hz), 127.65, 125.73 (q, $J_{CF}$=3.9 Hz), 124.25 (q, $J_{CF}$=270.5 Hz), 124.14, 124.04.

Preparation of Bidentate Pyridine-Pyridone Ligands

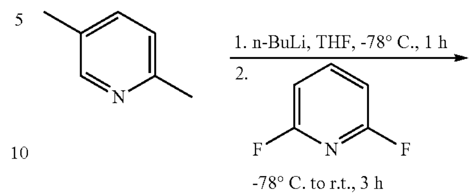

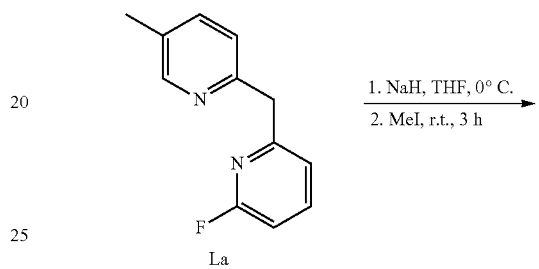

La

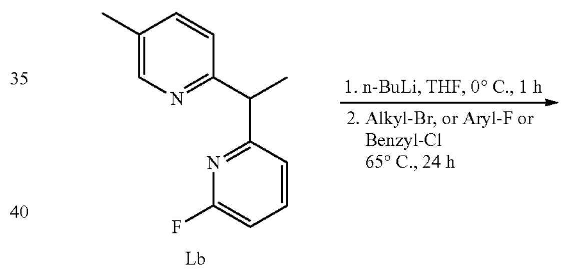

Lb

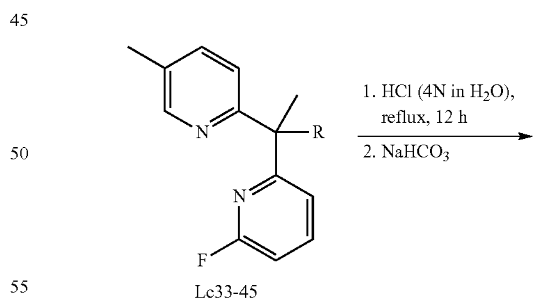

Lc33-45

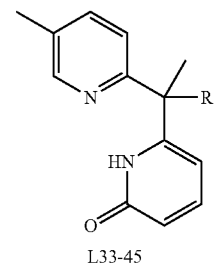

L33-45

Example 6: Synthesis of 2-(1-(6-Fluoropyridin-2-yl) ethyl)-5-methylpyridine (Lb)

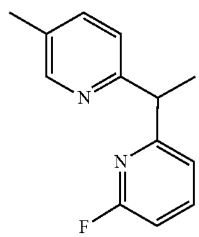 [SMILES: Cc1ccc(C(C)c2cccc(F)n2)nc1]

To a solution of 2,5-lutidine (4.289 g, 40 mmol, 2.0 equiv.) in anhydrous THF (80 mL) at −78° C. was added n-butyllithium (2.5 M in hexanes, 40 mmol, 16.0 mL, 2.0 equiv.) dropwise. The resulting solution was stirred for one hours at −78° C. before 2,6-difluoropyridine (2.30 g, 20 mmol, 1.0 equiv.) was added in a single batch. The resulting solution was allowed to warm to room temperature gradually and stirred for 3 hours, and then treated with saturated aqueous $NH_4Cl$ solution. The resulting mixture was extracted with ethyl acetate. The combined extracts were washed with brine, dried over anhydrous $Na_2SO_4$, and concentrated under vacuum. The resulting crude material La was used in the next step without further purification.

To a solution of La in anhydrous THF (30 mL) at 0° C. was added NaH (1.20 g, 30 mmol, 1.5 equiv.). The resulting solution was stirred for 1 h at 0° C. before MeI (1.9 mL, 30 mmol, 1.5 equiv.) was added dropwise. The resulting solution was allowed to warm to room temperature gradually and stirred for 5 hours. The reaction was quenched by aqueous saturated aqueous $NH_4Cl$ solution. The product was extracted with dichloromethane. The combined extracts were washed with brine, dried over anhydrous $Na_2SO_4$, and concentrated under vacuum. Flash chromatography (eluent: ethyl acetate/hexanes=1/6 to 1/2) gave Lb (Dark Red liquid, 1.99 g, 46% yield over two steps).

$^1$H NMR (600 MHz, $CDCl_3$) δ 8.35 (d, J=2.5 Hz, 1H), 7.69-7.61 (m, 1H), 7.41 (dd, J=8.1, 2.4 Hz, 1H), 7.20 (d, J=8.0 Hz, 1H), 7.12 (dd, J=7.5, 2.1 Hz, 1H), 6.71 (dd, J=8.2, 2.6 Hz, 1H), 4.34 (q, J=7.2 Hz, 1H), 2.27 (s, 3H), 1.70 (d, J=7.3 Hz, 3H). $^{13}$C NMR (151 MHz, $CDCl_3$) δ 163.42 (d, $J_{CF}$=12.6 Hz), 163.14 (d, $J_{CF}$=236.9 Hz), 160.31, 149.66, 141.42 (d, $J_{CF}$=7.7 Hz), 137.33, 131.11, 121.98, 119.63, 106.93 (d, $J_{CF}$=36.9 Hz), 48.86, 19.73, 18.15.

Synthesis of Ligands L33-L45. To a solution of Lb (216 mg, 1.0 mmol, 1.0 equiv.) in anhydrous THF (15 mL) at 0° C. was added n-butyllithium (2.5 M in hexanes, 1.5 mmol, 0.6 mL, 1.5 equiv.) dropwise. The resulting solution was stirred for 1 hour at 0° C. before Alkyl-Br or Aryl-F or Benzyl-Cl (3.0 mmol, 3.0 equiv.) was added. The resulting solution was heated to 65° C. and stirred overnight. The reaction was cooled down and then treated with saturated aqueous $NH_4Cl$ solution. The product was extracted with dichloromethane. The combined extracts were washed with brine, dried over anhydrous $Na_2SO_4$, and concentrated under vacuum. Flash chromatography (eluent: ethyl acetate/hexanes=1/6 to 1/3) gave Lc33-45.

A suspension of Lc33-45 in 4N HCl in water (20 mL) was refluxed for 12 hours, cooled down and concentrated under vacuum. The resulting solution was then quenched with saturated aqueous $NaHCO_3$ solution to neutral pH. The product was extracted with dichloromethane. The combined extracts were washed with brine, dried over anhydrous $Na_2SO_4$, and concentrated under vacuum. Flash chromatography (eluent: ethyl acetate/methanol=10/1 to 5/1) gave L33-L45. The yields were calculated over two steps.

Example 7: 2-(1-Cyclohexyl-1-(6-fluoropyridin-2-yl)ethyl)-5-methylpyridine (Lc42)

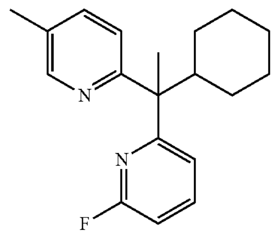 [SMILES: Cc1ccc(C(C)(c2cccc(F)n2)C2CCCCC2)nc1]

White solid, 0.193 g, 65% yield. $^1$H NMR (600 MHz, $CDCl_3$) δ 8.35 (s, 1H), 7.65-7.58 (m, 1H), 7.36 (s, 2H), 7.30 (dd, J=7.6, 3.1 Hz, 1H), 6.65 (dd, J=8.0, 3.3 Hz, 1H), 2.81 (td, J=11.9, 2.7 Hz, 1H), 2.25 (s, 3H), 1.74 (s, 3H), 1.66 (d, J=12.1 Hz, 3H), 1.37-1.26 (m, 4H), 1.11-1.08 (m, 1H), 1.06-0.95 (m, 2H). $^{13}$C NMR (151 MHz, $CDCl_3$) δ 165.94 (d, $J_{CF}$=12.2 Hz), 162.54 (d, $J_{CF}$=233.0 Hz), 162.33, 148.82, 140.73 (d, $J_{CF}$=8.7 Hz), 136.68, 130.17, 121.87, 119.64 (d, $J_{CF}$=6.0 Hz), 106.09 (d, $J_{CF}$=37.5 Hz), 53.56, 45.85, 28.48, 28.38, 27.14, 26.94, 18.37, 18.03.

Example 8: 6-(2-(5-Methylpyridin-2-yl)-1-phenylpropan-2-yl)pyridin-2(1H)-one (L33)

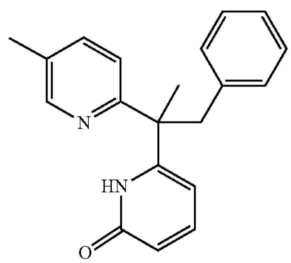 [SMILES: Cc1ccc(C(C)(Cc2ccccc2)c2cccc(=O)[nH]2)nc1]

White solid, 0.219 g, 72% yield. $^1$H NMR (600 MHz, $CDCl_3$) δ 11.26 (brs, 1H), 8.59 (s, 1H), 7.45 (dd, J=8.2, 2.3 Hz, 1H), 7.24 (dd, J=9.2, 7.0 Hz, 1H), 7.16-7.10 (m, 4H), 6.75 (d, J=7.8 Hz, 2H), 6.40 (d, J=9.2 Hz, 1H), 5.96 (d, J=6.9, 1H), 3.45-3.34 (m, 2H), 2.35 (s, 3H), 1.57 (s, 3H). $^{13}$C NMR (151 MHz, $CDCl_3$) δ 163.79, 159.32, 151.90, 149.51, 140.67, 137.87, 136.95, 132.14, 130.33, 127.95, 126.75, 120.64, 118.77, 102.91, 48.91, 46.48, 21.12, 18.15.

Example 9: 6-(1-(4-Methoxyphenyl)-2-(5-methylpyridin-2-yl)propan-2-yl)pyridin-2(1H)-one (L34)

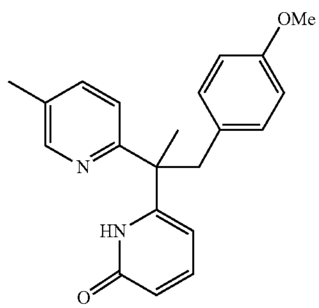 [SMILES: COc1ccc(CC(C)(c2ccc(C)cn2)c2cccc(=O)[nH]2)cc1]

White solid, 0.250 g, 75% yield. $^1$H NMR (600 MHz, $CDCl_3$) δ 11.26 (brs, 1H), 8.59 (d, J=1.8 Hz 1H), 7.45 (dd, J=8.2, 2.4 Hz, 1H), 7.24 (dd, J=9.1, 7.0 Hz, 1H), 7.15 (d, J=8.1 Hz, 1H), 6.66 (s, 4H), 6.40 (d, J=9.1 Hz 1H), 5.97 (d, J=7.0 Hz, 1H), 3.73 (s, 3H), 3.39-3.28 (m, 2H), 2.35 (s, 3H), 1.57 (s, 3H). $^{13}$C NMR (151 MHz, $CDCl_3$) δ 163.81, 159.40, 158.40, 152.03, 149.47, 140.71, 137.86, 132.04, 131.27, 128.94, 120.67, 118.66, 113.34, 102.97, 55.26, 48.16, 46.58, 21.07, 18.14.

Example 10: 6-(2-(5-Methylpyridin-2-yl)-1-(4-(trifluoromethyl)phenyl)propan-2-yl)pyridin-2(1H)-one (L35)

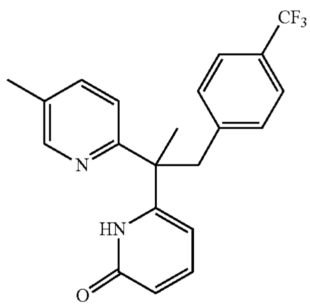 [SMILES: Cc1ccc(C(C)(Cc2ccc(C(F)(F)F)cc2)c2cccc(=O)[nH]2)nc1]

White solid, 0.234 g, 63% yield. $^1$H NMR (600 MHz, $CDCl_3$) δ 11.24 (s, 1H), 8.60 (d, J=2.4 Hz, 1H), 7.49-7.46 (m, 1H), 7.38 (d, J=8.0 Hz, 2H), 7.28-7.22 (m, 1H), 7.15 (d, J=8.1 Hz, 1H), 6.86 (d, J=7.9 Hz, 2H), 6.41 (d, J=9.1 Hz, 1H), 5.96 (d, J=7.0 Hz, 1H), 3.46 (d, J=1.3 Hz, 2H), 2.37 (s, 3H), 1.57 (s, 3H). $^{13}$C NMR (151 MHz, $CDCl_3$) δ 163.74, 158.76, 151.33, 149.60, 141.14, 140.67, 138.09, 132.47, 130.58, 129.11 (q, $J_{CF}$=26.8 Hz), 124.89 (q, $J_{CF}$=3.9 Hz), 124.29 (q, $J_{CF}$=270.3 Hz), 120.71, 119.09, 102.88, 48.46, 46.32, 21.03, 18.15. $^{19}$F NMR (376 MHz, $CDCl_3$) δ −65.13.

Example 11: 6-(2-(5-Methylpyridin-2-yl)-1-(naphthalen-2-yl)propan-2-yl)pyridin-2(1H)-one (L36)

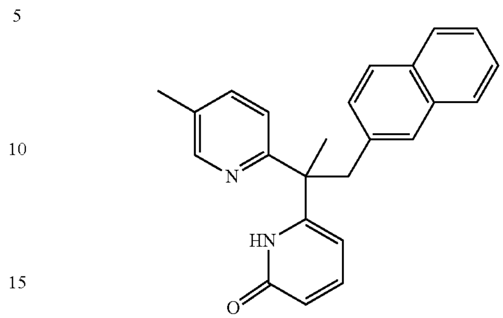

White solid, 0.173 g, 49% yield. $^1$H NMR (600 MHz, $CDCl_3$) δ 11.31 (brs, 1H), 8.64 (d, J=1.4 Hz, 1H), 7.76-7.73 (m, 1H), 7.67-7.62 (m, 1H), 7.58 (d, J=8.4 Hz, 1H), 7.46 (dd, J=8.1, 2.4 Hz, 1H), 7.43-7.39 (m, 2H), 7.25 (d, J=1.7 Hz, 1H), 7.22 (dd, J=9.2, 7.0 Hz, 1H), 7.16 (d, J=8.1 Hz, 1H), 6.81 (dd, J=8.4, 1.8 Hz, 1H), 6.43 (d, J=9.2 Hz, 1H), 5.94 (d, J=6.9 Hz, 1H), 3.62 (d, J=13.4 Hz, 1H), 3.51 (d, J=13.4 Hz, 1H), 2.38 (s, 3H), 1.61 (s, 4H). $^{13}$C NMR (151 MHz, $CDCl_3$) δ 163.85, 159.36, 151.82, 149.55, 140.70, 137.95, 134.58, 133.18, 132.35, 132.23, 129.13, 128.52, 127.73, 127.61, 127.35, 126.03, 125.71, 120.68, 118.82, 103.08, 49.10, 46.63, 21.18, 18.16.

Example 12: 6-(1-(3,5-Di-t-butylphenyl)-2-(5-methylpyridin-2-yl)propan-2-yl)pyridin-2(1H)-one (L37)

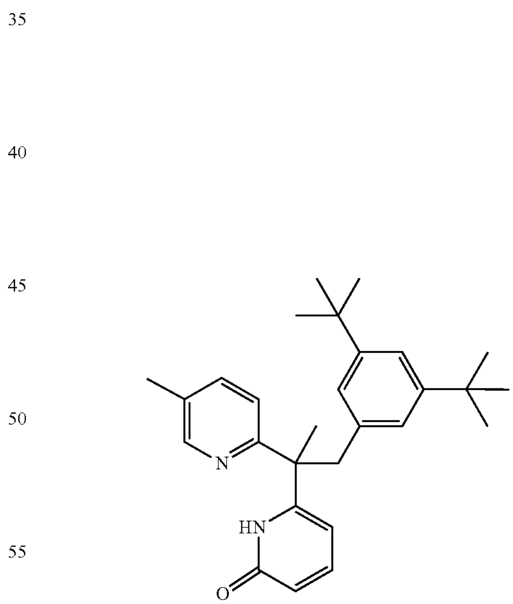

White solid, 0.287 g, 69% yield. $^1$H NMR (600 MHz, $CDCl_3$) δ 11.38 (s, 1H), 8.60 (d, J=2.3 Hz, 1H), 7.43 (dd, J=8.2, 2.4 Hz, 1H), 7.27-7.23 (m, 1H), 7.18 (t, J=1.8 Hz, 1H), 7.13 (d, J=8.1 Hz, 1H), 6.56 (d, J=1.8 Hz, 2H), 6.41 (d, J=9.1 Hz, 1H), 5.99 (d, J=7.0 Hz, 1H), 3.37 (s, 2H), 2.34 (s, 3H), 1.56 (s, 3H), 1.18 (s, 18H). $^{13}$C NMR (151 MHz, $CDCl_3$) δ 163.83, 159.56, 152.30, 150.10, 149.38, 140.75, 137.75, 135.75, 132.03, 124.66, 120.76, 120.39, 118.61, 102.94, 49.62, 46.58, 34.70, 31.49, 21.13, 18.07.

Example 13: 6-(2-(5-Methylpyridin-2-yl)-1-(pyridin-2-yl)propan-2-yl)pyridin-2(1H)-one (L38)

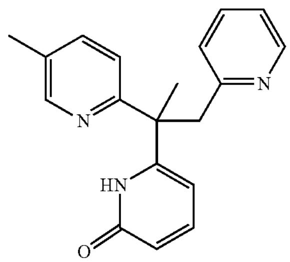 [SMILES: Cc1ccc(C(C)(Cc2ccccn2)c2cccc(=O)[nH]2)nc1]

White solid, 0.119 g, 39% yield. $^{1}$H NMR (600 MHz, $CDCl_3$) δ 11.96 (brs, 1H), 8.49 (d, J=2.4 Hz, 1H), 8.48 (d, J=4.9 Hz, 1H), 7.41 (td, J=7.6, 1.8 Hz, 2H), 7.27-7.20 (m, 1H), 7.10 (d, J=8.9 Hz, 1H), 7.06 (dd, J=7.5, 4.9 Hz, 1H), 6.71 (d, J=7.9 Hz, 1H), 6.40 (d, J=10.1 Hz, 1H), 5.96 (d, J=8.0 Hz, 1H), 3.69 (d, J=13.7 Hz, 1H), 3.50 (d, J=13.6 Hz, 1H), 2.32 (s, 3H), 1.71 (s, 3H). $^{13}$C NMR (151 MHz, $CDCl_3$) δ 164.09, 159.74, 157.70, 152.32, 149.46, 148.64, 140.67, 137.75, 136.23, 131.88, 124.74, 121.72, 120.77, 118.75, 103.21, 50.07, 47.27, 23.06, 18.13.

Example 14: 6-(2-(5-Methylpyridin-2-yl)-4-phenylbutan-2-yl)pyridin-2(1H)-one (L39)

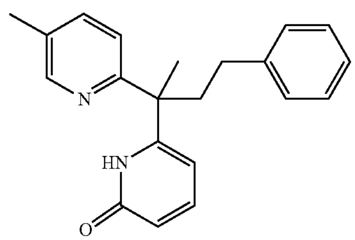 [SMILES: Cc1ccc(C(C)(CCc2ccccc2)c2cccc(=O)[nH]2)nc1]

White solid, 0.206 g, 65% yield. $^{1}$H NMR (600 MHz, $CDCl_3$) δ 10.80 (s, 1H), 8.61 (s, 1H), 7.58 (d, J=8.2 Hz, 1H), 7.42 (dd, J=9.0, 7.0 Hz, 1H), 7.37-7.31 (m, 3H), 7.26 (dd, J=7.4, 1.6 Hz, 1H), 7.19 (d, J=8.3 Hz, 2H), 6.47 (d, J=8.9 Hz, 1H), 6.30 (d, J=6.8 Hz, 1H), 2.68-2.38 (m, 4H), 2.42 (s, 3H), 1.90 (s, 3H). $^{13}$C NMR (151 MHz, $CDCl_3$) δ 163.77, 159.31, 152.57, 149.77, 141.59, 140.76, 137.80, 131.96, 128.40, 128.39, 126.10, 120.45, 118.65, 102.30, 46.00, 44.42, 31.12, 21.68, 18.09.

Example 15: 6-(1-(5-Methylpyridin-2-yl)-1-phenylethyl)pyridin-2(1H)-one (L40)

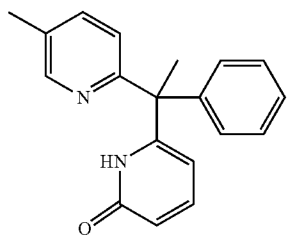 [SMILES: Cc1ccc(C(C)(c2ccccc2)c2cccc(=O)[nH]2)nc1]

White solid, 0.148 g, 51% yield. $^{1}$H NMR (600 MHz, $CDCl_3$) δ 10.97 (brs, 1H), 8.48 (d, J=2.3 Hz, 1H), 7.50 (dd, J=8.2, 2.3 Hz, 1H), 7.35 (dd, J=9.2, 7.0 Hz, 1H), 7.28-7.21 (m, 4H), 6.89 (d, J=7.3 Hz, 2H), 6.44 (d, J=9.2 Hz, 1H), 6.17 (d, J=7.0 Hz, 1H), 2.34 (s, 3H), 2.01 (s, 3H). $^{13}$C NMR (151 MHz, $CDCl_3$) δ 163.57, 160.13, 152.19, 149.69, 146.89, 140.49, 137.61, 132.06, 128.58, 127.98, 127.08, 121.51, 119.14, 104.45, 52.17, 28.11, 18.15.

Example 16: 6-(1-(5-Methylpyridin-2-yl)-1-(perfluorophenyl)ethyl)pyridin-2(1H)-one (L41)

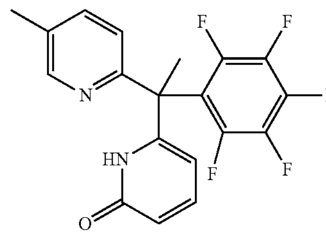

White solid, 0.133 g, 35% yield. $^{1}$H NMR (600 MHz, $CDCl_3$) δ 10.94 (s, 1H), 8.39 (d, J=2.4 Hz, 1H), 7.53 (dd, J=8.2, 2.3 Hz, 1H), 7.32 (dd, J=9.2, 7.0 Hz, 1H), 7.27 (d, J=6.8 Hz, 1H), 6.42 (d, J=9.2 Hz, 1H), 6.21 (d, J=7.0 Hz, 1H), 2.34 (s, 3H), 2.11 (s, 3H). $^{13}$C NMR (151 MHz, $CDCl_3$) δ 163.43, 158.19, 149.78, 149.22, 140.57, 138.40, 132.74, 119.80, 118.92, 102.42, 48.68, 24.12, 18.15. $^{19}$F NMR (376 MHz, $CDCl_3$) δ −140.29, −140.33, −157.47, −164.12, −164.14.

Example 17: 6-(1-Cyclohexyl-1-(5-methylpyridin-2-yl)ethyl)pyridin-2(1H)-one (L42)

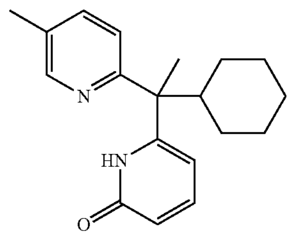 [SMILES: Cc1ccc(C(C)(c2cccc(=O)[nH]2)C2CCCCC2)nc1]

White solid, 0.155 g, 80% yield in the second step. $^{1}$H NMR (600 MHz, $CDCl_3$) δ 11.59 (s, 1H), 8.52 (d, J=2.4 Hz, 1H), 7.44 (dd, J=8.1, 2.4 Hz, 1H), 7.29-7.20 (m, 2H), 6.34 (dd, J=9.1, 2.0 Hz, 1H), 6.10 (dd, J=7.1, 1.8 Hz, 1H), 2.57-2.52 (m, 1H), 2.31 (s, 3H), 1.70-1.60 (m, 3H), 1.58 (s, 3H), 1.26-1.18 (m, 2H), 1.16-0.95 (m, 3H), 0.91-0.88 (m, 2H). $^{13}$C NMR (151 MHz, $CDCl_3$) δ 163.41, 158.97, 151.76, 148.98, 139.72, 136.90, 130.95, 120.14, 117.66, 102.47, 48.03, 47.76, 27.46, 27.07, 26.41, 26.29, 26.06, 17.45, 14.87.

Example 18: 6-(1-Cyclohexyl-1-(5-methylpyridin-2-yl)propyl)pyridin-2(1H)-one (L43)

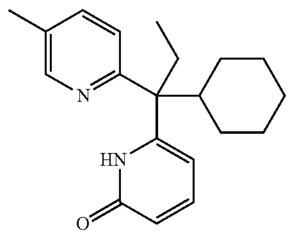 [SMILES: CCC(c1ccc(C)cn1)(c1cccc(=O)[nH]1)C1CCCCC1]

White solid, 0.112 g, 36% yield. $^{1}H$ NMR (600 MHz, $CDCl_3$) δ 11.46 (s, 1H), 8.49 (s, 1H), 7.53-7.48 (m, 1H), 7.43-7.36 (m, 1H), 7.19 (d, J=8.3 Hz, 1H), 6.41 (dd, J=9.1, 1.5 Hz, 1H), 6.20 (d, J=7.5 Hz, 1H), 2.34 (s, 3H), 2.23-2.13 (m, 2H), 2.00 (td, J=11.8, 5.9 Hz, 1H), 1.72-1.43 (m, 5H), 1.22-1.09 (m, 2H), 0.96-0.92 (m, 1H), 0.86-0.81 (m, 1H), 0.77 (t, J=7.3 Hz, 3H), 0.74-0.65 (m, 1H). $^{13}C$ NMR (151 MHz, $CDCl_3$) δ 163.80, 158.03, 151.46, 148.76, 140.64, 137.21, 131.47, 123.44, 117.70, 105.58, 55.13, 47.93, 28.69, 28.39, 27.13, 27.10, 26.48, 18.09, 9.48.

Example 19: 6-(1-Cyclohexyl-1-(5-methylpyridin-2-yl)-2-phenylethyl)pyridin-2(1H)-one (L44)

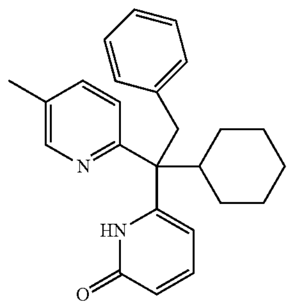 [SMILES: Cc1ccc(C(Cc2ccccc2)(c2cccc(=O)[nH]2)C2CCCCC2)nc1]

White solid, 0.152 g, 41% yield. $^{1}H$ NMR (600 MHz, $CDCl_3$) δ 11.20 (s, 1H), 8.65 (d, J=2.4 Hz, 1H), 7.48 (dd, J=8.3, 2.4 Hz, 1H), 7.38 (dd, J=9.1, 7.1 Hz, 1H), 7.26-7.21 (m, 3H), 7.10 (d, J=8.2 Hz, 1H), 6.89 (dd, J=7.3, 2.3 Hz, 2H), 6.52 (d, J=9.1 Hz, 1H), 6.19-6.11 (m, 1H), 3.70 (s, 2H), 2.46 (s, 3H), 2.21-2.17 (m, 1H), 1.89-1.69 (m, 4H), 1.42-1.26 (m, 2H), 1.18-0.87 (m, 4H). $^{13}C$ NMR (151 MHz, $CDCl_3$) δ 163.71, 157.35, 150.62, 148.83, 140.26, 137.00, 136.58, 131.64, 130.09, 127.84, 126.20, 124.45, 117.88, 106.61, 55.07, 46.87, 39.06, 28.61, 28.60, 26.96, 26.94, 26.45, 18.06.

Example 20: 6-(Cyclohexyl(5-methylpyridin-2-yl)methyl)pyridin-2(1H)-one (L45)

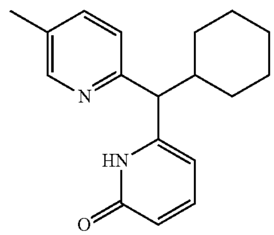 [SMILES: Cc1ccc(C(c2cccc(=O)[nH]2)C2CCCCC2)nc1]

White solid, 0.191 g, 68% yield. $^{1}H$ NMR (600 MHz, $CDCl_3$) δ 11.01 (s, 1H), 8.46 (d, J=2.3 Hz, 1H), 7.41 (dd, J=7.7, 2.3 Hz, 1H), 7.26-7.21 (m, 1H), 7.02 (d, J=7.8 Hz, 1H), 6.37 (d, J=9.2 Hz, 1H), 6.01 (d, J=6.8 Hz, 1H), 3.28 (m, 1H), 2.31 (s, 3H), 2.04 (d, J=10.7 Hz, 1H), 1.73-1.50 (m, 4H), 1.26-1.17 (m, 2H), 1.16-1.06 (m, 2H), 0.95-0.75 (m, 2H). $^{13}C$ NMR (151 MHz, $CDCl_3$) δ 163.96, 156.16, 150.25, 148.18, 140.62, 137.38, 131.93, 123.91, 118.64, 105.63, 56.48, 43.09, 31.68, 31.45, 26.32, 26.10, 26.06, 18.22.

Example 21: The Purpose of this Example is to Demonstrate a Screen for Ligand Effects on an Illustrative C—H Hydroxylation Process

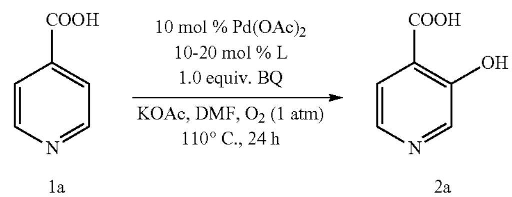 [SMILES: O=C(O)c1ccncc1 ; O=C(O)c1ccncc1O]

1a 2a

Reaction conditions: 1a (0.1 mmol), $Pd(OAc)_2$ (10 mol %), L (10 mol % for the bidentate ligand or 20 mol % for the monodentate ligand), KOAc (2.0 equiv), DMF (0.8 mL), 110° C., 25% $O_2$ in $N_2$, 60 psi, 24 h. The yields as shown in Table 4a were determined by $^{1}H$ NMR analysis of the crude product using 1,3,5-trimethoxybenzene as the internal standard ("n.r."=no reaction).

TABLE 4a

| Ligand Effects | |
|---|---|
| No ligand L, n.r. | 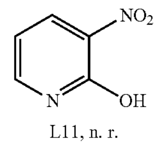 L11, n. r. |
| 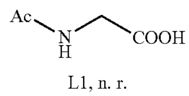 L1, n. r. | 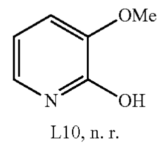 L10, n. r. |

TABLE 4a-continued

| Ligand Effects | |
|---|---|
| 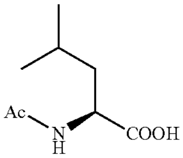<br>L2, n. r. | 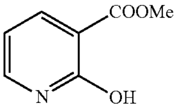<br>L12, n. r. |
| 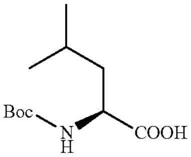<br>L3, n. r. | 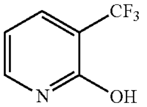<br>L13, n. r. |
| 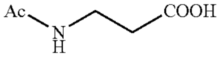<br>L4, n. r. | 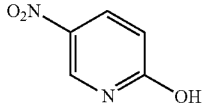<br>L14, n. r. |
| 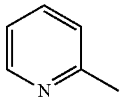<br>L5, n. r. | 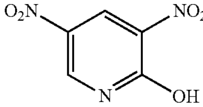<br>L15, n. r. |
| 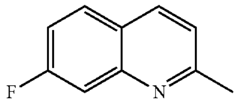<br>L6, n. r. | 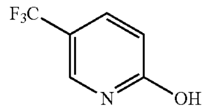<br>L16, n. r. |

TABLE 4a-continued

| Ligand Effects | |
|---|---|
| 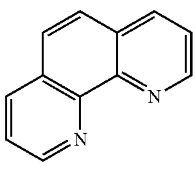<br>L7, n. r. | 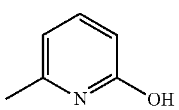<br>L17, n. r. |
| 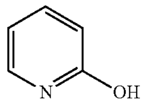<br>L8, n. r. | 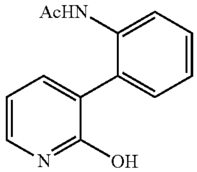<br>L18, n. r. |
| 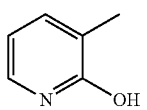<br>L9, n. r. | 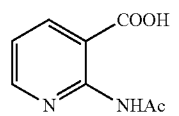<br>L19, n. r. |

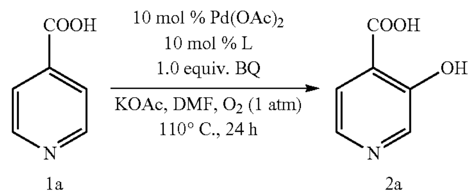 [SMILES: O=C(O)c1ccncc1 ; O=C(O)c1ccncc1O]

1a 2a

General conditions: 1a (0.1 mmol), $Pd(OAc)_2$ (10 mol %), L (10 mol %), KOAc (2.0 equiv), DMF (0.8 mL), 110° C., 25% $O_2$ in $N_2$, 60 psi, 24 h. The yields as shown in Table 4b were determined by $^1$H NMR analysis of the crude product using 1,3,5-trimethoxybenzene as the internal standard ("n.r."=no reaction).

TABLE 4b

| Ligand Effects | |
|---|---|
| 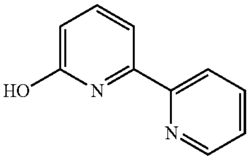<br>L20, n. r. | 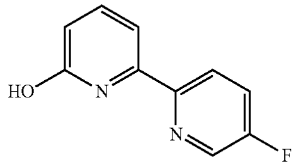<br>L21, n. r. |
| 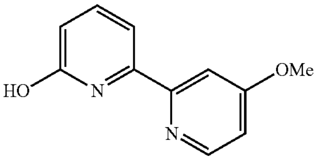<br>L22, n. r. | 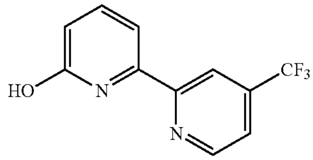<br>L23, n. r. |

TABLE 4b-continued
| Ligand Effects | |
|---|---|
| 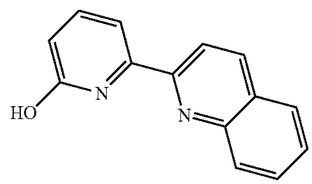<br>L24, <2% yield | 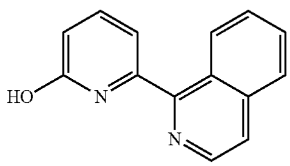<br>L25, n. r. |
| 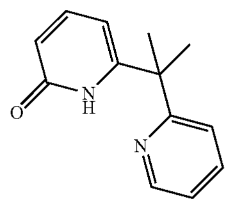<br>L26, 26% | 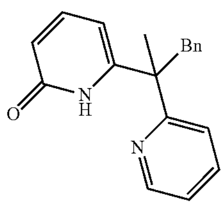<br>L27, 40% |
| 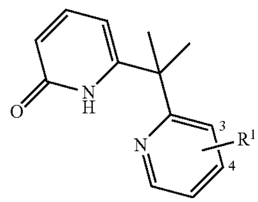 | L28, R1 = 3-Me, 11%;<br>L29, R1 = 4-Me, 34%;<br>L30, R1 = 5-Me, 42%;<br>L31, R1 = 6-F, 13%;<br>L32, R1 = 5-Cl, 29%. |
| 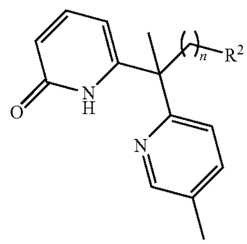 | n = 1<br>L33, R2 = Ph, 48%;<br>L34, R2 = 4-OMe-$C_6H_4$, 33%;<br>L35, R2 = 4-CF3-$C_6H_4$, 36%;<br>L36, R2 = 2-Nap, 47%;<br>L37, R2 = 3,5-di-tBu-$C_6H_3$, 38%;<br>L38, R2 =2-Py, 27%.<br>n = 2<br>L39, R2 = Ph, 43%.<br>n = 0<br>L40, R2 = Ph, 55%;<br>L41, R2 = $C_6F_5$, 21%;<br>L42, R2 = Cy, 72%. |
| 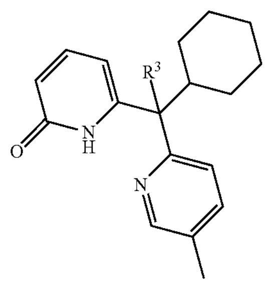 | L43, R3 = Et, 36%;<br>L44, R3 = Bn, 45%;<br>L45, R3 = H, 40%; |

Example 22: The Purpose of this Example is to Show the Effects of Various Bases on the Following Exemplary Reaction

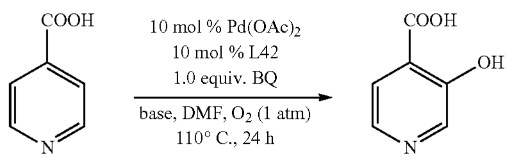 [SMILES: O=C(O)c1ccncc1 ; O=C(O)c1ccncc1O]

General conditions: 1a (0.1 mmol), $Pd(OAc)_2$ (10 mol %), L (10 mol %), base (2.0 equiv), DMF (0.8 mL), 110° C., 25% $O_2$ in $N_2$, 60 psi, 24 h. The yields as shown in Table 5 were determined by $^1$H NMR analysis of the crude product using 1,3,5-trimethoxybenzene as the internal standard.

TABLE 5

| effects of base | |
|---|---|
| base | Yield (%) |
| KOAc | 72 |
| NaOAc | 60 |
| CsOAc | 65 |
| $K_3PO_4$ | 65 |
| $K_2HPO_4$ | 46 |
| $KH_2PO_4$ | 10 |
| $K_2CO_3$ | 25 |
| No base | <5 |

Example 23: The Purpose of this Example is to Demonstrate the Effect of Solvent on the Exemplary Reaction

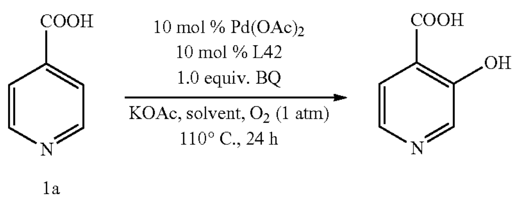 [SMILES: O=C(O)c1ccncc1 ; O=C(O)c1ccncc1O]

1a

General conditions: 1a (0.1 mmol), $Pd(OAc)_2$ (10 mol %), L (10 mol %), KOAc (2.0 equiv), solvent (0.8 mL), 110° C., 25% $O_2$ in $N_2$, 60 psi, 24 h. The yields as shown in Table 6 were determined by $^1$H NMR analysis of the crude product using 1,3,5-trimethoxybenzene as the internal standard.

TABLE 6

| effects of solvent | |
|---|---|
| solvent | yield (%) |
| t-Amyl-OH | 0 |
| 1,4-dioxane | 0 |
| toluene | 0 |
| NMP | 50 |
| DMA | 35 |
| DMF | 72 |

Example 24: The Purpose of this Example is to Demonstrate the Effect of Palladium (II) Source on the Exemplary Reaction

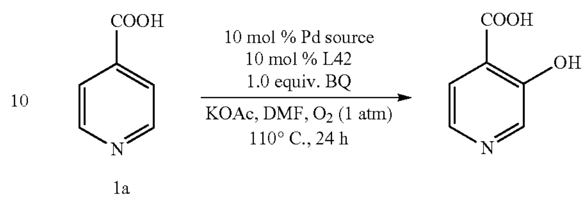

1a

General conditions: 1a (0.1 mmol), Pd source (10 mol %), L (10 mol %), KOAc (2.0 equiv), DMF (0.8 mL), 110° C., 25% $O_2$ in $N_2$, 60 psi, 24 h. The yields as shown in Table 7 were determined by $^1$H NMR analysis of the crude product using 1,3,5-trimethoxybenzene as the internal standard.

TABLE 7

| effects of Pd(II) source | |
|---|---|
| Pd(II) source | yield (%) |
| Pd(OAc)2 | 72 |
| Pd(TFA)2 | 39 |
| PdCl2 | 040 |
| Pd(CH3CN)2Cl | 45 |
| no Pd | 0 |

Example 25: The Purpose of this Example is to Demonstrate the Effect of Benzoquinone (BQ) on the Exemplary Reaction

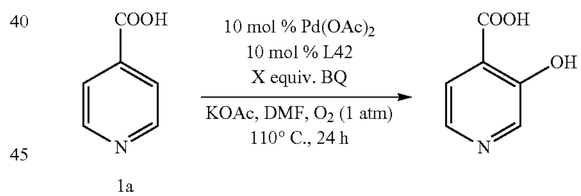

1a

General conditions: 1a (0.1 mmol), Pd source (10 mol %), L (10 mol %), KOAc (2.0 equiv), DMF (0.8 mL), 110° C., 25% $O_2$ in $N_2$, 60 psi, 24 h. The yields as shown in Table 8 were determined by $^1$H NMR analysis of the crude product using 1,3,5-trimethoxybenzene as the internal standard.

TABLE 8

| effects of Pd(II) source | |
|---|---|
| X equiv. BQ | yield (%) |
| 0 | 45 |
| 1 | 72 |
| 1.5 | 78 (72 isolated yield) |
| 2 | 67 |

General Procedure and Characterization Data. Compounds of formula (2) were prepared by the following reaction and general procedure A or general procedure B.

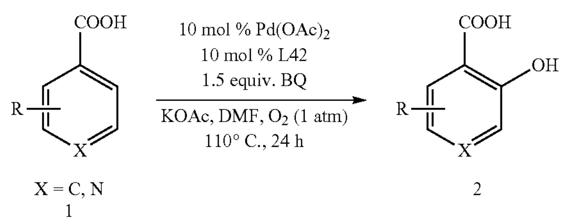

X = C, N

1

2

L42 =

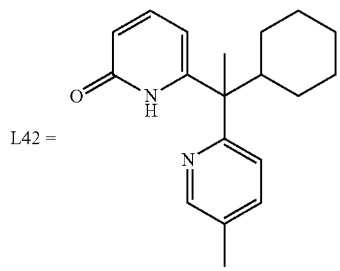 [SMILES: Cc1ccc(C(C)(c2cccc(=O)[nH]2)C2CCCCC2)nc1]

General Procedure A: $Pd(OAc)_2$ (2.2 mg, 0.01 mmol, 10 mol %), ligand L42 (3.0 mg, 0.01 mmol, 10 mol %), BQ (16.2 mg, 0.15 mmol, 1.5 equiv.), KOAc (19.6 mg, 0.2 mmol, 2.0 equiv.), and carboxylic acid 1 (0.1 mmol) were added to a tube with septum stopper. The tube was evacuated and backfilled with $O_2$ three times. DMF (0.8 mL) was added and the reaction mixture was stirred at r.t. for 10 min before heated to 110° C. in presence of an $O_2$ balloon for 24 h. After cooling to room temperature, 0.1 mL HCOOH was added. The mixture was filtered a pad of celite with 5 mL DMF, and the solvent was removed under vacuum. The residue was purified by reverse phase column-chromatography (0%-50% MeCN: $H_2O$) using Biotage Isolera™ one with SNAP Samplet to afford the pure product after evaporation to dryness.

General Procedure B: $Pd(OAc)_2$ (2.2 mg, 0.01 mmol, 10 mol %), ligand L42 (3.0 mg, 0.01 mmol, 10 mol %), BQ (16.2 mg, 0.15 mmol, 1.5 equiv.), KOAc (19.6 mg, 0.2 mmol, 2.0 equiv.), and carboxylic acid 1 (0.1 mmol) were added to a tube with septum stopper. The tube was evacuated and backfilled with $O_2$ three times. DMF (0.8 mL) was added and the reaction mixture was stirred at r.t. for 10 min before heated to 110° C. in presence of an $O_2$ balloon for 24 h. After cooling to room temperature, 0.1 mL HCOOH was added. The mixture was filtered a pad of celite with 5 mL DMF, and the solvent was removed under vacuum. The resulting mixture was purified by pTLC using DCM/MeOH (10/1) with AcOH (1% v/v) as eluent.

Example 26: 3-Hydroxyisonicotinic Acid (2a)

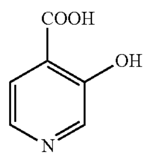

General Procedure A, greyish solid, 10.0 mg, 72% yield. $^1H$ NMR (600 MHz, DMSO-$d_6$) δ 8.05 (s, 1H), 7.86 (d, J=4.8 Hz, 1H), 7.46 (d, J=4.7 Hz, 1H). $^{13}C$ NMR (151 MHz, DMSO-$d_6$) δ 169.67, 158.54, 139.52, 137.51, 125.84, 122.65. The $^1H$ NMR data matches the reported data.[2]

Example 27: 5-Hydroxy-2-(trifluoromethyl)isonicotinic acid (2b)

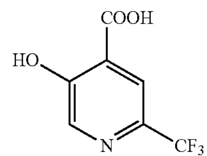

General Procedure A, greyish solid, 15.7 mg, 76% yield. $^1H$ NMR (600 MHz, DMSO-$d_6$) δ 8.47 (s, 1H), 7.94 (s, 1H). $^{13}C$ NMR (151 MHz, DMSO-$d_6$) δ 168.01, 157.71, 141.92, 136.44 (q, $J_{CF}$=34.6 Hz), 122.38, 121.88 (q, $J_{CF}$=271.2 Hz), 120.45 (q, $J_{CF}$=3.3 Hz).

Example 28: 5-Hydroxy-2-methoxyisonicotinic acid (2c)

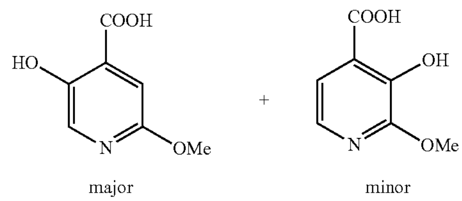 [SMILES: COc1cc(C(=O)O)c(O)cn1 ; COc1nccc(C(=O)O)c1O]

major minor

General Procedure A, greyish solid, 10.2 mg, 60% (total) yield. $^1H$ NMR (600 MHz, DMSO-$d_6$) δ major: 7.91 (s, 1H), 7.00 (s, 1H), 3.79 (s, 3H); minor: 7.62 (d, J=5.3 Hz, 1H), 7.17 (d, J=5.3 Hz, 1H), 3.88 (s, 3H). $^{13}C$ NMR (151 MHz, DMSO-$d_6$) δ major: 170.36, 168.90, 156.73, 149.49, 135.44, 108.57, 53.45.

Example 29: 2-(tert-Butyl)-5-hydroxyisonicotinic acid (2d)

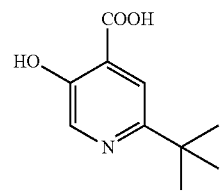

General Procedure A, white solid, 10.1 mg, 52% yield. $^1H$ NMR (600 MHz, DMSO-$d_6$) δ 8.21 (s, 1H), 7.61 (s, 1H), 1.29 (s, 9H). $^{13}C$ NMR (151 MHz, DMSO-$d_6$) δ 169.48, 156.68, 154.80, 137.69, 124.14, 118.02, 36.20, 30.05.

Example 30: 2-Chloro-5-hydroxyisonicotinic acid (2e)

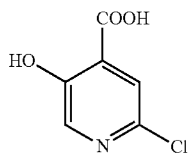 [SMILES: O=C(O)c1cc(Cl)ncc1O]

General Procedure A, white solid, 11.6 mg, 67% yield. $^1$H NMR (600 MHz, DMSO-$d_6$) δ 7.87 (s, 1H), 7.46 (s, 1H). $^{13}$C NMR (151 MHz, DMSO-$d_6$) δ 168.02, 158.18, 138.89, 136.56, 129.41, 122.69.

Example 31: 2-Bromo-5-hydroxyisonicotinic acid (2f)

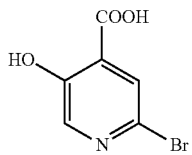

General Procedure A, 48 h, yellowish solid, 8.7 mg, 40% yield. $^1$H NMR (600 MHz, DMSO-$d_6$) δ 8.12 (s, 1H), 7.68 (s, 1H). $^{13}$C NMR (151 MHz, DMSO-$d_6$) δ 167.58, 154.96, 140.89, 128.33, 126.46, 126.18.

Example 32: 2-(2-Chloro-6-methoxyphenyl)-5-hydroxyisonicotinic acid (2g)

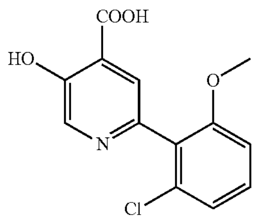 [SMILES: COc1cccc(Cl)c1-c1cc(C(=O)O)c(O)cn1]

General Procedure A, greyish solid, 19.0 mg, 68% yield. $^1$H NMR (600 MHz, DMSO-$d_6$) δ 8.15 (s, 1H), 8.13 (s, 1H), 7.73 (d, J=2.8 Hz, 1H), 7.33 (dd, J=8.8, 2.8 Hz, 1H), 7.13 (d, J=8.8 Hz, 1H), 3.84 (s, 3H). $^{13}$C NMR (151 MHz, DMSO-$d_6$) δ 169.66, 158.36, 155.17, 141.06, 139.32, 130.46, 129.21, 127.74, 125.42, 124.42, 124.03, 113.74, 56.00.

Example 33: 5-Hydroxy-2-(2-methoxy-6-(trifluoromethyl)phenyl)isonicotinic acid (2h)

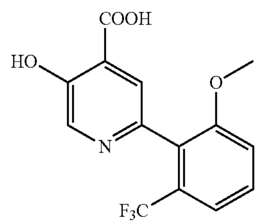 [SMILES: COc1cccc(C(F)(F)F)c1-c1cc(C(=O)O)c(O)cn1]

General Procedure A, greyish solid, 23.5 mg, 75% yield. $^1$H NMR (600 MHz, DMSO-$d_6$) δ 8.17 (s, 1H), 8.16 (s, 1H), 8.05 (d, J=2.5 Hz, 1H), 7.64 (dd, J=8.7, 2.5 Hz, 1H), 7.29 (d, J=8.7 Hz, 1H), 3.93 (s, 3H). $^{13}$C NMR (151 MHz, DMSO-$d_6$) δ 170.04, 159.45, 159.01, 141.24, 139.96, 129.62, 127.12 (q, $J_{CF}$=3.8 Hz), 125.91 (q, $J_{CF}$=3.8 Hz), 125.84, 125.28 (q, $J_{CF}$=272.3 Hz), 124.50, 121.54 (q, $J_{CF}$=32.1 Hz), 112.85, 56.81.

Example 34: 4-Hydroxynicotinic acid (2i)

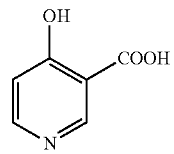

General Procedure A, white solid, 7.8 mg, 56% yield. $^1$H NMR (400 MHz, DMSO-$d_6$) δ 8.60 (d, J=1.5 Hz, 1H), 8.07 (dd, J=7.2, 1.6 Hz, 1H), 6.72 (d, J=7.2 Hz, 1H). $^{13}$C NMR (151 MHz, DMSO-$d_6$) δ 179.01, 166.48, 143.19, 141.18, 117.69, 115.36. The $^1$H NMR data matches the reported data.[2]

Example 35: 4-Hydroxy-2-methylnicotinic acid (2j)

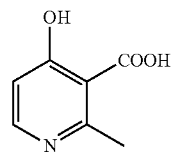

General Procedure A, white solid, 11.5 mg, 75% yield. $^1$H NMR (600 MHz, DMSO-$d_6$) δ 7.95 (d, J=7.1 Hz, 1H), 6.65 (d, J=7.1 Hz, 1H), 2.72 (s, 3H). $^{13}$C NMR (151 MHz, DMSO-$d_6$) δ 179.51, 166.94, 156.31, 139.25, 115.93, 113.35, 20.11.

Example 35: 4-Hydroxy-2,6-dimethylnicotinic acid (2k)

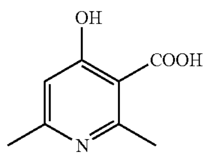

General Procedure A, white solid, 10.8 mg, 65% yield. $^1$H NMR (600 MHz, DMSO-$d_6$) δ 6.50 (s, 1H), 2.72 (s, 3H), 2.33 (s, 3H). $^{13}$C NMR (151 MHz, DMSO-$d_6$) δ 179.45, 166.98, 156.08, 149.91, 114.77, 111.59, 19.67, 18.46.

Example 36: 4-Hydroxy-2-(trifluoromethyl)nicotinic acid (21)

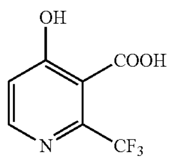 [SMILES: O=C(O)c1c(O)ccnc1C(F)(F)F]

General Procedure A, greyish solid, 16.8 mg, 81% yield. $^1$H NMR (600 MHz, Methanol-$d_4$) δ 8.33 (d, J=5.6 Hz, 1H), 7.05 (d, J=5.8 Hz, 1H). $^{13}$C NMR (151 MHz, DMSO-$d_6$) δ 165.67, 162.72, 150.58, 143.27 (q, $J_{CF}$=32.7 Hz), 121.45 (q, $J_{CF}$=273.6 Hz), 119.35, 114.50.

Example 37: 4-Hydroxy-2-(3,3,3-trifluoropropoxy)nicotinic acid (2m)

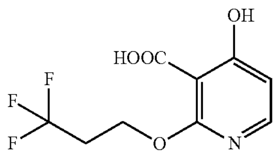

General Procedure A, white solid, 13.1 mg, 52% yield. $^1$H NMR (600 MHz, DMSO-$d_6$) δ 7.59 (d, J=5.9 Hz, 1H), 6.15 (d, J=5.8 Hz, 1H), 4.39 (t, J=6.6 Hz, 2H), 2.70 (dt, J=11.5, 6.6 Hz, 2H). $^{13}$C NMR (151 MHz, DMSO-$d_6$) δ 176.59, 168.43, 163.76, 147.04, 127.21 (q, $J_{CF}$=274.7 Hz), 110.61, 58.10 (q, $J_{CF}$=3.8 Hz), 33.38 (q, $J_{CF}$=27.2 Hz).

Example 38: 4-Hydroxy-2-((2,2,2-trifluoroethyl)amino)nicotinic acid (2n)

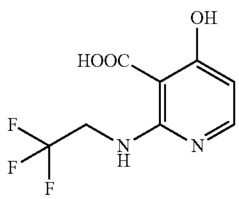 [SMILES: O=C(O)c1c(O)ccnc1NCC(F)(F)F]

General Procedure A, white solid, 18.4 mg, 78% yield. $^1$H NMR (600 MHz, DMSO-$d_6$) δ 9.97 (s, 1H), 7.64 (d, J=6.7 Hz, 1H), 6.12 (d, J=6.7 Hz, 1H), 4.33 (td, J=9.6, 6.9 Hz, 2H). $^{13}$C NMR (151 MHz, DMSO-$d_6$) δ 176.14, 172.00, 156.23, 125.96 (q, $J_{CF}$=274.9 Hz), 107.34, 96.57, 41.54 (q, $J_{CF}$=32.6 Hz).

Example 39: 4-Hydroxy-2-((2-(trifluoromethyl)phenyl)amino)nicotinic acid (20)

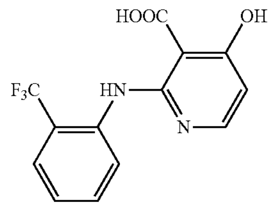 [SMILES: O=C(O)c1c(O)ccnc1Nc1ccccc1C(F)(F)F]

General Procedure A, greyish solid, 19.4 mg, 65% yield. $^1$H NMR (600 MHz, DMSO-$d_6$) δ 11.68 (brs, 1H), 11.51 (s, 1H), 7.83 (d, J=2.0 Hz, 1H), 7.71 (m, 3H), 7.49 (d, J=7.3 Hz, 1H), 6.27 (d, J=7.3 Hz, 1H). $^{13}$C NMR (151 MHz, DMSO-$d_6$) δ 179.44, 171.51, 153.09, 138.02, 136.99, 131.56, 131.07 (q, $J_{CF}$=31.8 Hz), 129.97, 124.27 (q, $J_{CF}$=271.1 Hz), 123.95 (q, $J_{CF}$=3.9 Hz), 122.87 (q, $J_{CF}$=4.2 Hz), 110.09, 96.60.

Example 40: 4-Hydroxy-6-methylnicotinic acid (2p)

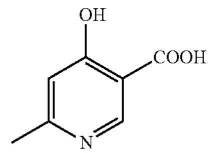

General Procedure A, white solid, 9.2 mg, 60% yield. $^1$H NMR (600 MHz, Methanol-$d_4$) δ 8.56 (s, 1H), 6.65 (s, 1H), 2.45 (s, 3H). $^{13}$C NMR (151 MHz, Methanol-$d_4$) δ 177.22, 169.04, 153.98, 144.18, 115.38, 113.97, 18.53.

Example 41: 2-Hydroxy-6-methylnicotinic acid (2p')

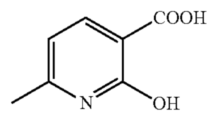

The yield is determined by $^1$NMR using 1,3,5-trimethoxy benzene as internal standard. $^1$H NMR (600 MHz, DMSO-$d_6$) δ 8.27 (d, J=7.4 Hz, 1H), 6.54 (d, J=7.5 Hz, 1H), 2.37 (s, 3H).

Example 42: 4-Hydroxy-6-(trifluoromethyl)nicotinic acid (2q)

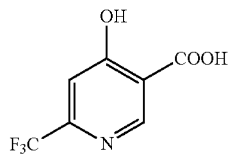

General Procedure A, white solid, 13.9 mg, 67% yield. $^1$H NMR (600 MHz, Methanol-$d_4$) δ 9.20 (s, 1H), 7.59 (s, 1H). $^{13}$C NMR (151 MHz, Methanol-$d_4$) δ 170.80, 168.82, 150.14, 148.55 (q, $J_{CF}$=35.3 Hz), 120.22 (q, $J_{CF}$=272.1 Hz), 113.48, 111.04.

Example 43: 2-Hydroxy-6-(trifluoromethyl)nicotinic acid (2q')

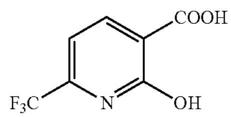

The yield is determined by $^1$NMR using 1,3,5-trimethoxy benzene as internal standard. $^1$H NMR (600 MHz, Methanol-$d_4$) δ 8.52 (d, J=7.7 Hz, 1H), 7.32 (dd, J=7.7, 1.8 Hz, 1H).

Example 44: 6-Chloro-4-hydroxynicotinic acid (2r)

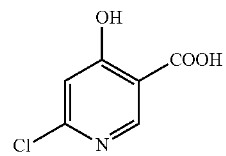 [SMILES: O=C(O)c1cnc(Cl)cc1O]

General Procedure A, white solid, 11.2 mg, 65% yield. $^1$H NMR (600 MHz, Methanol-$d_4$) δ 8.66 (s, 1H), 6.99 (s, 1H). $^{13}$C NMR (151 MHz, Methanol-$d_4$) δ 177.25, 168.97, 151.89, 149.24, 112.87, 111.23.

Example 45: 6-Chloro-4-hydroxynicotinic acid (2r')

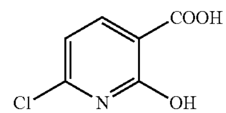 [SMILES: O=C(O)c1ccc(Cl)nc1O]

The yield is determined by $^1$NMR using 1,3,5-trimethoxy benzene as internal standard. $^1$H NMR (600 MHz, Methanol-$d_4$) δ 8.34 (d, J=7.8 Hz, 1H), 6.99 (d, J=7.8 Hz, 1H).

Example 46: 3-Hydroxy-6-methylpicolinic acid (2s)

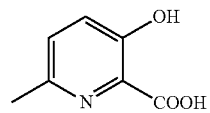

General Procedure A, white solid, 8.3 mg, 54% yield. $^1$H NMR (600 MHz, DMSO-$d_6$) δ 7.68 (d, J=8.6 Hz, 1H), 7.57 (d, J=8.7 Hz, 1H), 2.54 (s, 3H). $^{13}$C NMR (151 MHz, DMSO-$d_6$) δ 166.32, 158.72, 144.68, 132.13, 130.14, 130.06, 20.12.

Example 47: 3-Hydroxy-6-methoxypicolinic acid (2t)

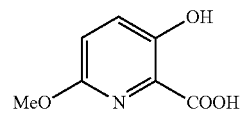 [SMILES: COc1ccc(O)c(C(=O)O)n1]

General Procedure A, white solid, 10.3 mg, 61% yield. $^1$H NMR (600 MHz, DMSO-$d_6$) δ 7.07 (d, J=8.7 Hz, 1H), 6.66 (d, J=8.7 Hz, 1H), 3.75 (s, 3H). $^{13}$C NMR (151 MHz, DMSO-$d_6$) δ 170.61, 155.58, 154.47, 133.17, 128.96, 114.03, 53.15.

Example 48: 3-Hydroxy-6-(trifluoromethyl)picolinic acid (2u)

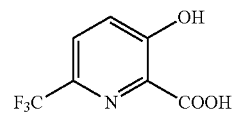

General Procedure A, greyish solid, 14.5 mg, 70% yield. $^1$H NMR (600 MHz, DMSO-$d_6$) δ 7.59 (d, J=8.6 Hz, 1H), 7.17 (d, J=8.6 Hz, 1H). $^{13}$C NMR (151 MHz, DMSO-$d_6$) δ 168.50, 164.34, 137.48, 132.68 (q, $J_{CF}$=33.9 Hz), 125.26, 123.53 (q, $J_{CF}$=2.6 Hz), 122.44 (q, $J_{CF}$=270.8 Hz).

Example 49: 3-Hydroxyquinoline-4-carboxylic acid (2v)

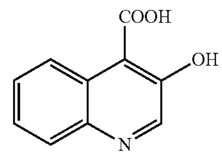 [SMILES: O=C(O)c1c(O)cnc2ccccc12]

General Procedure A, white solid, 10.3 mg, 57% yield. $^1$H NMR (600 MHz, DMSO-$d_6$) δ 8.74 (s, 1H), 8.13 (d, J=8.2 Hz, 1H), 7.96 (dd, J=7.9, 1.7 Hz, 1H), 7.62-7.58 (m, 2H). $^{13}$C NMR (151 MHz, DMSO-$d_6$) δ 168.46, 149.93, 144.37, 141.52, 128.89, 128.12, 126.26, 125.03, 124.07, 118.64.

Example 50: 7-Hydroxyquinoline-6-carboxylic acid (2w)

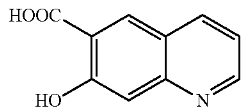 [SMILES: O=C(O)c1cc2cccnc2cc1O]

General Procedure A, white solid, 11.4 mg, 60% yield. $^1H$ NMR (600 MHz, DMSO-$d_6$) δ 8.80 (d, J=4.5 Hz, 1H), 8.49 (s, 1H), 8.48 (d, J=7.8 Hz, 1H), 7.33 (dd, J=8.1, 4.5 Hz, 1H), 7.13 (s, 1H). $^{13}C$ NMR (151 MHz, DMSO-$d_6$) δ 169.94, 164.43, 149.49, 148.24, 139.75, 131.45, 122.28, 121.12, 117.47, 107.87.

Example 51: 1-(4-(2,3-Dimethylphenoxy)butanoyl)-6-hydroxy-1,2,3,4-tetrahydroquinoline-5-carboxylic acid (2x)

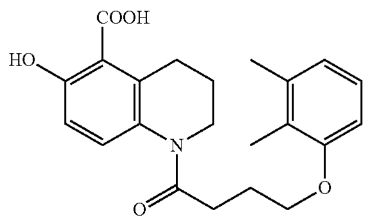 [SMILES: Cc1cccc(OCCCC(=O)N2CCCc3c2ccc(O)c3C(=O)O)c1C]

General Procedure B, white solid, 24.5 mg, 64% yield. $^1H$ NMR (600 MHz, DMSO-$d_6$) δ 6.98 (dt, J=16.6, 7.8 Hz, 2H), 6.70 (d, J=7.8 Hz, 2H), 6.51 (d, J=8.5 Hz, 1H), 3.84 (brs, 2H), 3.58 (t, J=6.9 Hz, 2H), 3.26-3.12 (m, 2H), 2.48 (brs, 2H), 2.17 (s, 3H), 1.95-1.89 (m, 5H), 1.68 (d, J=8.7 Hz, 2H). $^{13}C$ NMR (151 MHz, DMSO-$d_6$) δ 172.54, 171.23, 161.50, 156.27, 138.28, 137.15, 129.24, 127.79, 125.82, 124.16, 121.90, 117.30, 113.60, 109.15, 66.96, 41.31, 30.05, 25.14, 23.99, 23.55, 19.74, 11.24.

Example 52: 7-Hydroxyquinoxaline-6-carboxylic acid (2y)

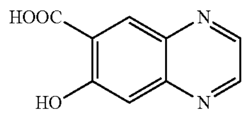 [SMILES: O=C(O)c1cc2nccnc2cc1O]

General Procedure A, white solid, 12.8 mg, 68% yield. $^1H$ NMR (600 MHz, DMSO-$d_6$) δ 8.89 (d, J=1.8 Hz, 1H), 8.80 (d, J=1.8 Hz, 1H), 8.49 (s, 1H), 7.42 (s, 1H). $^{13}C$ NMR (151 MHz, DMSO-$d_6$) δ 170.22, 159.00, 147.95, 145.68, 144.09, 136.05, 132.55, 120.22, 111.91.

Example 53: 1-Acetyl-3-(3-amino-3-oxopropyl)-5-hydroxy-1H-indole-4-carboxylic acid (2z)

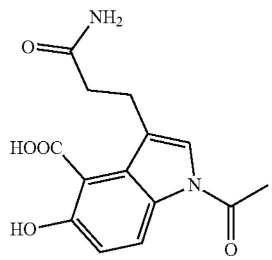 [SMILES: CC(=O)n1cc(CCC(N)=O)c2c(C(=O)O)c(O)ccc21]

General Procedure A, white solid, 12.2 mg, 42% yield. $^1H$ NMR (600 MHz, DMSO-$d_6$) δ 8.08 (d, J=8.7 Hz, 1H), 7.49 (s, 1H), 7.39 (s, 1H), 6.89 (d, J=2.4 Hz, 1H), 6.82 (s, 1H), 6.76 (dd, J=8.7, 2.4 Hz, 1H), 2.80 (t, J=7.7 Hz, 2H), 2.54 (s, 3H), 2.44 (t, J=7.7 Hz, 2H). $^{13}C$ NMR (151 MHz, DMSO-$d_6$) δ 173.65, 169.06, 168.37, 153.76, 131.56, 129.01, 123.63, 120.81, 116.64, 113.40, 103.94, 34.48, 23.50, 20.43.

Example 54: 6-Hydroxybenzo[b]thiophene-5-carboxylic acid (2aa)

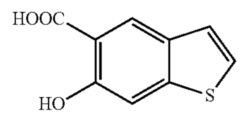 [SMILES: O=C(O)c1cc2ccsc2cc1O]

General Procedure B, greyish solid, 14.9 mg, 77% yield. $^1H$ NMR (600 MHz, DMSO-$d_6$) δ 8.25 (s, 1H), 7.34 (d, J=5.4 Hz, 1H), 7.28 (d, J=5.4 Hz, 1H), 7.20 (s, 1H). $^{13}C$ NMR (151 MHz, DMSO-$d_6$) δ 171.92, 159.69, 143.21, 130.69, 125.20, 124.20, 122.76, 118.45, 107.37.

Example 55

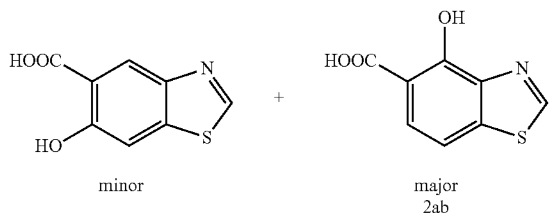 [SMILES: O=C(O)c1cc2ncsc2cc1O ; O=C(O)c1ccc2scnc2c1O]

minor + major 2ab

General Procedure B, greyish solid, 15.0 mg, 65% total yield. $^1H$ NMR (600 MHz, DMSO-$d_6$)) δ 9.32 (m, 1.54H, major+minor), 8.48 (s, 0.54H, minor), 7.83 (d, J=8.2 Hz, 1H), 7.31 (s, 0.54H, minor), 7.26 (d, J=8.1 Hz, 1H). $^{13}C$ NMR (151 MHz, DMSO-$d_6$) δ 171.84, 169.72, 161.35, 160.97, 158.23, 156.89, 156.72, 156.24, 128.17, 123.83, 122.03, 121.73, 116.31, 113.11, 109.68, 108.07.

Example 56

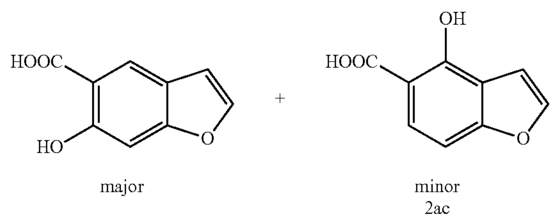 [SMILES: O=C(O)c1cc2ccoc2cc1O ; O=C(O)c1ccc2occc2c1O]

major minor 2ac

General Procedure B, white solid, 13.9 mg, 78% total yield. $^{1}$H NMR (600 MHz, DMSO-$d_6$)) δ 8.07 (s, 1H), 7.80 (d, J=2.1 Hz, 0.51H, minor), 7.75 (d, J=2.2 Hz, 1H), 7.71 (d, J=9.0 Hz, 0.49H, minor), 6.91 (d, J=8.4 Hz, 0.58H, minor), 6.88-6.85 (m, 1.49H, major+minor), 6.81 (d, J=2.2 Hz, 1H). $^{13}$C NMR (151 MHz, DMSO-$d_6$) δ 160.71, 158.85, 157.81, 157.44, 144.44, 143.98, 126.81, 122.99, 122.30, 119.90, 117.85, 116.41, 106.91, 104.88, 100.31, 97.39.

Example 57: 6-Hydroxy-2,3-dihydrobenzo[b][1,4]dioxine-5-carboxylic acid (2ad)

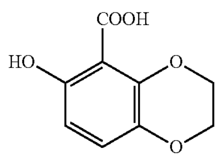 [SMILES: O=C(O)c1c(O)ccc2c1OCCO2]

General Procedure B, white solid, 12.9 mg, 66% yield. $^{1}$H NMR (600 MHz, DMSO-$d_6$) δ 6.75 (d, J=8.8 Hz, 1H), 6.29 (d, J=8.7 Hz, 1H), 4.21 (brs, 2H), 4.13 (brs, 2H). $^{13}$C NMR (151 MHz, DMSO-$d_6$) δ 170.32, 154.48, 143.04, 135.28, 119.64, 109.27, 108.10, 64.43, 63.21.

Example 58: 2-Hydroxy-4-morpholinobenzoic acid (2ae)

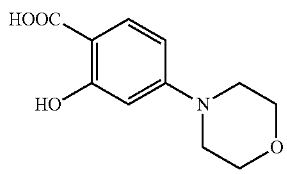 [SMILES: O=C(O)c1ccc(N2CCOCC2)cc1O]

General Procedure B, white solid, 18.1 mg, 81% yield. $^{1}$H NMR (600 MHz, DMSO-$d_6$)) δ 7.73-7.43 (m, 1H), 6.40 (d, J=7.5 Hz, 1H), 6.25 (s, 1H), 3.69 (t, J=4.9 Hz, 4H), 3.17 (t, J=4.8 Hz, 4H). $^{13}$C NMR (151 MHz, DMSO-$d_6$) δ 171.93, 163.02, 156.15, 131.13, 105.79, 102.54, 99.76, 65.83, 46.63.

Example 59: 2-Hydroxy-4-(4-oxo-2-phenyl-4,5,6,7-tetrahydro-1H-indol-1-yl)benzoic acid (2af)

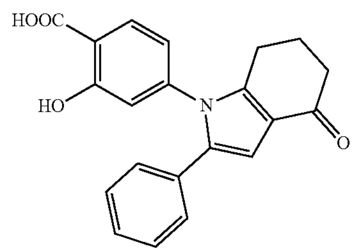 [SMILES: O=C(O)c1ccc(-n2c(-c3ccccc3)cc3c2CCCC3=O)cc1O]

General Procedure B, white solid, 27.8 mg, 80% yield. $^{1}$H NMR (600 MHz, DMSO-$d_6$) δ 7.81 (d, J=8.3 Hz, 1H), 7.28-7.23 (m, 2H), 7.22-7.19 (m, 1H), 7.14-7.11 (m, 2H), 6.91 (d, J=2.1 Hz, 1H), 6.75 (dd, J=8.4, 2.1 Hz, 1H), 6.64 (s, 1H), 2.68 (t, J=6.1 Hz, 2H), 2.40 (dd, J=7.2, 5.5 Hz, 2H), 2.04 (t, J=6.3 Hz, 2H). $^{13}$C NMR (151 MHz, DMSO-$d_6$) δ 193.12, 171.13, 161.37, 145.90, 142.93, 135.07, 131.41, 131.30, 128.42, 127.83, 127.17, 120.71, 118.68, 116.18, 113.06, 105.80, 37.57, 23.25, 22.40.

Example 60: 2-Hydroxy-9H-carbazole-1-carboxylic acid (2ag)

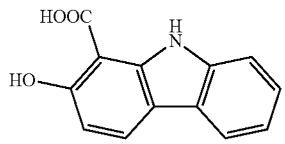 [SMILES: O=C(O)c1c(O)ccc2c1[nH]c1ccccc12]

General Procedure B, white solid, 17.3 mg, 76% yield. $^{1}$H NMR (600 MHz, DMSO-$d_6$) δ 11.03 (s, 1H), 8.20 (d, J=8.0 Hz, 1H), 7.98 (d, J=7.3 Hz, 1H), 7.66 (d, J=7.6 Hz, 1H), 7.28 (d, J=7.5 Hz, 1H), 7.13 (t, J=7.1 Hz, 1H), 6.73 (d, J=7.9 Hz, 1H). $^{13}$C NMR (151 MHz, DMSO-$d_6$) δ 172.31, 161.47, 139.55, 138.96, 127.48, 124.29, 122.27, 119.44, 118.84, 115.80, 111.97, 108.14, 96.93.

Example 61: 3-hydroxydibenzo[b,d]furan-4-carboxylic acid (2ah)

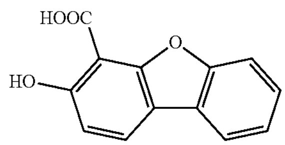 [SMILES: O=C(O)c1c(O)ccc2c1oc1ccccc12]

General Procedure B, greyish solid, 13.0 mg, 57% yield. $^{1}$H NMR (600 MHz, DMSO-$d_6$) δ 7.92-7.87 (m, 1H), 7.83 (d, J=8.4 Hz, 1H), 7.60 (d, J=8.1 Hz, 1H), 7.33-7.29 (m, 1H), 7.27 (d, J=7.4 Hz, 1H), 6.70 (d, J=8.4 Hz, 1H). $^{13}$C NMR (151 MHz, DMSO-$d_6$) δ 168.98, 165.28, 156.20, 155.33, 124.45, 124.35, 122.77, 122.53, 118.96, 113.08, 112.98, 111.16, 105.70.

Example 62: 3-Hydroxydibenzo[b,d]thiophene-4-carboxylic acid (2ai)

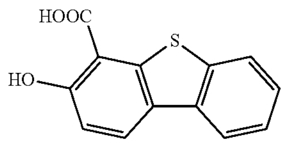 [SMILES: O=C(O)c1c(O)ccc2c1sc1ccccc12]

General Procedure B, white solid, 17.1 mg, 70% yield. $^{1}$H NMR (600 MHz, DMSO-$d_6$) δ 8.12-8.09 (m, 2H), 7.84 (d, J=7.8 Hz, 1H), 7.36 (t, J=7.4 Hz, 1H), 7.30 (t, J=7.4 Hz, 1H), 6.85 (d, J=8.4 Hz, 1H). $^{13}$C NMR (151 MHz, DMSO-$d_6$) δ 171.66, 163.43, 141.08, 140.47, 135.14, 125.55, 124.51, 124.35, 123.86, 122.19, 119.92, 114.64, 113.09.

Example 63: 2-Hydroxy-4-(pyridin-3-yl)benzoic acid (2aj)

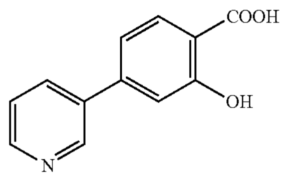 [SMILES: O=C(O)c1ccc(-c2cccnc2)cc1O]

General Procedure A, white solid, mg, 68% yield. $^{1}$H NMR (600 MHz, DMSO-$d_6$) δ 8.99-8.93 (m, 1H), 8.63 (d, J=4.9 Hz, 1H), 8.16 (dd, J=8.0, 2.4 Hz, 1H), 7.90 (d, J=8.2 Hz, 1H), 7.53 (dd, J=8.0, 4.8 Hz, 1H), 7.34 (d, J=1.8 Hz, 1H), 7.31 (d, J=8.2 Hz, 1H). $^{13}$C NMR (151 MHz, DMSO-$d_6$) δ 171.66, 162.86, 161.57, 149.29, 147.69, 143.91, 134.58, 131.06, 117.72, 115.10, 112.83, 103.46.

Example 64: 5-Hydroxy-2-phenylisonicotinic acid (2ak)

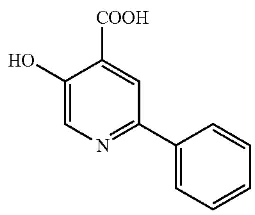 [SMILES: O=C(O)c1cc(-c2ccccc2)ncc1O]

General Procedure A, white solid, 14.2 mg, 66% yield. $^{1}$H NMR (600 MHz, DMSO-$d_6$) δ 8.46 (s, 1H), 8.09 (s, 1H), 7.98 (d, J=8.4 Hz, 2H), 7.47 (t, J=7.7 Hz, 2H), 7.39 (t, J=7.3 Hz, 1H). $^{13}$C NMR (151 MHz, DMSO-$d_6$) δ 169.21, 154.29, 146.67, 140.19, 137.69, 128.82, 128.34, 125.85, 122.62, 119.08.

Example 65: 5-Hydroxy-2-(4-(trifluoromethyl)phenyl)isonicotinic acid (2al)

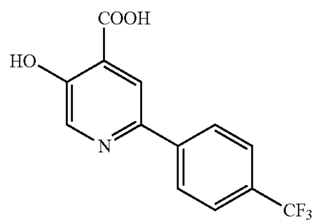

General Procedure A, white solid, 14.1 mg, 50% yield. $^{1}$H NMR (600 MHz, DMSO-$d_6$) δ 8.21 (s, 1H), 8.16 (d, J=8.2 Hz, 2H), 8.13 (s, 1H), 7.75 (d, J=8.2 Hz, 2H). $^{13}$C NMR (151 MHz, DMSO-$d_6$) δ 169.50, 159.58, 143.19, 142.22, 140.08, 127.34 (q, $J_{CF}$=31.8 Hz), 126.16, 125.82, 125.55 (q, $J_{CF}$=3.8 Hz), 124.56 (q, $J_{CF}$=270.6 Hz), 119.78.

Example 66: 3-Hydroxy-6-(naphthalen-1-yl)picolinic acid (2am)

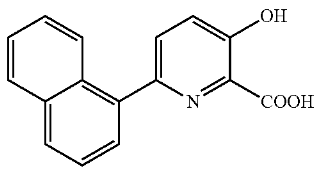 [SMILES: O=C(O)c1nc(-c2cccc3ccccc23)ccc1O]

General Procedure A, white solid, 14.6 mg, 55% yield. $^{1}$H NMR (600 MHz, DMSO-$d_6$) δ 8.08 (d, J=8.4 Hz, 1H), 7.97 (d, J=8.1 Hz, 1H), 7.93 (dd, J=7.6, 1.9 Hz, 1H), 7.58-7.50 (m, 3H), 7.47 (ddd, J=8.3, 6.7, 1.4 Hz, 1H), 7.43 (d, J=8.4 Hz, 1H), 7.22 (d, J=8.4 Hz, 1H). $^{13}$C NMR (151 MHz, DMSO-$d_6$) δ 170.28, 159.53, 145.65, 138.77, 137.57, 133.52, 131.01, 128.17, 127.62, 127.57, 126.90, 126.10, 125.85, 125.71, 125.48, 124.52.

Example 67: 3-Hydroxy-6-phenylpicolinic acid (2an)

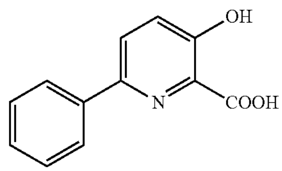 [SMILES: O=C(O)c1nc(-c2ccccc2)ccc1O]

General Procedure A, white solid, 14.1 mg, 65% yield. $^{1}$H NMR (600 MHz, DMSO-$d_6$) δ 8.00-7.95 (m, 2H), 7.75 (d, J=8.5 Hz, 1H), 7.41 (t, J=7.7 Hz, 2H), 7.30 (t, J=7.3 Hz, 1H), 7.13 (d, J=8.5 Hz, 1H). $^{13}$C NMR (151 MHz, DMSO-$d_6$) δ 170.15, 160.07, 143.76, 139.57, 137.43, 128.48, 127.25, 125.75, 124.87, 123.05.

Example 68: 3-Hydroxy-6-(p-tolyl)picolinic acid (2ao)

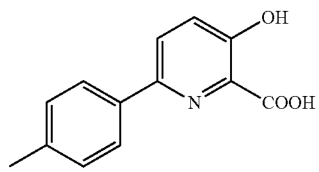 [SMILES: Cc1ccc(-c2ccc(O)c(C(=O)O)n2)cc1]

General Procedure A, 14.5 mg, 63% yield. $^1$H NMR (600 MHz, DMSO-$d_6$) δ 7.85 (d, J=7.9 Hz, 2H), 7.71 (d, J=8.6 Hz, 1H), 7.22 (d, J=7.8 Hz, 2H), 7.12 (d, J=8.5 Hz, 1H), 2.32 (s, 3H). $^{13}$C NMR (151 MHz, DMSO-$d_6$) δ 170.33, 159.66, 144.06, 137.34, 136.88, 136.43, 129.11, 125.69, 124.85, 122.82, 20.76.

Example 69: 3-Hydroxy-6-(4-methoxyphenyl)picolinic acid (2ap)

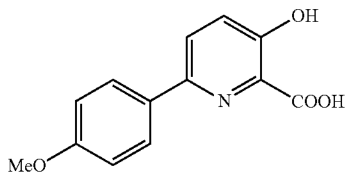 [SMILES: COc1ccc(-c2ccc(O)c(C(=O)O)n2)cc1]

General Procedure A, white solid, 13.4 mg, 55% yield. $^1$H NMR (600 MHz, DMSO-$d_6$) δ 7.90 (d, J=8.8 Hz, 2H), 7.67 (d, J=8.5 Hz, 1H), 7.10-7.07 (m, 1H), 6.97 (d, J=8.9 Hz, 2H), 3.79 (s, 3H). $^{13}$C NMR (151 MHz, DMSO-$d_6$) δ 170.17, 159.40, 158.78, 143.75, 137.30, 132.31, 126.96, 124.77, 122.27, 113.82, 55.11.

Example 70: 3-Hydroxy-6-(4-(trifluoromethyl)phenyl)picolinic acid (2aq)

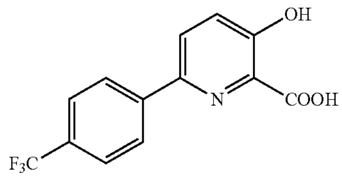 [SMILES: O=C(O)c1nc(-c2ccc(C(F)(F)F)cc2)ccc1O]

General Procedure A, white solid, 22.3 mg, 79% yield. $^1$H NMR (600 MHz, DMSO-$d_6$) δ 8.21 (d, J=8.2 Hz, 2H), 7.88 (d, J=8.6 Hz, 1H), 7.76 (d, J=8.2 Hz, 2H), 7.17 (d, J=8.6 Hz, 1H). $^{13}$C NMR (151 MHz, DMSO-$d_6$) δ 169.83, 161.27, 143.34, 141.63, 137.66, 127.35 (q, $J_{CF}$=31.6 Hz), 126.18, 125.39 (q, $J_{CF}$=3.8 Hz), 124.59 (q, $J_{CF}$=270.3 Hz), 125.08, 123.75.

Example 71: 2-Hydroxy-4-(pyridin-2-yl)benzoic acid (2ar)

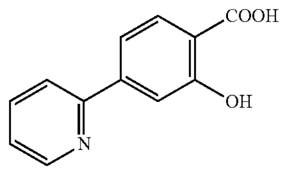 [SMILES: O=C(O)c1ccc(-c2ccccn2)cc1O]

General Procedure A, white solid, 13.6 mg, 63% yield. $^1$H NMR (600 MHz, DMSO-$d_6$) δ 8.70 (d, J=4.8 Hz, 1H), 8.03 (dd, J=8.0, 2.8 Hz, 1H), 7.94-7.88 (m, 2H), 7.68-7.63 (m, 2H), 7.42 (dd, J=7.4, 4.8 Hz, 1H). $^{13}$C NMR (151 MHz, DMSO-$d_6$) δ 171.68, 161.36, 154.37, 149.63, 145.23, 137.54, 130.76, 123.68, 121.14, 117.38, 114.76, 113.26.

Example 72: 2-Hydroxy-5-(pyridin-2-yl)benzoic acid (2as)

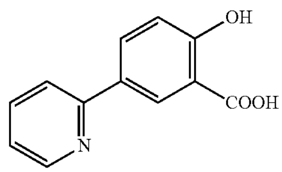 [SMILES: O=C(O)c1cc(-c2ccccn2)ccc1O]

General Procedure A, white solid, 15.1 mg, 70% yield. $^1$H NMR (600 MHz, DMSO-$d_6$) δ 8.59 (d, J=4.7 Hz, 1H), 8.52 (s, 1H), 8.06 (d, J=8.5 Hz, 1H), 7.85-7.79 (m, 2H), 7.25 (dd, J=7.1, 4.7 Hz, 1H), 6.89 (d, J=8.5 Hz, 1H). $^{13}$C NMR (151 MHz, DMSO-$d_6$) δ 169.62, 163.23, 155.83, 149.31, 137.11, 131.42, 128.59, 128.10, 121.52, 119.01, 117.30, 116.87.

Example 73: 4-Acetamido-2-hydroxybenzoic acid (2at)

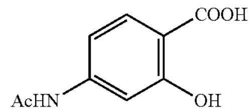 [SMILES: CC(=O)Nc1ccc(C(=O)O)c(O)c1]

General Procedure B, white solid, 13.7 mg, 70% yield. $^1$H NMR (600 MHz, DMSO-$d_6$) δ 10.24 (s, 1H), 7.66 (d, J=8.5 Hz, 1H), 7.26 (s, 1H), 6.99 (d, J=8.1 Hz, 1H), 2.05 (s, 3H). $^{13}$C NMR (151 MHz, DMSO-$d_6$) δ 172.43, 169.35, 162.77, 144.95, 131.19, 110.72, 109.67, 106.16, 24.65.

Example 74: 2-((tert-Butoxycarbonyl)amino)-6-hydroxybenzoic acid (2au)

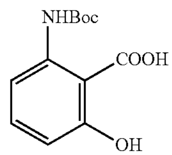 [SMILES: CC(C)(C)OC(=O)Nc1cccc(O)c1C(=O)O]

General Procedure B, white solid, 19.2 mg, 76% yield. $^1H$ NMR (600 MHz, DMSO-$d_6$) δ 12.74 (s, 1H), 7.54 (d, J=8.2 Hz, 1H), 7.04 (t, J=8.2 Hz, 1H), 6.28 (d, J=8.1 Hz, 1H), 1.44 (s, 9H). $^{13}C$ NMR (151 MHz, DMSO-$d_6$) δ 174.04, 163.57, 152.50, 142.12, 131.20, 109.53, 105.93, 105.73, 78.55, 28.15.

Example 75: 5-formyl-2-hydroxybenzoic acid (2av)

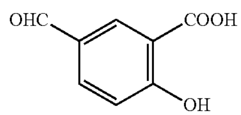 [SMILES: O=Cc1ccc(O)c(C(=O)O)c1]

General Procedure A, white solid, 12.1 mg, 73% yield. $^1H$ NMR (600 MHz, DMSO-$d_6$) δ 9.87 (s, 1H), 8.34 (d, J=2.2 Hz, 1H), 7.97 (dd, J=8.6, 2.2 Hz, 1H), 7.08 (d, J=8.6 Hz, 1H). $^{13}C$ NMR (151 MHz, DMSO-$d_6$) δ 190.91, 170.97, 166.57, 134.74, 133.93, 127.77, 118.27, 114.42.

Example 76: 4'-((1,7'-dimethyl-2'-propyl-1H,3'H-[2,5'-bibenzo[d]imidazol]-3'-yl)methyl)-3-hydroxy-[1,1'-biphenyl]-2-carboxylic acid (2aw)

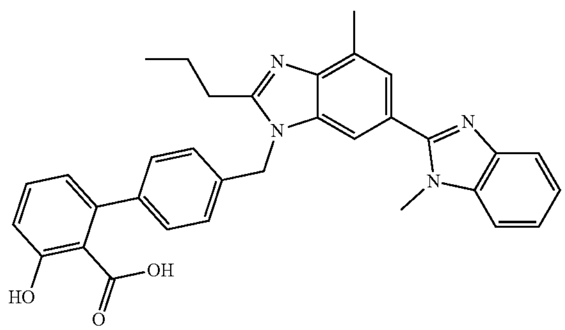 [SMILES: CCCc1nc2c(C)cc(-c3nc4ccccc4n3C)cc2n1Cc1ccc(-c2cccc(O)c2C(=O)O)cc1]

General Procedure B, white solid, 31.8 mg, 60% yield. $^1H$ NMR (600 MHz, $CDCl_3$) δ 8.40-8.33 (m, 1H), 7.39 (ddt, J=7.5, 4.8, 1.4 Hz, 4H), 7.28 (d, J=7.7 Hz, 3H), 7.12 (d, J=7.8 Hz, 2H), 7.07-7.02 (m, 2H), 6.89 (d, J=1.6 Hz, 1H), 6.83 (dd, J=7.4, 1.2 Hz, 1H), 5.45 (s, 2H), 3.80 (s, 3H), 3.20-3.12 (m, 2H), 2.74 (s, 3H), 2.07-1.98 (m, 2H), 1.19 (t, J=7.4 Hz, 3H). $^{13}C$ NMR (151 MHz, Chloroform-d) δ 174.11, 157.04, 153.50, 144.78, 144.03, 139.11, 134.95, 132.96, 132.51, 129.25, 129.08, 126.51, 123.84, 123.75, 123.37, 120.19, 120.15, 119.21, 116.86, 114.37, 111.81, 109.68, 48.99, 31.94, 30.14, 22.42, 16.99, 14.15.

Example 78: 4-(N,N-dipropylsulfamoyl)-2-hydroxybenzoic acid (2ax)

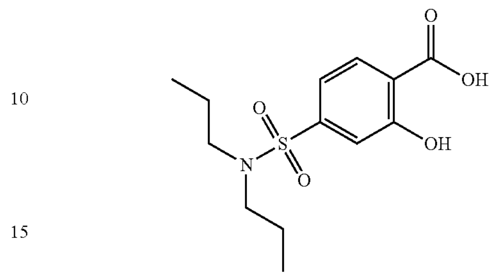

General Procedure B, white solid, 25.6 mg, 85% yield. $^1H$ NMR (600 MHz, DMSO-$d_6$) δ 7.95 (d, J=8.0 Hz, 1H), 7.27 (d, J=8.4 Hz, 1H), 7.26 (s, 1H), 3.04 (t, J=7.5 Hz, 5H), 1.46 (q, J=7.3 Hz, 4H), 0.80 (t, J=7.3 Hz, 6H). $^{13}C$ NMR (151 MHz, DMSO-$d_6$) δ 170.17, 163.64, 141.83, 130.71, 123.28, 114.27, 113.65, 49.72, 21.65, 11.03.

Example 79: (S)-4-(2-Benzamido-3-(4-hydroxyphenyl)propanamido)-2-hydroxybenzoic acid (2ay)

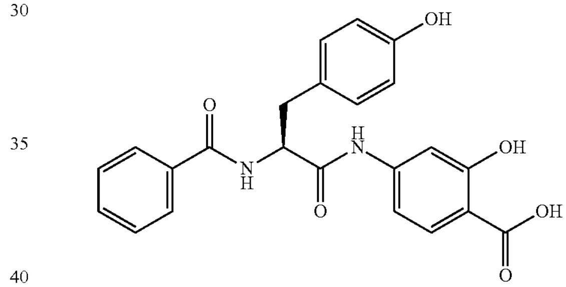

General Procedure B, white solid, 29.8 mg, 71% yield. $^1H$ NMR (600 MHz, DMSO-$d_6$) δ 10.48 (s, 1H), 9.21 (s, 1H), 8.74 (d, J=7.9 Hz, 1H), 7.88-7.81 (m, 2H), 7.75 (d, J=8.7 Hz, 1H), 7.56-7.50 (m, 1H), 7.46 (dd, J=8.3, 6.9 Hz, 2H), 7.41 (d, J=2.0 Hz, 1H), 7.24-7.17 (m, 2H), 7.11 (dd, J=8.7, 2.1 Hz, 1H), 6.74-6.60 (m, 2H), 4.84-4.72 (m, 1H), 3.06-2.97 (m, 2H). $^{13}C$ NMR (151 MHz, DMSO-$d_6$) δ 171.65, 171.53, 166.67, 162.15, 155.89, 145.31, 133.87, 131.48, 131.12, 130.22, 128.28, 127.99, 127.56, 114.99, 110.42, 107.84, 106.16, 56.48, 36.29.

Example 80: 2-((2,6-Dichloro-3-methylphenyl)amino)-6-hydroxybenzoic acid (2az)

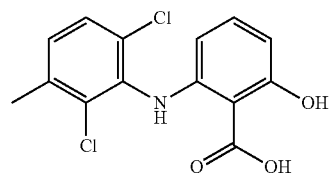 [SMILES: Cc1ccc(Cl)c(Nc2cccc(O)c2C(=O)O)c1Cl]

General Procedure A, white solid, 21.2 mg, 68% yield. $^1H$ NMR (600 MHz, DMSO-$d_6$) δ 11.47 (s, 1H), 7.41 (d, J=8.2

Hz, 1H), 7.22 (d, J=8.3 Hz, 1H), 6.76 (t, J=8.1 Hz, 1H), 5.96 (dd, J=8.0, 1.1 Hz, 1H), 5.36 (dd, J=8.1, 1.1 Hz, 1H), 2.35 (s, 3H). $^{13}$C NMR (151 MHz, DMSO-$d_6$) δ 174.89, 164.85, 147.95, 137.31, 136.50, 133.97, 130.90, 130.85, 128.37, 128.25, 105.59, 104.60, 100.99, 20.70.

Example 81: (S)-2-Ethoxy-6-hydroxy-4-(2-((3-methyl-1-(2-(piperidin-1-yl)phenyl)butyl)amino)-2-oxoethyl)benzoic acid (2ba)

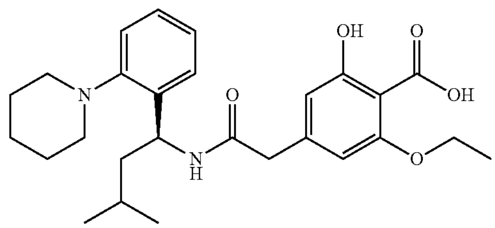 [SMILES: CCOc1cc(CC(=O)N[C@@H](CC(C)C)c2ccccc2N2CCCCC2)cc(O)c1C(=O)O]

General Procedure A, white solid, 26.2 mg, 56% yield. $^1$H NMR (600 MHz, DMSO-$d_6$) δ 8.40 (d, J=8.6 Hz, 1H), 7.30 (d, J=7.7 Hz, 1H), 7.16 (t, J=7.6 Hz, 1H), 7.09 (d, J=8.0 Hz, 1H), 7.04 (t, J=7.5 Hz, 1H), 6.37 (s, 1H), 6.36 (s, 1H), 5.37 (td, J=9.3, 4.9 Hz, 1H), 4.03-3.88 (m, 2H), 3.09 (s, 2H), 1.74-1.64 (m, 2H), 1.59-1.55 (m, 2H), 1.52-1.46 (m, 2H), 1.29 (t, J=7.0 Hz, 3H), 0.90 (t, J=6.4 Hz, 6H). $^{13}$C NMR (151 MHz, DMSO-$d_6$) δ 169.37, 168.79, 157.44, 151.50, 140.88, 140.48, 127.18, 126.02, 124.00, 120.50, 109.54, 107.65, 103.83, 63.94, 46.56, 45.90, 42.83, 26.33, 24.85, 23.84, 23.21, 21.79, 14.64.

Example 82: 2-((3-Chloro-2-methylphenyl)amino)-4-hydroxynicotinic acid (2bb)

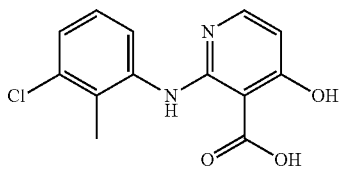 [SMILES: Cc1c(Cl)cccc1Nc1nccc(O)c1C(=O)O]

General Procedure A, white solid, 18.1 mg, 65% yield. $^1$H NMR (600 MHz, DMSO-$d_6$) δ 11.35 (s, 1H), 7.52 (dd, J=7.5, 1.7 Hz, 1H), 7.42-7.34 (m, 3H), 6.22 (d, J=7.3 Hz, 1H), 2.24 (s, 3H). $^{13}$C NMR (151 MHz, DMSO-$d_6$) δ 179.02, 171.17, 153.07, 137.32, 135.37, 134.65, 133.52, 128.67, 128.31, 126.41, 109.37, 95.40, 14.94.

Example 83: 2-Hydroxy-4-((5,5,8,8-tetramethyl-5,6,7,8-tetrahydronaphthalen-2-yl)carbamoyl) benzoic acid (2bc)

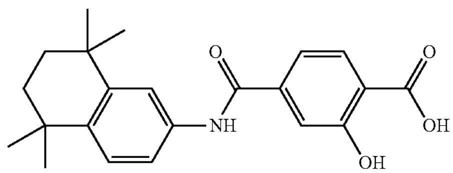 [SMILES: CC1(C)CCC(C)(C)c2cc(NC(=O)c3ccc(C(=O)O)c(O)c3)ccc21]

General Procedure B, white solid, 25.7 mg, 70% yield. $^1$H NMR (600 MHz, DMSO-$d_6$) δ 9.99 (s, 1H), 7.82 (d, J=7.9 Hz, 1H), 7.69 (d, J=1.9 Hz, 1H), 7.58 (dd, J=8.5, 1.9 Hz, 1H), 7.30-7.17 (m, 3H), 1.64 (m, 4H), 1.23 (m, 12H). $^{13}$C NMR (151 MHz, DMSO-$d_6$) δ 171.36, 165.16, 162.32, 144.44, 139.68, 138.12, 136.69, 130.03, 126.34, 122.28, 118.26, 118.07, 115.59, 115.08, 34.66, 34.60, 34.00, 33.54, 31.68, 31.65, 30.71, 29.62.

Example 85: 5-(5-(2-Fluorophenyl)-1,2,4-oxadiazol-3-yl)-2-hydroxybenzoic acid (2bd)

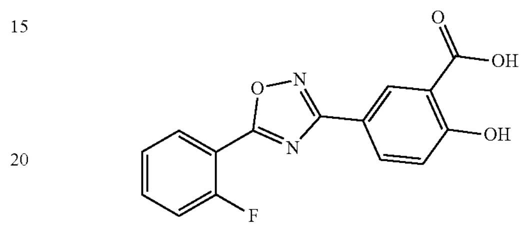

General Procedure A, white solid, 24.3 mg, 81% yield. $^1$H NMR (600 MHz, DMSO-$d_6$) δ 8.46 (s, 1H), 8.23 (t, J=7.6 Hz, 1H), 7.89 (d, J=8.4 Hz, 1H), 7.81-7.75 (m, 1H), 7.54 (dd, J=11.1, 8.4 Hz, 1H), 7.48 (t, J=7.6 Hz, 1H), 6.82 (d, J=8.5 Hz, 1H). $^{13}$C NMR (151 MHz, DMSO-$d_6$) δ 171.89, 171.86, 168.06, 166.47, 160.79, 159.08, 135.52, 135.46, 131.14, 130.88, 129.71, 125.49, 125.47, 117.52, 117.36, 117.22, 113.80, 112.03, 111.95.

Example 86: Single Crystal X-Ray Structure of $[Pd_2Cl_2(L42)_2]$ Complex

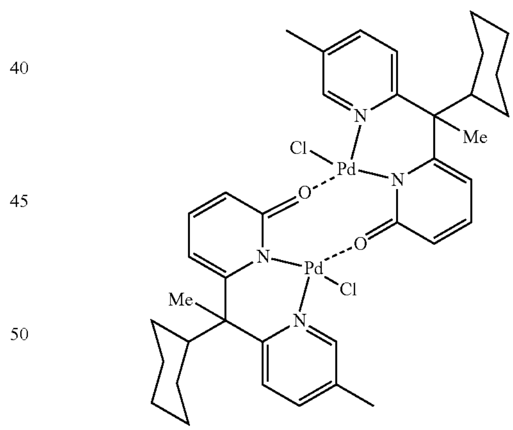

To a solution of $Pd(OAc)_2$ (11.2 mg, 0.05 mmol) in $CHCl_3$ (1 mL) was added L42 (14.8 mg, 0.05 mmol). The mixture was stirred at 65° C. for 8 hours. After filtering through a pad of Celite, the solution was concentrated under vacuum to afford a brown powder (17.4 mg, 74% yield). The crystal was grown in toluene, and the structure was determined by X-ray diffraction (FIG. 1).

| Bond precision: C—C = 0.0046 Å | Wavelength = 0.71073 |
|---|---|
| Cell: a = 12.4438(8) b = 13.3721(8) c = 14.9265(8) | |

-continued

| alpha = 96.804(2) beta = 105.727(2) gamma = 90.019(2) | Temperature: 100 K |
|---|---|
| **Calculated** | **Reported** |
| Volume 2372.6(2) | 2372.6(2) |
| Space group P −1 | P −1 |
| Hall group -P 1 | -P 1 |
| Moiety formula C38 H46 C12 N4 O2 Pd2, 2(C7 H8) | C38 H46 Cl2 N4 O2 Pd2, 2(C7 H8) |
| Sum formula C52 H62 C12 N4 O2 Pd2 | C52 H62 Cl2 N4 O2 Pd2 |
| Mr 1058.76 | 1058.75 |
| Dx, g cm−3 1.482 | 1.482 |
| Z 2 | 2 |
| Mu (mm−1) 0.915 | 0.915 |
| F000 1088.0 | 1088.0 |
| F000' 1084.91 | |
| h, k, lmax 15, 16, 18 | 15, 16, 18 |
| Nref 9777 | 9731 |
| Tmin, Tmax 0.916, 0.982 | 0.364, 0.491 |

Correction method = # Reported T Limits: Tmin = 0.364 Tmax = 0.491
AbsCorr = MULTI-SCAN
Data completeness = 0.995
Theta(max) = 26.435
R(reflections) = 0.0339(8381)
wR2(reflections) = 0.0801(9731)
S = 1.091
Npar = 606.

Example 87: Single Crystal X-Ray Structure of $[Pd_2(TFA)_2(L27)_2]$ Complex

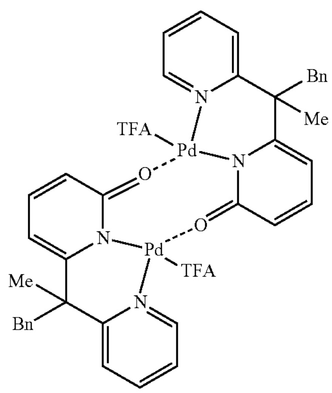

Figure 2:
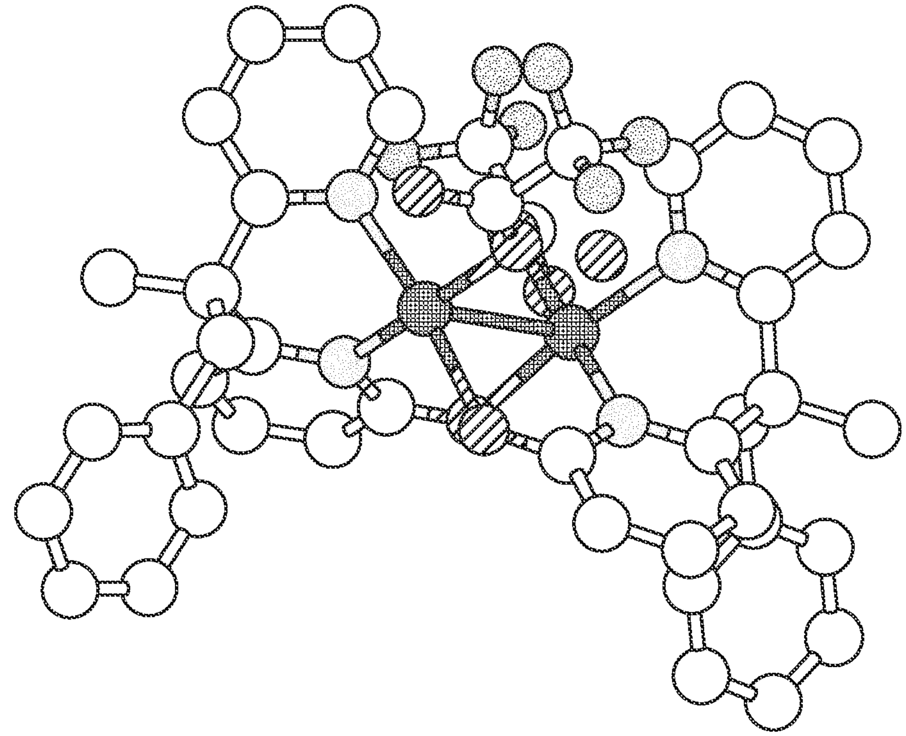
FIG. 2: Single crystal X-ray structure of $[Pd_2(TFA)_2(L27)_2]$ complex.

General procedure: To a solution of $Pd(TFA)_2$ (16.6 mg, 0.05 mmol) in $CDCl_3$ (1 mL) was added L27 (14.5 mg, 0.05 mmol). The mixture was stirred at 20° C. for 24 hours. After filtering through a pad of Celite, the solution was concentrated under vacuum to afford a brown powder (15.0 mg, 61% yield). The crystal was grown in toluene, and the structure was determined by X-ray diffraction (FIG. 2).

| Bond precision: C—C = 0.0060 Å | Wavelength = 0.71073 |
|---|---|
| Cell: a = 19.8127(12) b = 10.4139(7) c = 19.5456(13) | |
| alpha-90 beta = 109.949(2) gamma = 90 | Temperature: 100 K |
| **Calculated** | **Reported** |
| Volume 3790.8(4) | 3790.8(4) |
| Space group P 21/c | P 1 21/c 1 |
| Hall group -P 2ybc | -P 2ybc |
| Moiety formula C42 H34 F6 N4 O6 Pd2 | C42 H34 F6 N4 O6 Pd2 |
| Sum formula C42 H34 F6 N4 O6 Pd2 | C42 H34 F6 N4 O6 Pd2 |
| Mr 1017.53 | 1017.53 |
| Dx, g cm−3 1.783 | 1.783 |
| Z 4 | 4 |
| Mu (mm−1) 1.035 | 1.035 |
| F000 2032.0 | 2032.0 |
| F000' 2025.09 | |
| h, k, lmax 26, 13, 26 | 26, 13, 26 |
| Nref 9423 | 9412 |
| Tmin, Tmax 0.733, 0.756 | 3790.8(4) |

Correction method = # Reported T Limits: Tmin = 0.694 Tmax = 0.746
AbsCorr = MULTI-SCAN
Data completeness = 0.999
Theta(max) = 28.307
R(reflections) = 0.0444(8236)
wR2(reflections) = 0.1188(9412)
S = 1.073
Npar = 552.

Numbered references in the examples above are as follows:

1. Gottlieb, H. E., Kotlyar, V., Nudelman, A. NMR chemical shifts of common laboratory solvents as trace impurities. *J. Org. Chem.* 62, 7512-7515 (1997).
2. Di Marco, V. B., Yokel, R. A., Ferlin, M. G., Tapparo, A., Bombi, G. G.: Evaluation of 3,4-hydroxypyridinecarboxylic acids as possible bidentate chelating agents for aluminium(III): synthesis and metal-ligand solution chemistry. *Eur. J. Inorg. Chem.* 2648-2655 (2002).

We claim:

1. A process for making a compound of formula (2):

(2)

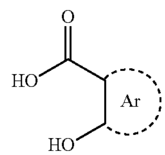

which comprises contacting a compound of formula (1):

(1)

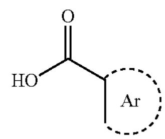

with a source of Pd(II) in the presence of $O_2$ and a ligand selected from the group consisting of:

| | |
|---|---|
| L26 | 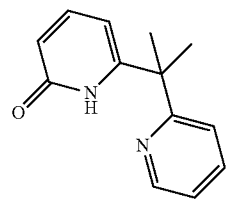 [SMILES: CC(C)(c1ccccn1)c1cccc(=O)[nH]1] |

-continued
L27
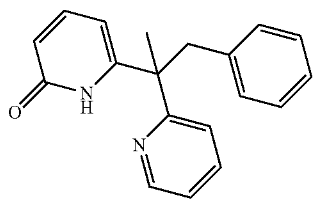 [SMILES: CC(Cc1ccccc1)(c1ccccn1)c1cccc(=O)[nH]1]
L28
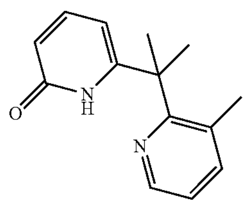
L29
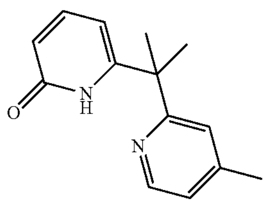 [SMILES: Cc1ccnc(C(C)(C)c2cccc(=O)[nH]2)c1]
L30
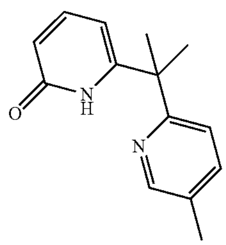 [SMILES: Cc1ccc(C(C)(C)c2cccc(=O)[nH]2)nc1]
L31
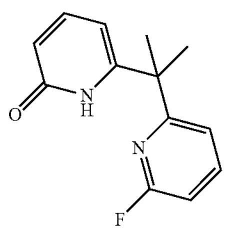 [SMILES: CC(C)(c1cccc(F)n1)c1cccc(=O)[nH]1]
L32
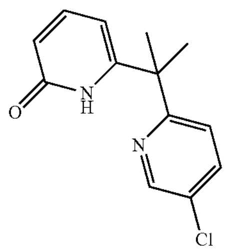 [SMILES: CC(C)(c1ccc(Cl)cn1)c1cccc(=O)[nH]1]
L33
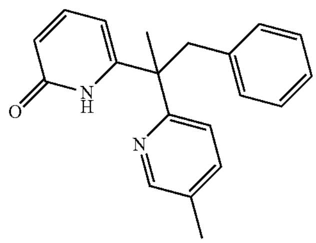 [SMILES: Cc1ccc(C(C)(Cc2ccccc2)c2cccc(=O)[nH]2)nc1]
-continued
L34
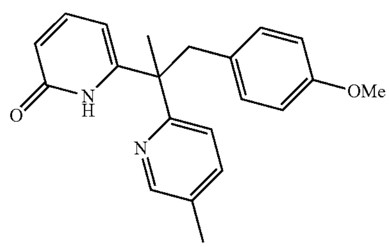 [SMILES: COc1ccc(CC(C)(c2ccc(C)cn2)c2cccc(=O)[nH]2)cc1]
L35
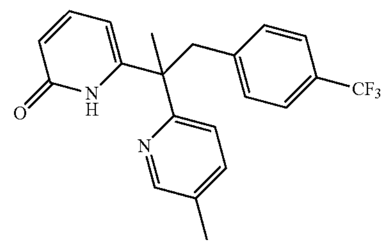 [SMILES: Cc1ccc(C(C)(Cc2ccc(C(F)(F)F)cc2)c2cccc(=O)[nH]2)nc1]
L36
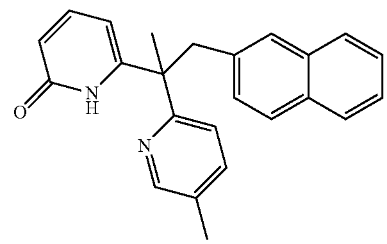 [SMILES: Cc1ccc(C(C)(Cc2ccc3ccccc3c2)c2cccc(=O)[nH]2)nc1]
L37
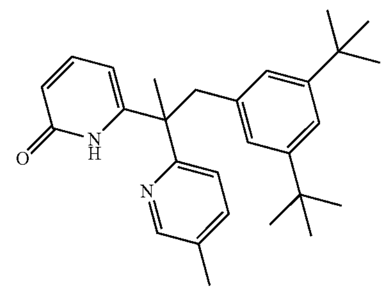 [SMILES: Cc1ccc(C(C)(Cc2cc(C(C)(C)C)cc(C(C)(C)C)c2)c2cccc(=O)[nH]2)nc1]
L38
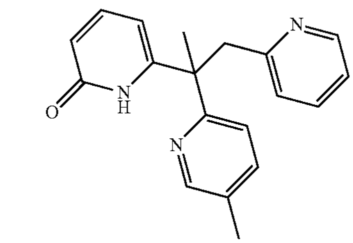 [SMILES: Cc1ccc(C(C)(Cc2ccccn2)c2cccc(=O)[nH]2)nc1]
L39
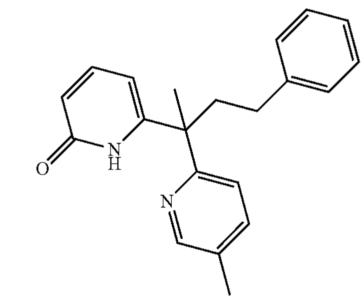 [SMILES: Cc1ccc(C(C)(CCc2ccccc2)c2cccc(=O)[nH]2)nc1]

-continued

L40

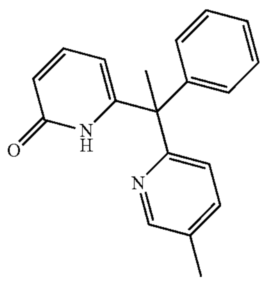 [SMILES: Cc1ccc(C(C)(c2ccccc2)c2cccc(=O)[nH]2)nc1]

L41

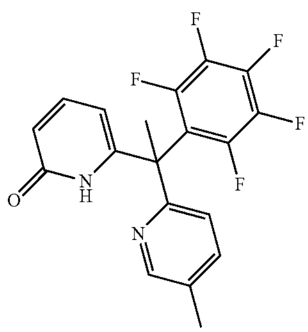 [SMILES: Cc1ccc(C(C)(c2cccc(=O)[nH]2)c2c(F)c(F)c(F)c(F)c2F)nc1]

L42

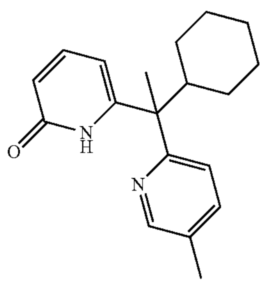 [SMILES: Cc1ccc(C(C)(c2cccc(=O)[nH]2)C2CCCCC2)nc1]

L43

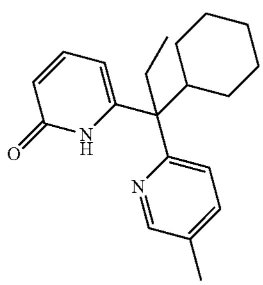 [SMILES: CCC(c1ccc(C)cn1)(c1cccc(=O)[nH]1)C1CCCCC1]

L44

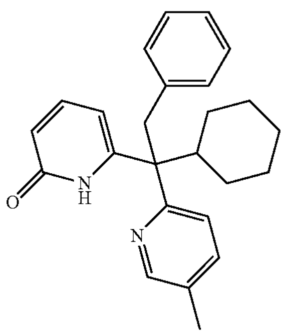 [SMILES: Cc1ccc(C(Cc2ccccc2)(c2cccc(=O)[nH]2)C2CCCCC2)nc1]

-continued

L45

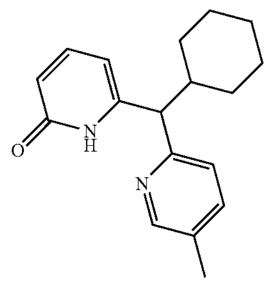 [SMILES: Cc1ccc(C(c2cccc(=O)[nH]2)C2CCCCC2)nc1]

in a solvent under conditions sufficient to provide the compound of formula (2), wherein:

Ar is selected from the group consisting of:

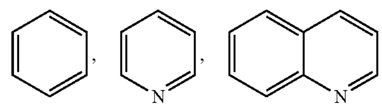,

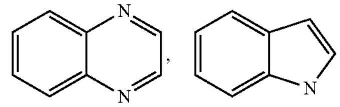,

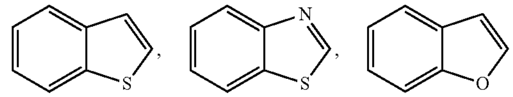,

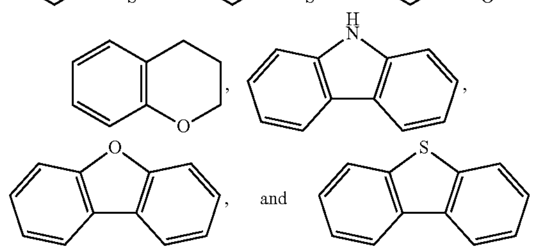

,  and wherein each ring in Ar is independently and optionally substituted with one to four substituents selected from the group consisting of —CN, halo, oxo, $NR^AR^B$, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, —C(O)H, C(O)$C_1$-$C_6$-alkyl, C(O)$NR^AR^B$, S(O)$NR^AR^B$, $S(O)_2NR^AR^B$, $C_3$-$C_{14}$-cycloalkyl, $C_6$-$C_{10}$-aryl, $C_6$-$C_{10}$-aryloxy, 3- to 14-membered heterocycloalkyl and —($C_1$-$C_6$-alkyl)-(3-to 14-membered heterocycloalkyl) (wherein 1-4 ring members are independently selected from N, O, and S), and 5-to 10-membered heteroaryl (wherein 1-4 heteroaryl members are independently selected from N, O, and S), wherein each alkyl, aryl, cycloalkyl, heterocycloalkyl, and heteroaryl moiety is optionally substituted with one to four substituents selected from the group consisting of halo, oxo, $C_1$-$C_6$-alkyl, $C_1$-$C_6$-haloalkyl, $C_1$-$C_6$-alkoxy, C(O)$NR^AR^B$, $C_1$-$C_6$-alkoxy, $C_6$-$C_{10}$-aryl (optionally substituted by one to three halo and $C_1$-$C_6$-alkyl), and 5- to 10-membered heteroaryl (wherein 1-4 heteroaryl members are independently selected from N, O, and S; optionally substituted by one to three substituents selected from $C_1$-$C_6$-alkyl and 5- to 10-membered heteroaryl); and $R^A$ and $R^B$ are independently selected from the group consisting of H, $C_1$-$C_6$-alkyl, $C_1$-$C_6$-haloalkyl, —$C_1$-$C_6$-alkyl-$C_6$-$C_{10}$-aryl, $C(O)C_1$-$C_6$-alkyl, $C(O)C_1$-$C_6$-alkyl-$C_6$-$C_{10}$-aryl, $C(O)OC_1$-$C_6$-alkyl, $C_6$-$C_{10}$-aryl (optionally fused to $C_3$-$C_{14}$-cycloalkyl that is optionally substituted by one to four halo and $C_1$-$C_6$-alkyl), wherein each aryl is optionally substituted with one to three substituents selected from $C_1$-$C_6$-alkyl, halo, hydroxy, $C_1$-$C_6$-haloalkyl, and 3- to 14-membered heterocycloalkyl (wherein 1-4 ring members are independently selected from N, O, and S);

each alkyl is optionally substituted with one to three substituents selected from halo, NRR' (wherein R and R' are independently selected from H, $C_1$-$C_6$-alkyl, $C(O)C_1$-$C_6$-alkyl, and $C(O)C_6$-$C_{10}$-aryl).

2. The process according to claim 1, wherein the compound of formula (1) is selected from the following table:

| | | | |
|---|---|---|---|
| 1a | 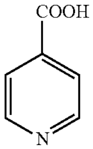 | 1ac | 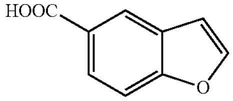 [SMILES: O=C(O)c1ccc2occc2c1] |
| 1b | 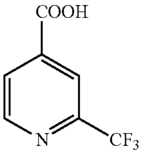 [SMILES: O=C(O)c1ccnc(C(F)(F)F)c1] | 1ad | 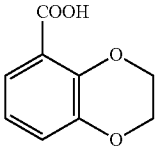 [SMILES: O=C(O)c1cccc2c1OCCO2] |
| 1c | 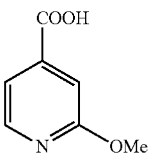 [SMILES: COc1cc(C(=O)O)ccn1] | 1ae | 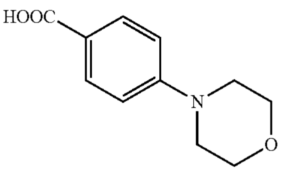 [SMILES: O=C(O)c1ccc(N2CCOCC2)cc1] |
| 1d | 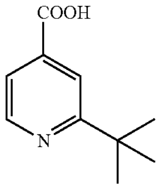 | 1af | 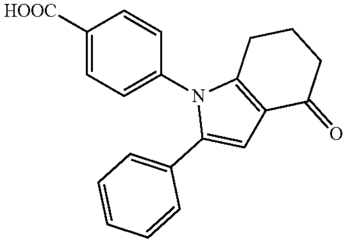 [SMILES: O=C(O)c1ccc(-n2c(-c3ccccc3)cc3c2CCCC3=O)cc1] |
| 1e | 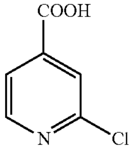 | 1ag | 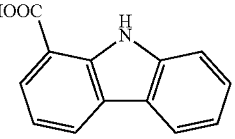 |
| 1f | 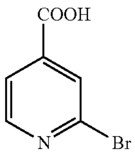 | 1ah | 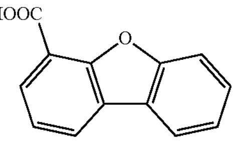 |
| 1g | 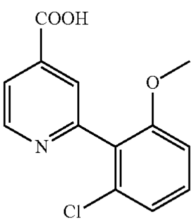 [SMILES: COc1cccc(Cl)c1-c1cc(C(=O)O)ccn1] | 1ai | 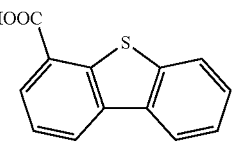 |

-continued
1h
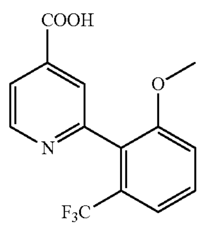 [SMILES: COc1cccc(C(F)(F)F)c1-c1cc(C(=O)O)ccn1]
1aj
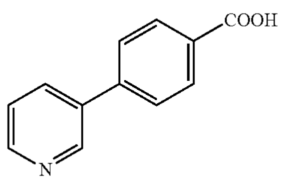 [SMILES: O=C(O)c1ccc(-c2cccnc2)cc1]
1i
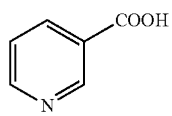
1ak
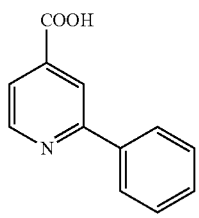 [SMILES: O=C(O)c1ccnc(-c2ccccc2)c1]
1j
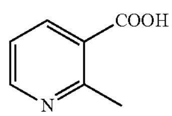
1al
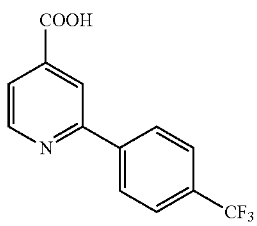 [SMILES: O=C(O)c1ccnc(-c2ccc(C(F)(F)F)cc2)c1]
1k
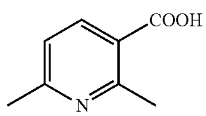
1am
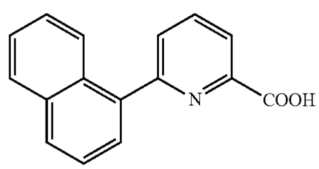 [SMILES: O=C(O)c1cccc(-c2cccc3ccccc23)n1]
1l
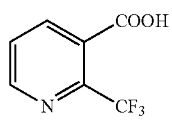
1an
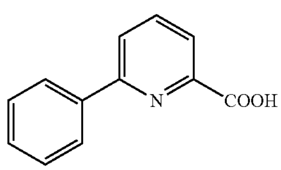 [SMILES: O=C(O)c1cccc(-c2ccccc2)n1]
1m
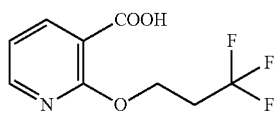 [SMILES: O=C(O)c1cccnc1OCCC(F)(F)F]
1ao
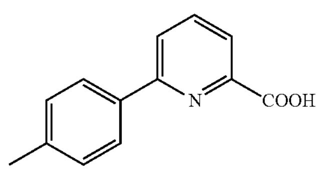 [SMILES: Cc1ccc(-c2cccc(C(=O)O)n2)cc1]
1n
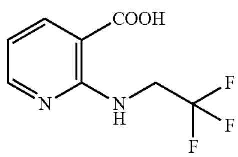 [SMILES: O=C(O)c1cccnc1NCC(F)(F)F]
1ap
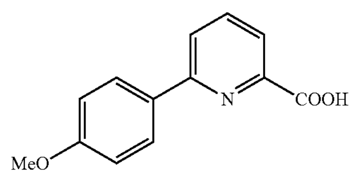 [SMILES: COc1ccc(-c2cccc(C(=O)O)n2)cc1]
1o
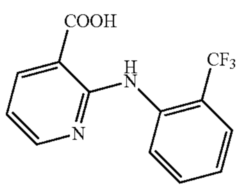 [SMILES: O=C(O)c1cccnc1Nc1ccccc1C(F)(F)F]
1aq
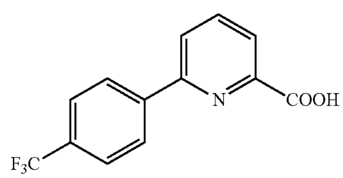 [SMILES: O=C(O)c1cccc(-c2ccc(C(F)(F)F)cc2)n1]

-continued
1p
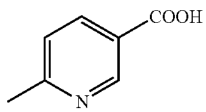
1ar
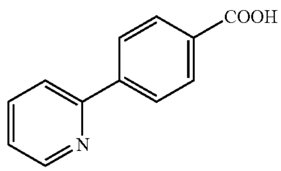 [SMILES: O=C(O)c1ccc(-c2ccccn2)cc1]
1q
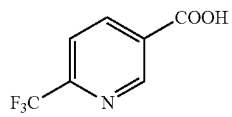 [SMILES: O=C(O)c1ccc(C(F)(F)F)nc1]
1as
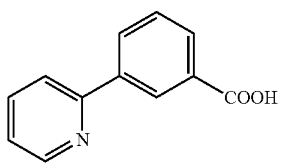 [SMILES: O=C(O)c1cccc(-c2ccccn2)c1]
1r
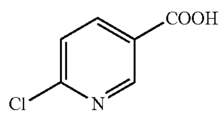
1at
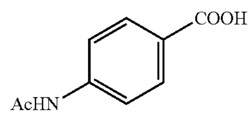 [SMILES: CC(=O)Nc1ccc(C(=O)O)cc1]
1s
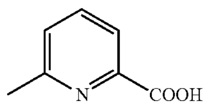
1au
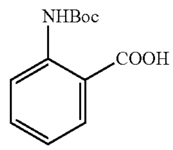 [SMILES: CC(C)(C)OC(=O)Nc1ccccc1C(=O)O]
1t
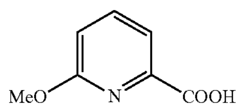 [SMILES: COc1cccc(C(=O)O)n1]
1av
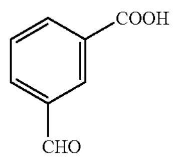 [SMILES: O=Cc1cccc(C(=O)O)c1]
1u
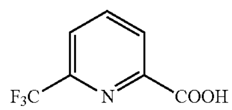
1aw
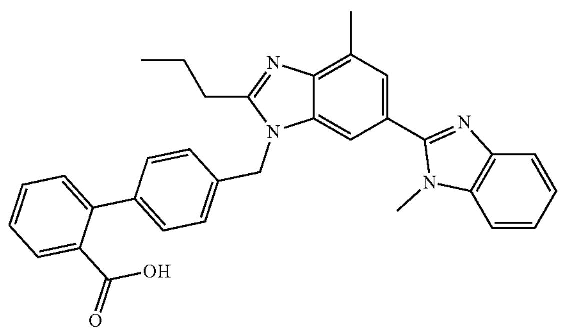 [SMILES: CCCc1nc2c(C)cc(-c3nc4ccccc4n3C)cc2n1Cc1ccc(-c2ccccc2C(=O)O)cc1]
1v
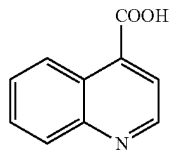 [SMILES: O=C(O)c1ccnc2ccccc12]
1ax
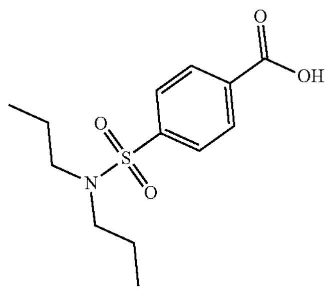 [SMILES: CCCN(CCC)S(=O)(=O)c1ccc(C(=O)O)cc1]

-continued

| | | | |
|---|---|---|---|
| 1w | 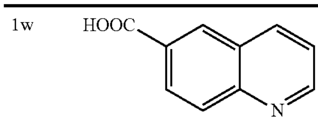 | 1ay | 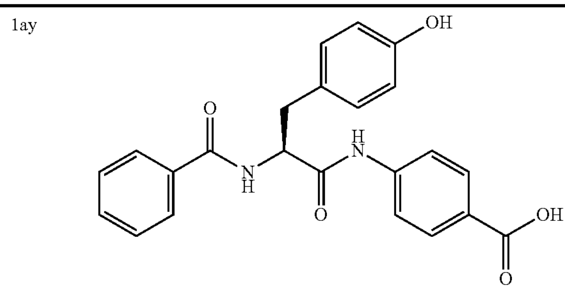 |
| 1x | 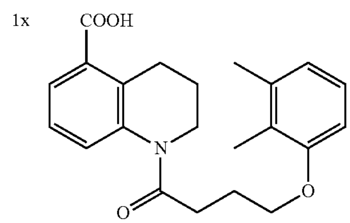 | 1az | 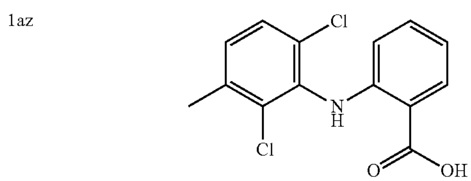 |
| 1y | 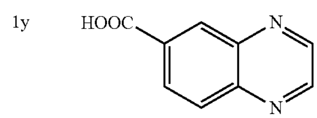 | 1ba | 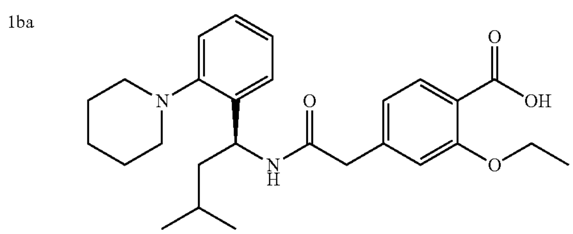 |
| 1z | 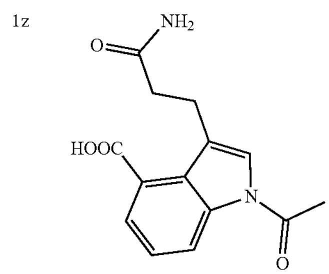 | 1bb | 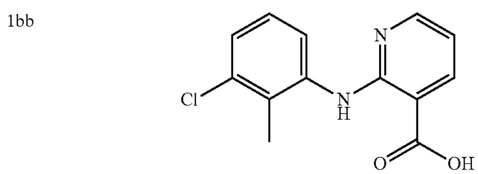 |
| 1aa | 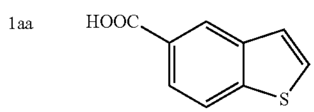 | 1bc | 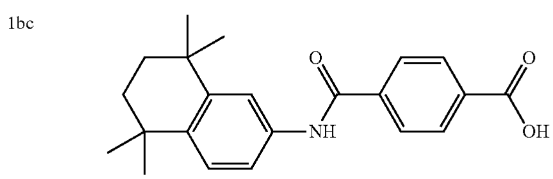 |
| 1ab | 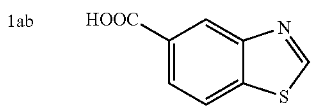 | 1bd | 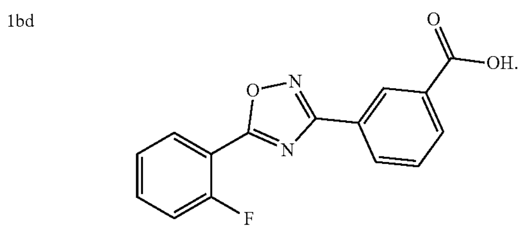 |

3. The process of claim 1, wherein the source of Pd(II) is a Pd(II) salt.

4. The process of claim 3, wherein the Pd(II) salt is at least one selected from the group consisting of $Pd(OAc)_2$, $Pd(TFA)_2$, $PdCl_2$, and $Pd(CH_3CN)_2Cl_2$.

5. The process of claim 1, wherein the contacting further occurs in the presence of a non-nucleophilic base.

6. The process of claim 5, wherein the non-nucleophilic base is KOAc, NaOAc, CsOAc, $K_3PO_4$, $K_2HPO_4$, $KH_2PO_4$, or $K_2CO_3$.

7. The process of claim 1, wherein the solvent is a polar aprotic solvent.

8. The process of claim 7, wherein the polar aprotic solvent is N-methylpyrrolidine (NMP), dimethylacetamide (DMA), dimethylformamide (DMF), tetrahydrofuran (THF), acetone, acetonitrile, ethylacetate, hexamethylphosphoric triamide (HMPT), or dimethylsulfoxide (DMSO).
9. The process of claim 1 wherein the ligand is:
L42
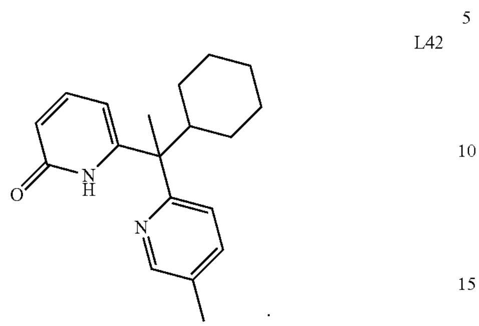
* * * * *